United States Patent [19]

Hanson et al.

[11] Patent Number: 5,877,302
[45] Date of Patent: Mar. 2, 1999

[54] COMPACTED NUCLEIC ACIDS AND THEIR DELIVERY TO CELLS

[75] Inventors: Richard W. Hanson; Jose C. Perales, both of Cleveland Heights; Thomas W. Ferkol, Euclid, all of Ohio

[73] Assignees: Case Western Reserve University, Cleveland; Ohio University, Athens, both of Ohio

[21] Appl. No.: 716,415

[22] PCT Filed: Mar. 23, 1995

[86] PCT No.: PCT/US95/03677

§ 371 Date: Feb. 12, 1997

§ 102(e) Date: Feb. 12, 1997

[87] PCT Pub. No.: WO95/25809

PCT Pub. Date: Sep. 28, 1995

Related U.S. Application Data

[63] Continuation-in-part of Ser. No. 216,534, Mar. 23, 1994, abandoned.

[51] Int. Cl.$^6$ .................................................. C12N 15/11
[52] U.S. Cl. .............................................. 536/23.1
[58] Field of Search ................................ 435/172.3, 91.1; 536/23.1

[56] References Cited

U.S. PATENT DOCUMENTS

| | | | |
|---|---|---|---|
| 5,108,921 | 4/1992 | Low et al. | 435/172.3 |
| 5,120,657 | 6/1992 | McCabe et al. | 435/287 |
| 5,122,466 | 6/1992 | Stomp et al. | 435/172.3 |
| 5,149,782 | 9/1992 | Chang et al. | 530/326 |
| 5,166,320 | 11/1992 | Wu et al. | 530/395 |
| 5,354,844 | 10/1994 | Beug et al. | 530/345 |

FOREIGN PATENT DOCUMENTS

| | | |
|---|---|---|
| 0388758 | 3/1990 | European Pat. Off. . |
| 0 388 758 | 9/1990 | European Pat. Off. . |
| 92 19749 | 11/1992 | WIPO . |
| 9219749 | 11/1992 | WIPO . |
| 9525809 | 9/1995 | WIPO . |

OTHER PUBLICATIONS

Bunnell, B., Askari, F., Wilson. J., "Targeted Delivery of Antisense Oligonucleotides by Molecular Conjugates", Somatic Cell and Molecular Genetics, vol. 18, No. 6 1992, pp. 559–569.

Gershon, H., Ghirlando, R., Guttman, S., Minsky, A., "Mode of Formation and Structural Features of DNA–Cationic Liposome Complexes Used for Transfection". American Chemical Society, Biochemistry 1993, 32 7143–7151.

Perales, J., Ferkol, T., Beegen, H., Ratnoff, O., Hanson, R., "Gene transfer in vivo: Sustained expression and regulation of genes introduced into the liver by receptor–targeted uptake". Proc. Nat. Acad. Sci. vol. 91, pp. 4086–4090, Apr. 1994.

Perales, J., Ferkol, T., Molas, M., Hanson, R., "An evaluation of receptor–mediated gene transfer using synthetic DNA–ligand complexes". Eur. J. Biochem. 226, 255–266 (1994).

Davidson, B., Fasman, G., "The Single–Stranded Polyadenylic Acid–Poly–L–lysine Complex. A Conformational Study and Characterization". Pub. No. 662 Biochemistry vol. 8 Oct. 1969.

Wagner, Ernst et al. Transferin–polycation–DNA complexes: The effect of polycations on the structure of the complex and DNA delivery to cells: Proc. Natl. Acad. Sci. USA. vol. 88., pp. 4255–4259, May 1991.

Christiano, Richard et al. "Hepatic gene therapy: Adenovirus enhancement of receptor–mediated gene delivery and expression in primary hepatocytes." Proc. Natl. Acad. Sci. USA. vol. 90, pp. 2122–2126. Mar. 1993.

Wu, George Y. et al. "Receptor–mediated in Vitro Gene Transformation by a Soluable DNA Carrier System." The Journal of Biological Chemistry. vol. 262, No. 10, pp. 4429–4432. Apr. 5, 1987.

Wilson, James M. et al. "Hepatocyte–directed Gene Tranwsfer in Vivo Leads to Transient Improvement of Hypercholostolemia in Low Density Lipoprotein Receptor–deficient Rabbits." The Journal of Biological Chemistry. vol. 267, No. 2, pp. 963–967, Jan. 15, 1992.

Neda, Hiroshi et al. "Chemical Modification of an Ecotropic Murine Leukimia Virus Results in Redirection of Its Target Cell Specificity." The Journal of Biological Chemistry. vol. 266, No. 22. pp. 14143–14146. Aug. 5, 1991.

Wu. George Y. et al. "Evidence for Targeted Gene Delivery to Hep G2 Hepatoma Cells in Vitro." Biochemistry, vol. 27, pp. 887–892. 1988.

Wu, George Y. et al. "Receptor–mediated Gene Delivery in Vivo." The Journal of Biological Chemistry, vol. 266 No. 22, pp. 14338–14342. Aug. 5, 1991.

Wu, George Y. et al. "Receptor–mediated Gene Delivery and Expression in Vivo." The Journal of Biological Chemistry, vol. 263 No. 29, pp. 14621–14624. Oct. 15, 1988.

Wu, Catherine H. et al. "Targeting Genes: Delivery and Persitent Expression of a Foreign Gene Driven by Mammalian Regulatory Elements in Vivo." The Journal of Biological Chemicstry, vol. 264, No. 29, pp. 16985–16987. Oct. 15, 1989.

(List continued on next page.)

*Primary Examiner*—James Ketter
*Attorney, Agent, or Firm*—Banner & Witcoff, Ltd.; Iver Cooper

[57] ABSTRACT

Nucleic acids are compacted, substantially without aggregation, to facilitate their uptake by target cells of an organism to which the compacted material is administered. The nucleic acids may achieve a clinical effect as a result of gene expression, hybridization to endogenous nucleic acids whose expression is undesired, or site-specific integration so that a target gene is replaced, modified or deleted. The targeting may be enhanced by means of a target cell-binding moiety. The nucleic acid is preferably compacted to a condensed state.

57 Claims, 24 Drawing Sheets

OTHER PUBLICATIONS

Curiel, David T. et al. "Adenovirus enhancement of transferrin–polylysine–mediated gene delivery." Proc. Natl. Acad. Sci. USA. vol. 88, pp. 8850–8854. Oct. 1991.

Lerman, L.S. "A Transition to a Compact Form of DNA in Polymer Solutions." Proc. Natl. Acad. Sci. USA. vol. 68, No. 8. pp. 1886–1980. Aug. 1971.

Gosule, Leonard C. et al. "Compact form of DNA induced by spermidine." Nature. vol. 259, Jan. 29, 1976.

Laemmli, U.K. "Characterization of DNA condensates induced by pol(ethylen oxide) and polylysine,." Proc. Nat. Acad. Sci. USA. vol. 72, No. 11, pp. 4288–4292. Nov. 1975.

Post, Carol Beth et al. "Theory of DNA Condensation: Collapse Versus Aggregation." Biopolymers. vol. 21, pp. 2123–2137. 1982.

Schlepper–Schafer, Jutta et al. "Endocytosis Via Galactose Receptors in Vivo." Experimental Cell Research 165 1986 pp. 494–506.

Wagner et al., Proc. Natl. Acad. Sci., USA 88, pp. 4255–4259, 1991.

Midoux et al., Nuc. Acids. Res., vol. 21 (4), pp. 871–878, 1993.

Kaetzel et al., Proc. Natl Acad. Sci., USA 88, pp. 8796–8800, 1991.

Laemmli et al., Proc. Natl. Acad. Sci. USA 72(11), pp. 4288–4292, 1975.

Bunnell, Bruce A. et al., Somatic Cell and Molecular Genetics, "Targeted Delivery of Antisense Oligonucleotides by Molecular Conjugates," USA vol. 18, No. 6, pp. 559–569, 1992.

Gershon H. et al., Biochemistry, "Mode of Formation and Structual Features of DNA–Cationic Lipsome Complex Used for Transfection", vol. 32, pp. 7143–7151, 1993.

Perales, J.C. et al., European Journal of Biochemistry, "An evaluation of receptor mediated gene transfer using synthetic DNA–ligand complexes", vol. 256, No. 2, pp. 255–266, Dec. 1994.

Perales, J.C. et al., Proceedings of the National Academy of Sciences of USA, "Gene transfer in vivo: Sustained expression and regulation of genes introduced into the liver by receptor–targeted uptake", vol. 91, No. 9, pp. 4086–4090, Apr. 26, 1994.

Laskin et al., *CRC Handbook of Microbiology, vol. II,* ($2^{nd}$ ed.), 1978, p. 596.

Orkin et al., *Report and Recommendations of the Panel to Assess the NIH Investment in Research on Gene Therapy,* 1995, NIH.

FIG.1B        FIG.1C        FIG.1D
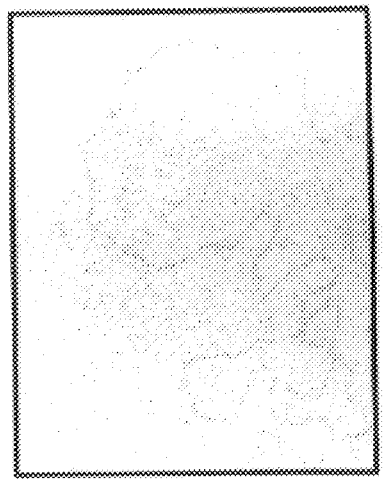
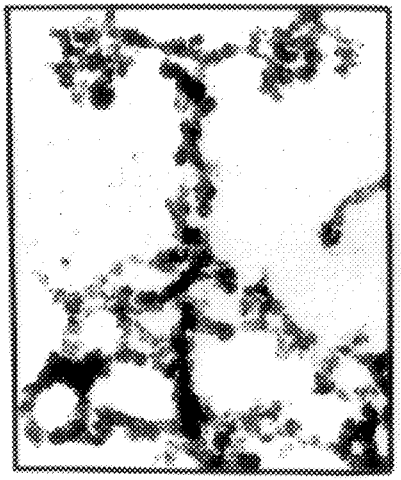
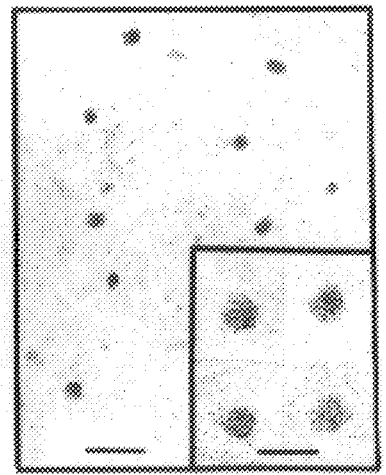
FIG.1E

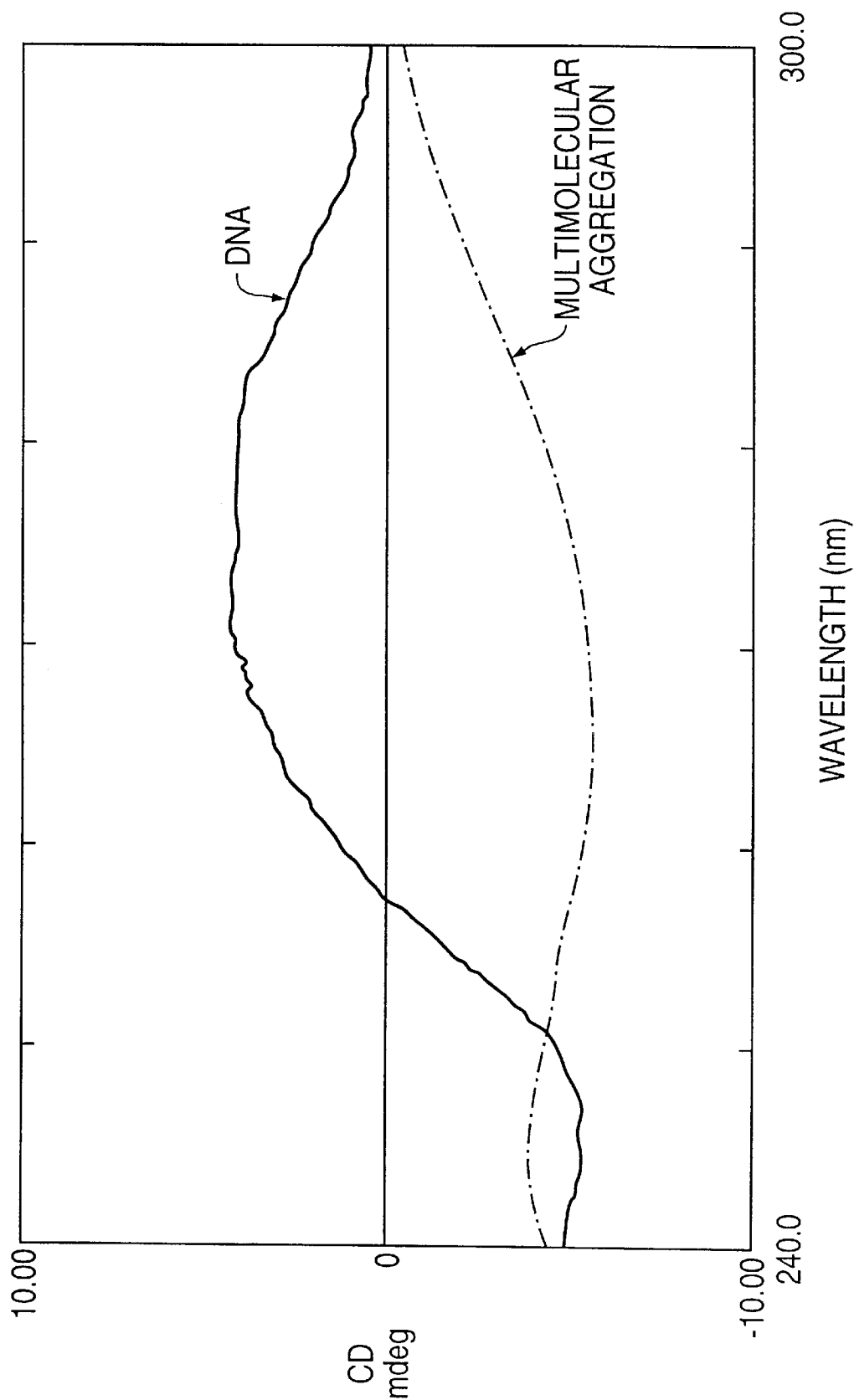

COMPACTED NUCLEIC ACIDS AND THEIR DELIVERY TO CELLS

This application, which is a national stage application filed under 35 USC 371, (PCT/-U.S. Ser. No. 95/03677 which is a continuation-in-part of Ser. No. 08/216,534, filed Mar. 23, 1994, now abandoned, hereby incorporated by reference in its entirety.

BACKGROUND OF THE INVENTION

1. Field of the Invention

The present invention relates to the compaction of nucleic acids and the delivery of compacted exogenous nucleic acids to cells of multicellular organisms, in vivo.

2. Description of the Background Art

Functional exogenous genes can be introduced to mammalian cells in vitro by a variety of physical methods, including transfection, direct microinjection, electroporation, and coprecipitation with calcium phosphate. Most of these techniques, however, are impractical for delivering genes to cells within intact animals.

Receptor-Mediated Uncompacted DNA Delivery In Vivo. Receptor-mediated gene transfer has been shown to be successful in introducing transgenes into suitable recipient cells, both in vitro and in vivo. This procedure involves linking the DNA to a polycationic protein (usually poly-L-lysine) containing a covalently attached ligand, which is selected to target a specific receptor on the surface of the tissue of interest. The gene is taken up by the tissue, transported to the nucleus of the cell and expressed for varying times. The overall level of expression of the transgene in the target tissue is dependent on several factors: the stability of the DNA-carrier complex, the presence and number of specific receptors on the surface of the targeted cell, the receptor-carrier ligand interaction, endocytosis and transport of the complex to the nucleus, and the efficiency of gene transcription in the nuclei of the target cells.

Wu, et al., U.S. Pat. No. 5,166,320, discloses tissue-specific delivery of DNA using a conjugate of a polynucleic acid binding agent (such as polylysine, polyarginine, polyornithine, histone, avidin, or protamine) and a tissue receptor-specific protein ligand. For targeting liver cells, Wu suggests "asialoglycoprotein (galactose-terminal) ligands". These may be formed, Wu says, either by desialation of appropriate glycoproteins, or by coupling lactose to non-galactose bearing proteins. The molar ratio of polynucleic acid to conjugate is in the range 1:10 to 10:1, more typically 1:5 to 5:1, more preferably 1:2 to 3:1. While not stated by Wu et al., in our hands, Wu's method resulted in structures with a diameter of at least 80 nm.

Low, et al., U.S. Pat. No. 5,108,921, disclose binding biotin to DNA to transform a cell using receptor mediated endocytosis.

Stomp, et al., U.S. Pat. No. 5,122,466 and McCabe, et al., U.S. Pat. No. 5,120,657 disclose attaching DNA to a metal pellet by covalently attaching polylysine to the material and then allowing DNA to be complexed to it. The resulting product is then used for ballistic transformation of a cell. See Stomp, et al., column 7, lines 29–37and McCabe, et al., column 7, lines 49–65.

Wagner, et al., Proc. Natl. Acad. Sci., 88:4255–4259 (1991) disclose complexing a transferrin-polylysine conjugate with DNA for delivering DNA to cells via receptor mediated endocytosis. Wagner, et al., teach that it is important that there be sufficient polycation in the mixture to ensure compaction of plasmid DNA into toroidal structures of 80–100 nm diameter, which, they speculate, facilitate the endocytic event. Wagner et al. do not recognize the value of attaining smaller diameter structures or teach how to obtain a greater degree of compaction. It is believed that Wagner et al's structures are multimolecular complexes, which have the disadvantage that they are more vulnerable to macrophage phagocytosis and less amenable to uptake by target tissues.

Direct injection of Naked, Uncompacted DNA. The possibility of detecting gene expression by directly injecting naked DNA into animal tissues was demonstrated first by Dubenski et al, Proc. Nat. Acad. Sci. USA, 81:7529–33 (1984), who showed that viral or plasmid DNA injected into the liver or spleen of mice was expressed at detectable levels. The DNA was precipitated using calcium phosphate and injected together with hyaluronidase and collagenase. The transfected gene was shown to replicate in the liver of the host animal. Benvenisty and Reshef, Proc. Nat. Acad. Sci. USA, 83:9551–55 (1986) injected calcium phosphate precipitated DNA intraperitoneally into newborn rats and noted gene expression in the livers of the animals 48 hr. after transfection. In 1990, Wolff et al, Science, 247:1456–68 (1990), reported that the direct injection of DNA or RNA expression vectors into the muscle of mice resulted in the detectable expression of the genes for periods for up to 2 months. This technique has been extended by Acsadi et al, New Biologist, 3:71–81 (1991) to include direct injection of naked DNA into rat hearts; the injected genes were expressed in the heart of the animals for up to 25 days. Other genes, including the gene for dystrophin have been injected into the muscle of mice using this technique. This procedure forms the base of a broad approach for the generation of immune response in an animal by the administration of a gene by direct injection into the target tissue. The gene is transiently expressed, producing a specific antigen (see Donnelly et al, The Immunologist, 21, pp. 20–26 (1994) for a recent review). However, the DNA used in these experiments has not been modified or compacted to improve its survival in the cell, its uptake into the nucleus or its rate of transcription in the nucleus of the target cells.

Behavior of DNA in Solution. DNA is a rod-like molecule in solution, due to the highly negatively charged nature of its phosphate backbone, and its basic structure can be perturbed by modification of the hydration shell associated with the helix. This perturbation can be brought about in two ways; first, a change in the degree of charge neutralization of the DNA molecules resulting in extensive compaction and eventually in the separation of the DNA phase (precipitation) in the form of compact structures, and second, a change in the dielectric constant of the DNA helix leading to the formation of compact structures. These perturbations result in a change in the conformation of the DNA molecule permitting the flexible polymer to bend and become compacted, markedly altering the hydrodynamic properties of the DNA molecule. The resultant structures are thought to be of similar nature to that which the DNA assumes in the chromosomes of higher eukaryotes and inside viral capsids.

DNA in the nucleus of a higher eukaryote is intimately associated with basic nuclear proteins (i.e. the histones and protamines) with a high content in lysine and arginine (histones) or arginine (protamines). The complex of DNA with these basic proteins is responsible for the control of DNA compaction that occurs upon chromosome formation and is thought to play a role in the regulation of gene expression. DNA compaction, which occurs physiologically in viruses, bacteria and eukaryote nuclei, has been extremely difficult to reproduce in the laboratory. Theoretically, due to the highly negatively charged nature of the DNA backbone, a change in the degree of charge neutralization of the DNA results in extensive compaction and eventually in the separation of the DNA phase (precipitation) in the form of compact structures. However, the behavior of DNA-polycation complexes in solution is dependent on the method for complexing DNA with the poly caionic protein.

Studies by Olins, Olins and von Hipple (J. Mol. Bio. 24, 157–176, 1967) using cationic homopolypeptides as models for nucleoprotein complex formation presented evidence for the formation of specific complexes of DNA with cationic polypeptides (poly-L-lysine, poly-L-arginine and poly-L-ornithine) after "annealing" of both components in solution. This procedure involved step-down dialysis from NaCl concentrations of 2M to 0.010M.

Several comments may be made on this study. First, thermal denaturation of complexes formed by the addition of polycation to DNA established that polycation binding to DNA occurred in every case studied, and resulted in the stabilization of the double stranded structure of DNA. It is important to note that this system differs from that in which a change in the dielectric constant (i.e. alcohol dehydration) results in DNA collapse with no change in the thermal denaturation characteristics of the DNA. Second, spectrophotometric studies indicated that the absorbance maxima at 260 nm was shifted slightly to the red with a progressive increase in turbidity at wavelengths greater than 300 nm (a region in which neither the polycation nor the DNA show any absorbance). These characteristics were thought to indicate that a small conformational change, occurring possibly through the interaction between DNA and the polypeptide, was being detected by an anomalous absorption spectra. Third, the complexes formed by the addition of basic polypeptides to DNA resulted in molecular aggregation and the formation of precipitates.

Optical Rotatory Dispersion and Circular Dichroism were applied to the study of the interaction between basic homopolypeptides and DNA in solution. Shapiro, Leng and Felsenfeld (Biochemistry, 8:3219–3232, 1969) elucidated the changes in secondary structure associated with the formation of DNA complexes by examining their optical rotation, using a protocol for complexing polylysine to DNA essentially different to that of annealing both components in a step-down salt dialysis. they directly mixed polylysine and DNA in a high salt solvent (1M NaCl), which resulted in the formation of "soluble" complex. A high degree of turbidity is associated with the complex in solution, indicating aggregation of the components. Aggregation was occurring in the samples used to determine the optical rotatory properties of the complex since the circular dichroism spectra approached the baseline asymptotically at wavelengths in the range of 320 to 360 nm. The anomalous spectrum was always associated with turbidity. We have inferred that the optical activity changes arose from the formation of higher order molecular complexes upon aggregation.

DNA complexes obtained under the experimental conditions described above have a median sedimentation coefficient varying between about 5000 and 10000 units. The average particle had a diameter of 340 nm, (calculated using information provided by light scattering) and the particles had an average dry mass corresponding to about 70 nucleic acid/polypeptide molecular units. The information provided by these studies, while not absolutely quantitative, delineates the structural changes that DNA undergoes after binding to a basic polypeptide.

Several aspects of the structure of DNA-polybase complexes in solution have been investigated (Haynes, Garrett and Gratzer, Biochemistry, 9:4410–4416, 1970). Electron microscopy confirmed the ordered nature of the complexes described by Shapiro et al; DNA structures formed as doughnut-shaped toroids, with an external diameter of 300 nm. The C. D. and electron microscopic features of DNA-poly-base complexes correspond to structural factors residing in the Watson-Crick DNA helix, since single-stranded polynucleotides-polybase complexes i.e. rRNA, po.y(A), poly (U), etc.) do not show anomalous optical activity. Also, ordered structures can be detected in the electron microscope. In order to clarify whether a change in base tilt and/or helix pitch could be observed in the complexes, the X-ray diffraction pattern of the complexes was determined. The double helix is in the normal B form obtained for free DNA in aqueous solutions; no obvious transitions were found to the C or A forms of DNA, suggesting the existence of a different structural form when the DNA is complexed to basic polypeptides in solution. There is also an association of DNA-polybase complexes which involves direct pairing of charges, as shown by the progressive displacement of counter-ions in DNA-polylysine complexes as the salt concentration is decreased. Any strong interaction of the charged amino group with a base is therefore very improbable. Thus, the anomalous rotatory strength of DNA in solution arises from chiral packing, the kind of phenomenon associated with the appearance of a large periodicity in the asymmetric packing of molecules in the same plane.

Lerman et al., Proc. Nat. Acad. Sci. USA, 68:1986–90 (1971) report that when a dilute solution of phage DNA is mixed with a sufficiently high concentration of a simple neutral polymer (polyethylene oxide) in the presence of high NaCl (a simulated intracellular environment), the phage DNA molecules collapse into particles approaching the compactness of the contents of phage heads. The structure of DNA complexes was. resolved by Gosule and Schellman (Nature 259: 333–335, 1976). Their publication along with a more detailed report (Gosule, L., Chattoraj. D. K., and Schellman. J., Advances in Polyamine Research 1: 201–215, 1978), showed that the compaction of DNA (in a very dilute solution) by basic polypeptides (spermine and spermidine), under the conditions first described by Li, Biopolymers, 12:287 (1973), resulted in toroid structures. The complexes generated by Gosule and Schellman had an unimolecular structure consisting of a single DNA unit of phage DNA compacted to a maximum radius of about 50 nm. The authors note that polyamines are known to exist in bacterial cells. DNA compaction is also discussed by Laemmli, PNAS 72:4288–92 (1975) and Post and Zimm, Biopolymers, 21:2123–32 (1982).

All references cited in this specification are hereby incorporated by reference. No admission is made that any reference constitutes prior art. The discussion of the references states what their authors assert and applicants reserve the right to challenge the accuracy and pertinency of the cited documents.

SUMMARY OF THE INVENTION

The present invention relates to a method for compacting nucleic acids, substantially without aggregation, and to therapeutic use of the compacted DNA. The compacted nucleic acid can be efficiently delivered across the membrane of a living cell, especially a cell in a multicellular organism. DNA condensed into small particles may be more suitable for nuclear translocation through the nuclear pores and may be protected against nucleases. When the nucleic acid includes an expressible gene, that gene can be expressed in the cell.

In some embodiments, a tissue-specific carrier molecule is prepared, which is a bifunctional molecule having a nucleic acid-binding moiety and a target tissue-binding moiety. The nucleic acid is then compacted at high concentrations with the carrier molecule at a critical salt concentration. The nucleic acid-loaded carrier molecule is then administered to the organism. Each carrier molecule bears a single nucleic acid molecule.

In other embodiments, a target tissue-binding carrier molecule is not used. However, the nucleic acid is still compacted by complexing with a carrier molecule comprising a nucleic acid binding moiety which reduces interactions between the nucleic acid and the solvent. The compacted complexes are administered to the organism.

The appended claims are hereby incorporated by reference into this description as a recitation of preferred embodiments of the invention.

BRIEF DESCRIPTION OF THE DRAWINGS

FIGS. 1A–1J - Physical characterization of the galactose-poly-L-lysine/DNA complexes.

FIG. 1A shows CD spectra associated with normal DNA in solution and with certain poly-L-lysine/DNA complexes. Sixty micro grams of RNA-free CMV-β-galactosidase plasmid (dissolved in TE buffer, pH 8), 150 µl of 700 mM NaCl were vortexed at medium speed in a VIBRAX apparatus (IKA-VIBRAX-VXR). Nineteen micrograms of α-galactopyranosyl-phenyl isothiocyanate/poly-L-lysine biconjugate in 150 µl of 700 mM NaCl were added dropwise to the vortexing solution of DNA. The slow addition of the polycation results in the formation of a turbid solution which is dissolved by the slow, stepwise addition of 3 µl aliquots of 5M NaCl. The disappearance of the turbidity was monitored by eye and the solutions of DNA/poly-L-lysine complexes were investigated by CD. At this point (0.97M NaCl), the CD spectrum was that characteristic of aggregated DNA. Further addition of 2 µl aliquots of 5M NaCl (resulting in a concentration of 1.031M NaCl) yielded the CD spectrum expected for a condensed (or a relaxed) DNA complex. The CD spectrum of uncomplexed double stranded DNA at 1M NaCl was also taken. The spectra were obtained using a JASCO-600 spectropolarimeter with a 0.1 cm cuvette. The spectrum of the buffer was subtracted in each case.

FIGS. 1B–1G are electronic micrographs (EM). 1B–1D, 1F and 1G are taken at 300,000×. The bar in 1D represents 33.3 nm. FIG. 1E was taken at 600,000×, and the bar is 16.6 nm long. Uranyl acetate staining was performed as previously described. (Ennever, et al., *Biochem. Biophys. Acta*, 826:67 (1985)). Briefly, the grid was subjected to glow discharge prior to staining. A drop of DNA solution was added to the grid, blotted and stained using 0.04% uranyl acetate.

For the EM studies shown in FIGS. 1B–1F, 60 µg of PEPCK-hFIX plasmid DNA (dissolved in TE buffer, pH 8), in 150 µl of 700 mM NaCl were vortexed at medium speed in a VIBRAX apparatus (IKA-VIBRAX-VXR). Nineteen micrograms of α-galactopyranosyl-phenyl isothiocyanate/poly-L-lysine bioconjugate in 150 µl of 700 mM NaCl were added dropwise to the vortexing solution of DNA. The slow addition of the polycation results in the formation of a turbid solution which is dissolved by the slow, stepwise addition of 3 µl aliquots of 5M NaCl. The disappearance of the turbidity was monitored by eye and the solution of DNA/poly-L-lysine complexes was investigated by EM (FIG. 1C). Further addition of 2 µl aliquots of 5M NaCl resulted in structural changes as shown in FIGS. 1D and 1E.

Figure 1A:
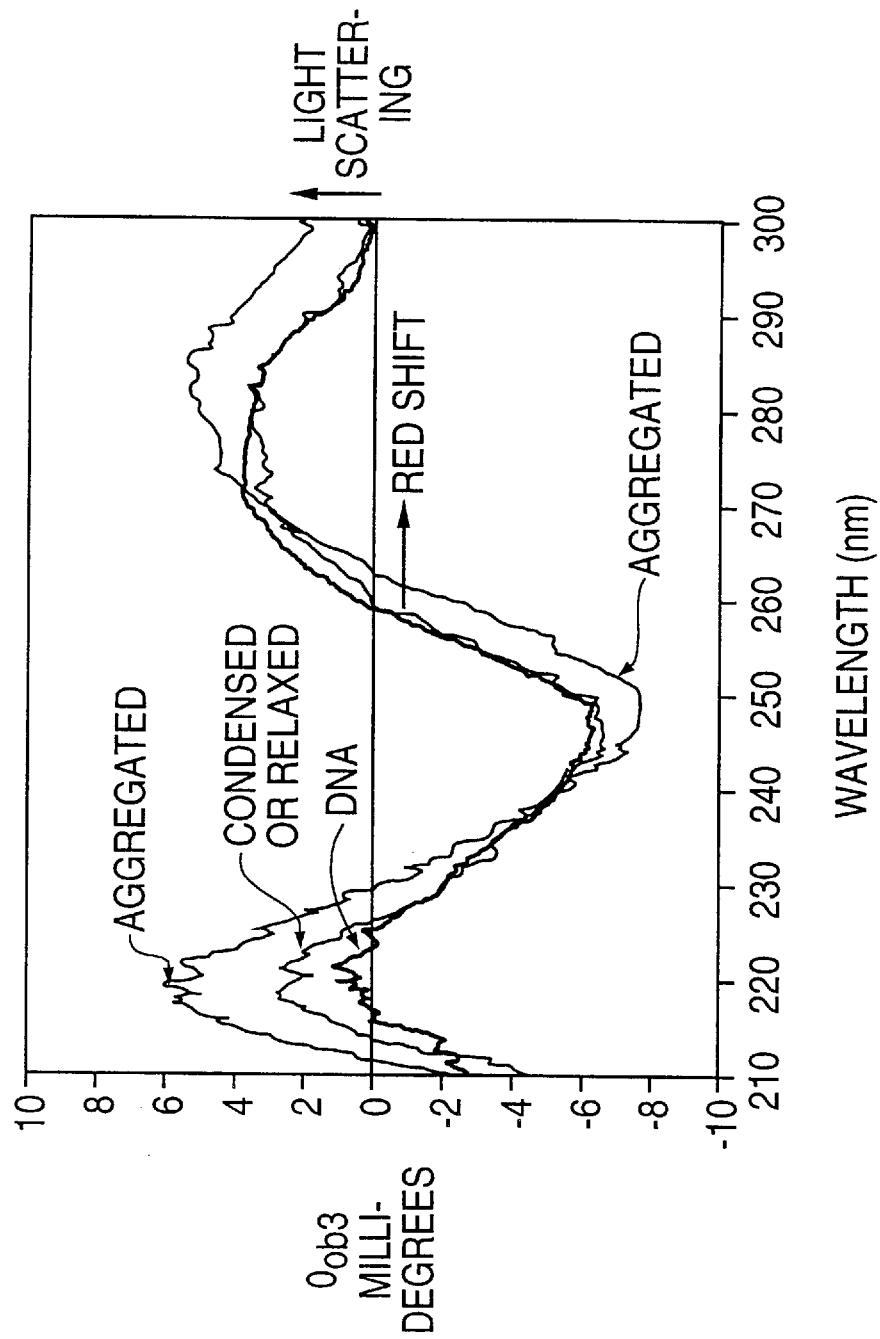
Figure 1F:
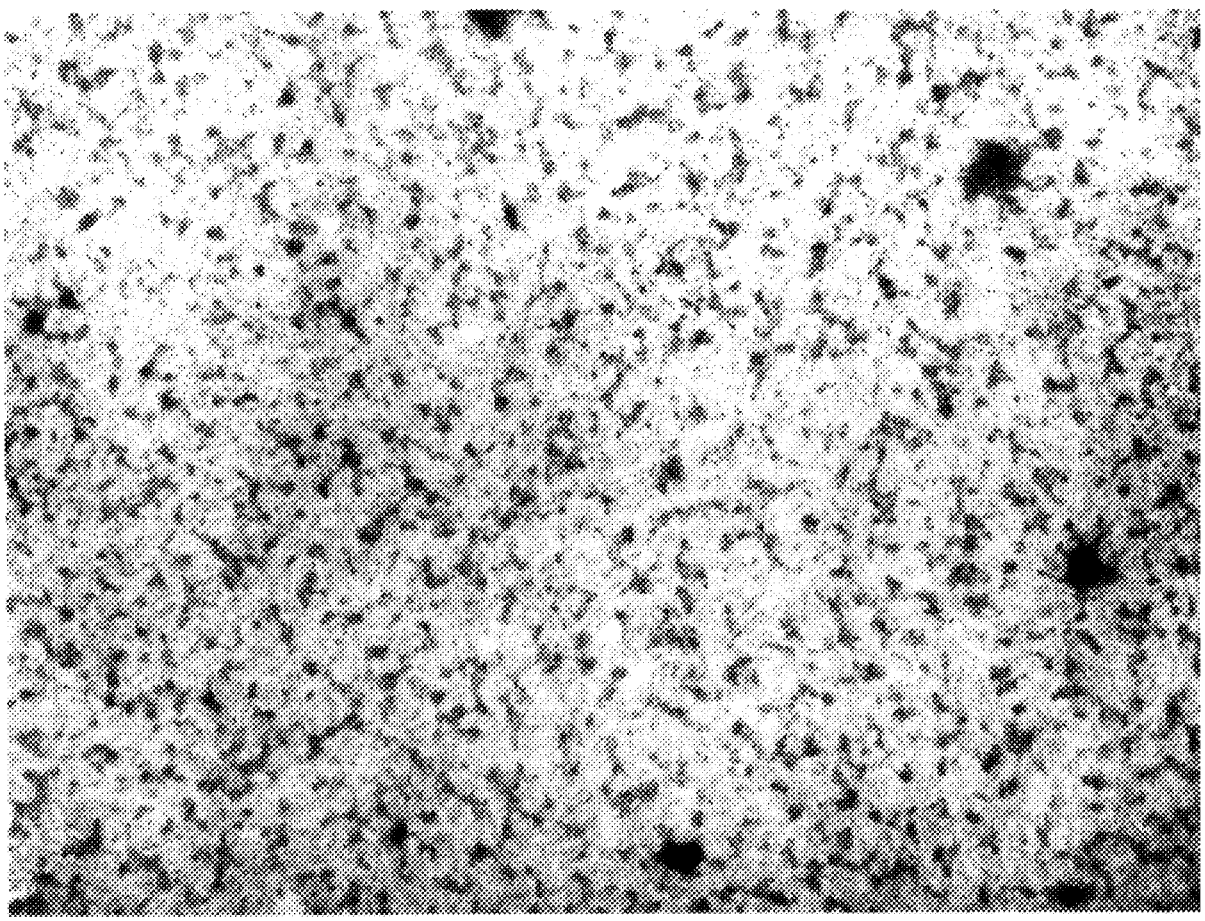

FIG. 1B is an EM of uncomplexed DNA (1 ug/ml at 1M NaCl). FIG. 1C depicts a DNA complex at a suboptimal concentration of NaCl (760 mM). The DNA is in the aggregated state; clusters of unimolecular toroids are visible. In FIG. 1D the DNA complex is at an optimal concentration of NaCl for the complex in question (968 mM). The DNA is properly condensed; only individual toroids can be seen. For FIG. 1E, four complexes of DNA from FIG. 1D were selected and printed at higher magnification. In FIG. 1F, we see a DNA complex, at a concentration of 1.068M NaCl, which is above optimal for condensation of this complex. The DNA is in the relaxed state. Note the branched unimolecular toroids in which a nucleus of condensation is visible and the rod-like DNA fibers.

Differences in concentration of NaCl required for aggregated, condensed, and relaxed states in the above experiments represent DNA or polycation specific differences.

In a third experiment, complexes of CMV-β-galactosidase and galactosylated poly-L-lysine were formed essentially as in Wu et al. Briefly, plasmid DNA and galactosylated poly-L-lysine were combined in 3M NaCl. The samples were incubated for 1 hour at room temperature, then dialyzed against 0.15M NaCl for 16 hr through membranes with a 3,500-dalton molecular mass limit. On visual inspection, no precipitates were present in the dialysate.

Figure 1G:
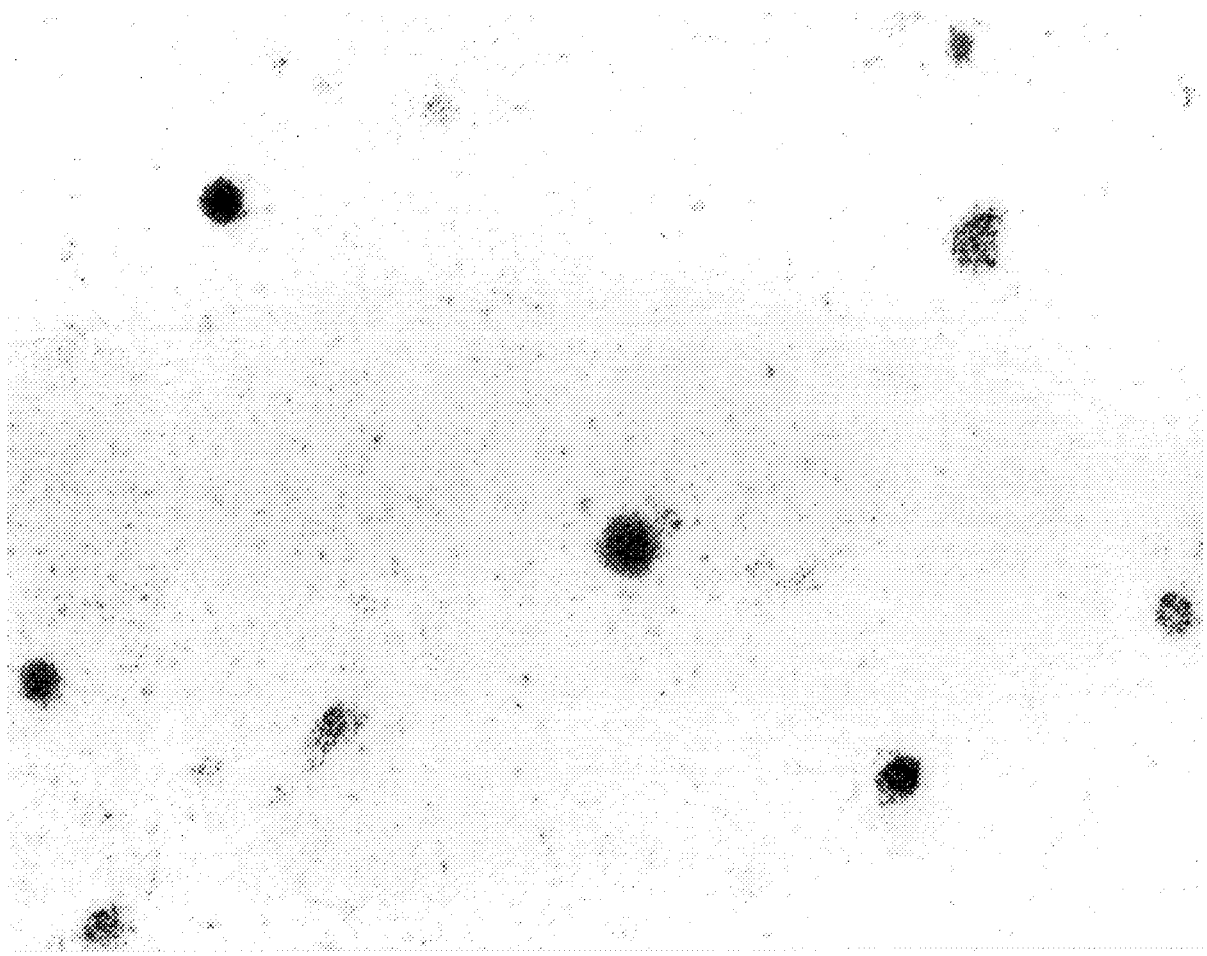

FIG. 1G is an electron micrograph of the resulting DNA complex, which is in the multimolecular aggregated state. Note that the toroids here are larger than in 1C or 1D (the scale is the same). FIG. 1H shows the CD spectrum from 240 to 300 nm for uncomplexed DNA and for aggregated multimolecular DNA/poly-L-Lys complexes, so as to highlight the inversion of the normal DNA spectrum maximum at 269 nm. This inversion is characteristic of multimolecular aggregation.

In another experiment, sixty micrograms of PEPCK-hFIX plasmid DNA (dissolved in TE buffer, pH 8), in 150 µl of 200 mM NaCl were vortexed at medium speed in a VIBRAX apparatus (IKA-VIBRAX-VXR). Nineteen micrograms of α-galactopyranosyl-phenyl isothiocyanate/poly-L-lysine biconjugate in 150 µl of 200 mM NaCl were added dropwise to the vortexing solution of DNA. The addition of the polycation resulted in the formation of precipitates on visual inspection.

Figure 1I:
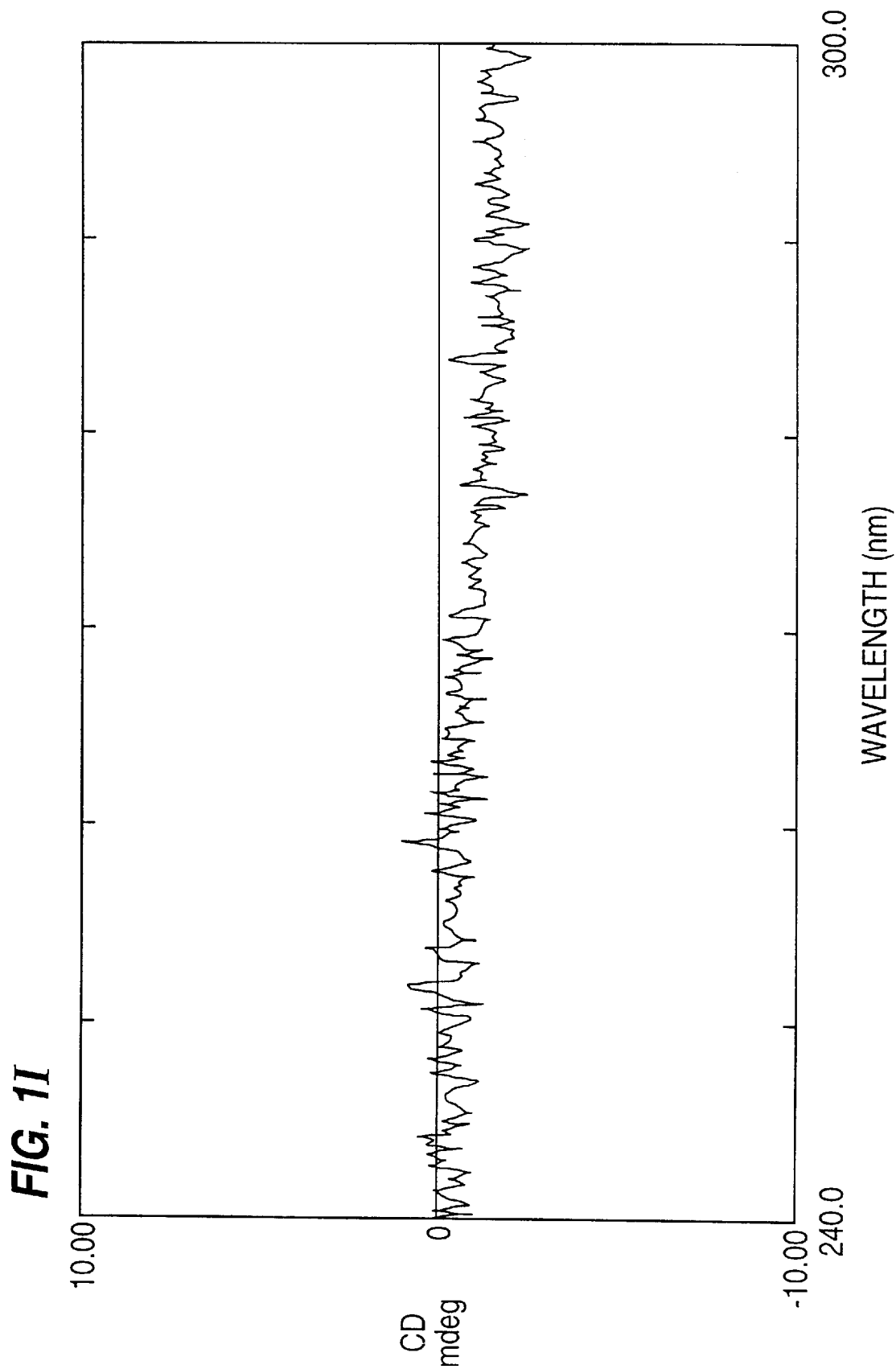
Figure 1J:
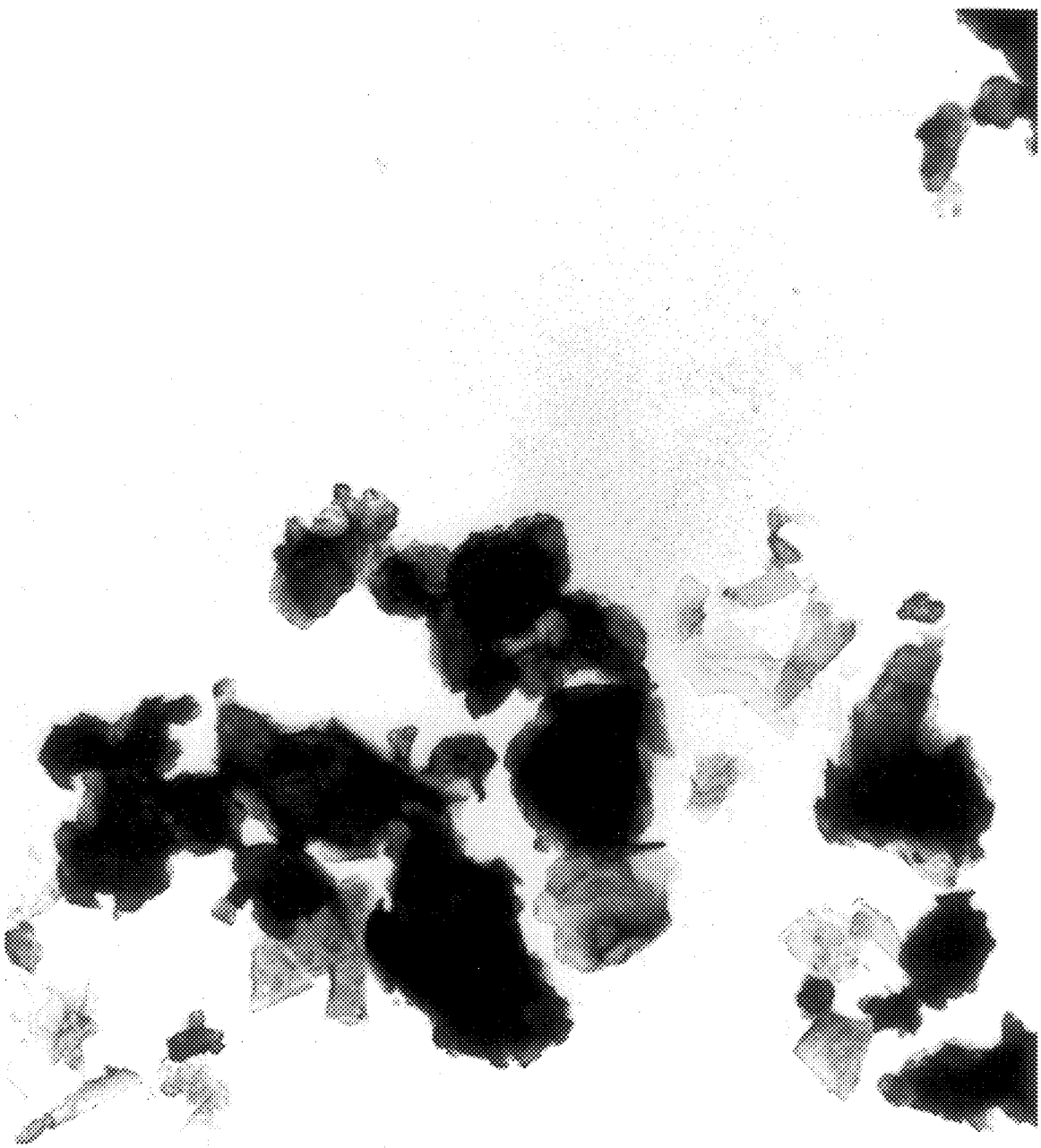

FIG. 1I is a CD spectrum, given by a precipitated DNA complex. It is essentially flat from 240 to 300 nm. FIG. 1J is an electron micrograph of the precipitated DNA.

Figure 2A:
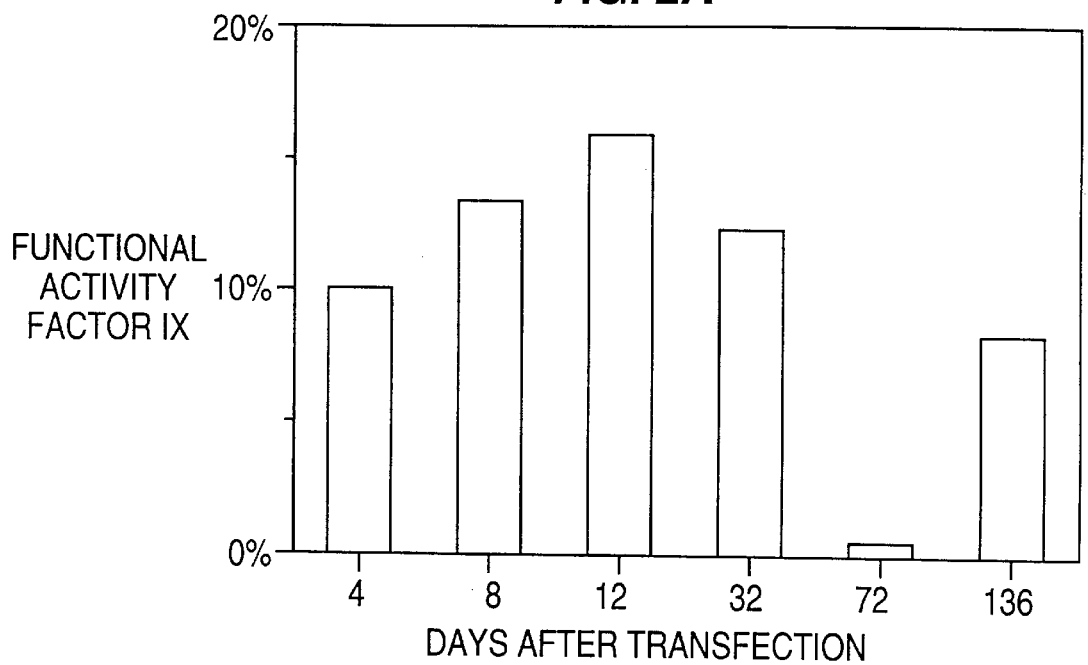
Figure 2B:
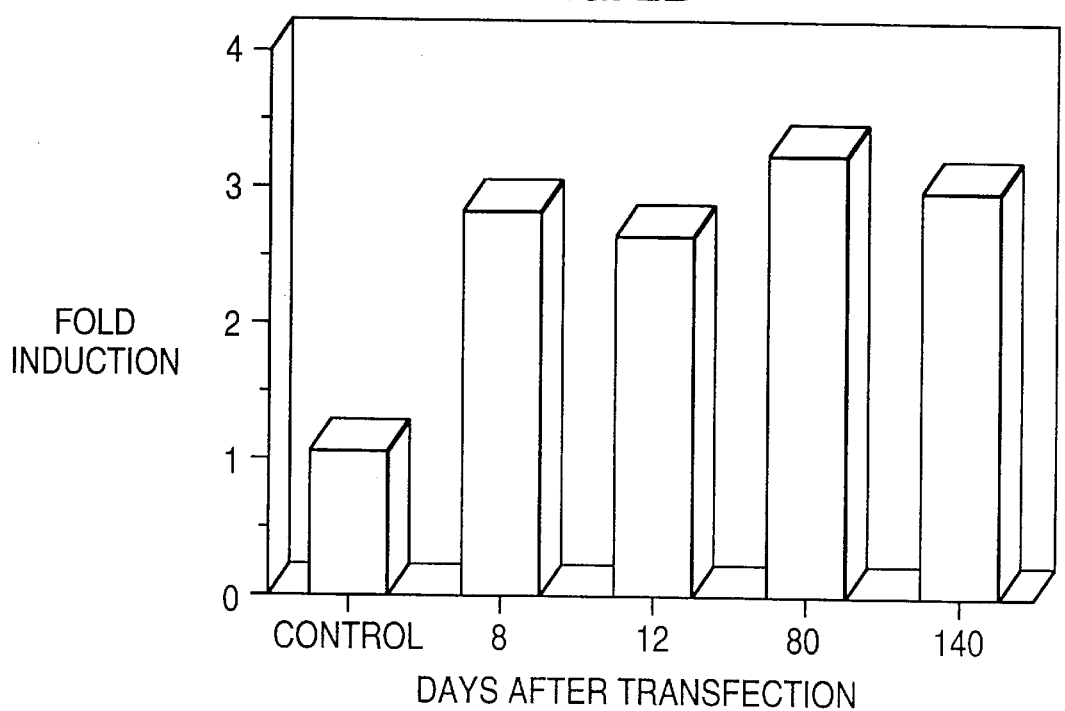

FIGS. 2A and 2B - Functional relevance and specificity of the gene transfer system. (FIG. 2A) The relative concentration of human factor IX in the blood of animals treated with the DNA complex was evaluated by measuring the procoagulant activity of human factor IX. A modification of the one stage, kaolin-activated, partial thromboplastin time with factor IX-deficient human plasma was used. Blood samples were obtained from experimental animals by venipuncture. One fiftieth volume of 500 mM sodium citrate, pH 5.0, was added to prevent coagulation, and the plasma was stored at −20° C. The samples were assayed in duplicate, and their activity was compared to the functional activity of pooled plasma from 24 normal adult human males. In all calculations, one unit of factor IX activity in one ml of normal human plasma is equivalent to 100% functional activity or approximately 3 µg of factor IX per ml. Background human factor IX activity in the rat plasma was subtracted prior to graphic representation. (FIG. 2B) Transfected animals were fed a carbohydrate-free/high protein diet for one week. Blood samples were taken at the initiation of the treatment and after one week on the diet and analyzed by Western blot hybridization. The animals at 8 and 12 days were compared with transfected rats fed a standard chow diet. The data were obtained by densitometric analysis of Western blot photographic films and indicate fold increase in human factor IX protein after the dietary treatment.

Figure 3:
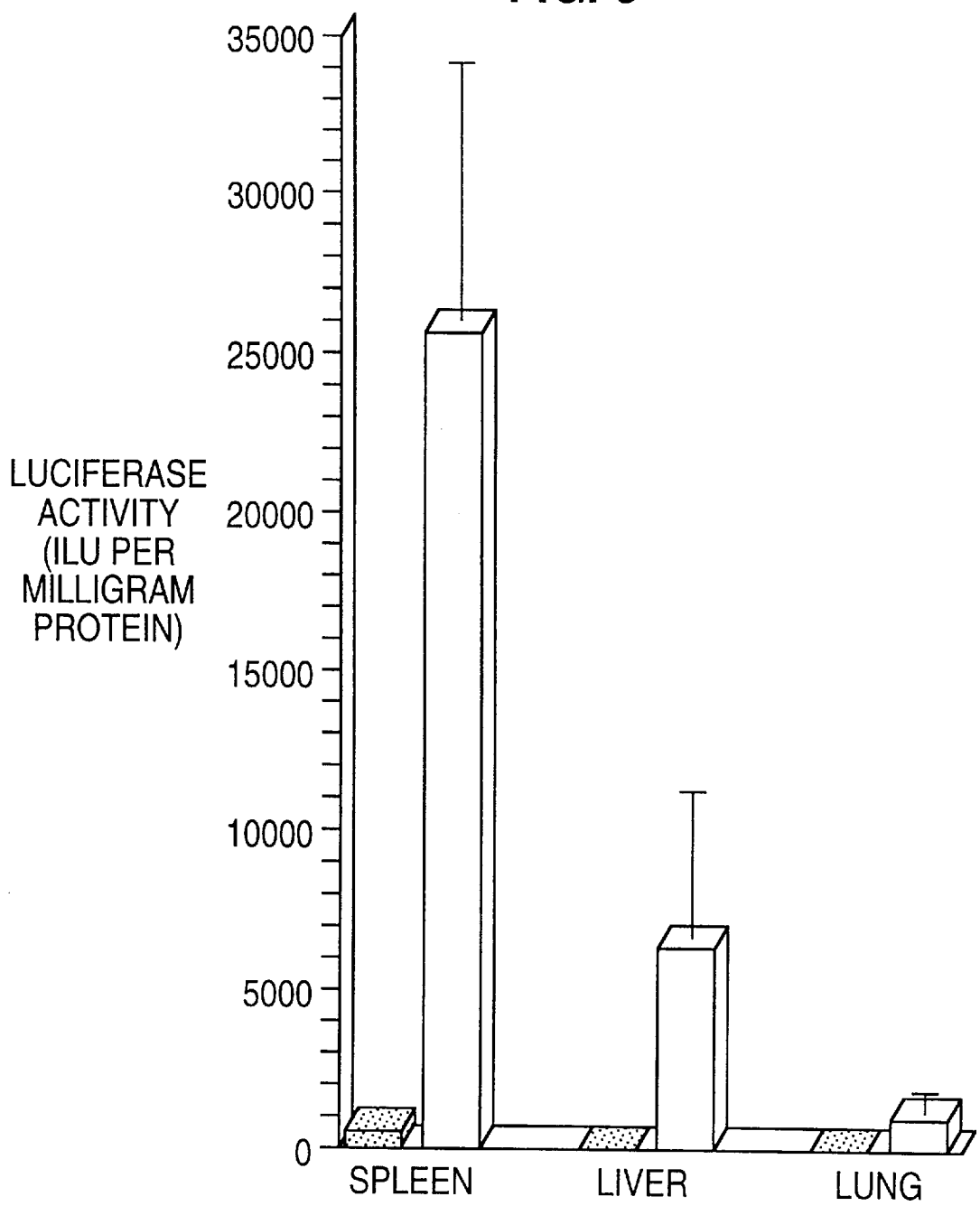

FIG. 3.- Tissue specificity of mannosylated DNA complex in targeting DNA to the macrophages in vivo. Mannosylated poly-L-lysine was conjugated to SV40/luciferase DNA. 300 µg of the DNA complex were introduced into the caudal vena cava of rats. Four days after injection tissue extracts were made and assayed for luciferase activity. The luciferase activity is plotted as Integrated Light Units per milligram of protein extract from spleen, liver and lung. In other tissues no activity was found. Data are expressed as means±standard error of the mean (SEM). The light bars are the non-transfected controls (n=4), and the dark bars, animals transfected with mannosylated poly-L-lysine/DNA complexes (n=5).

Figure 4:
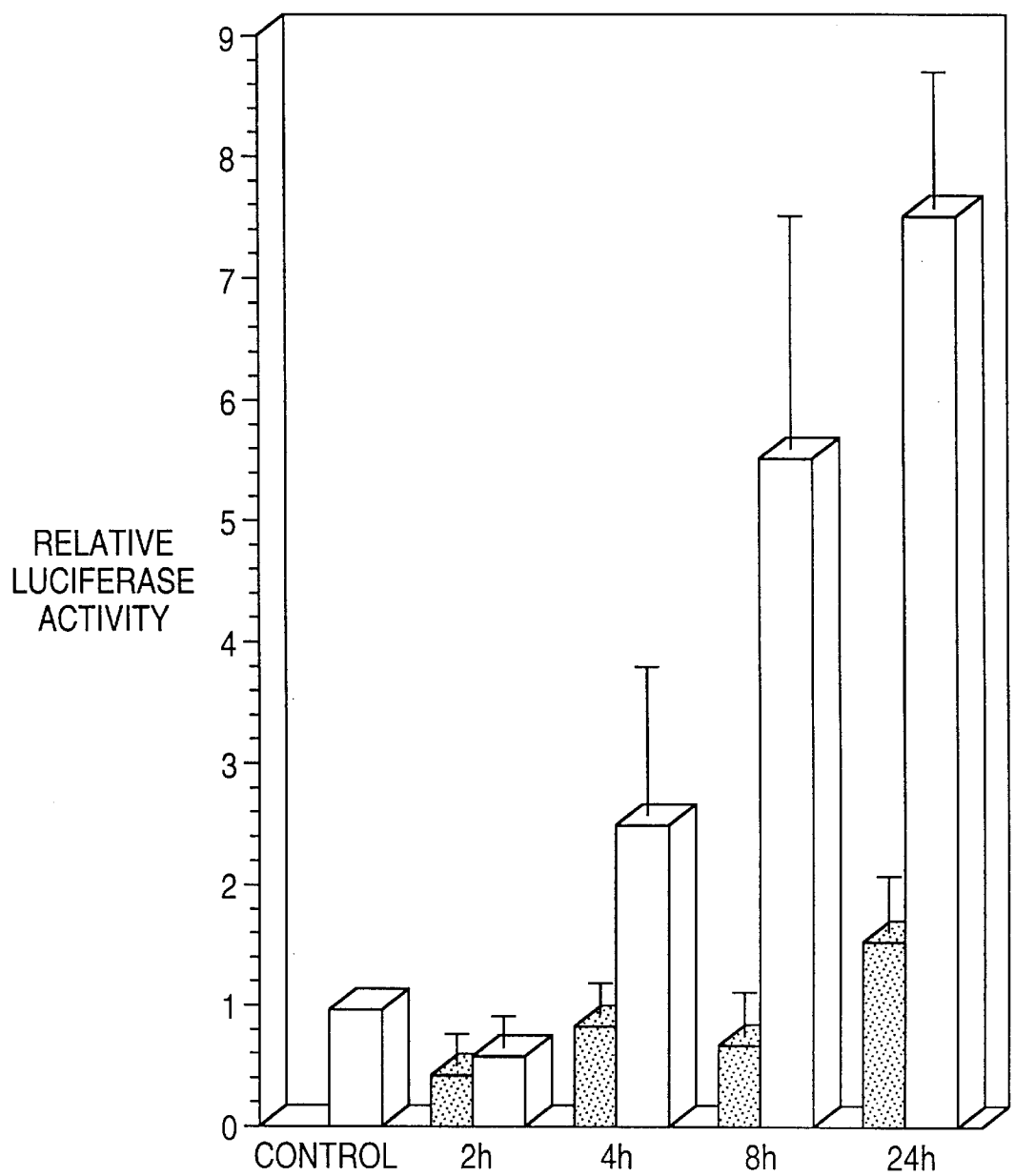

FIG. 4.- Specificity of mannosylated DNA complex in targeting DNA to primary culture of macrophages in vitro. Primary cultures of peritoneal macrophages were transfected with either galactosylated poly-L-lysine (light bars) or mannosylated poly-L-lysine (dark bars) conjugated to a-SV40/luciferase DNA. At the indicated times (2, 4, 8, and 24 hours) cells were washed. Twenty-four hours after transfection, cells were harvested and assayed for luciferase activity. The luciferase activity is plotted as Relative Luciferase Activity after being standardized by the activity found in untransfected controls. Data are expressed as means±standard error of the mean (SEM).

Figure 5:
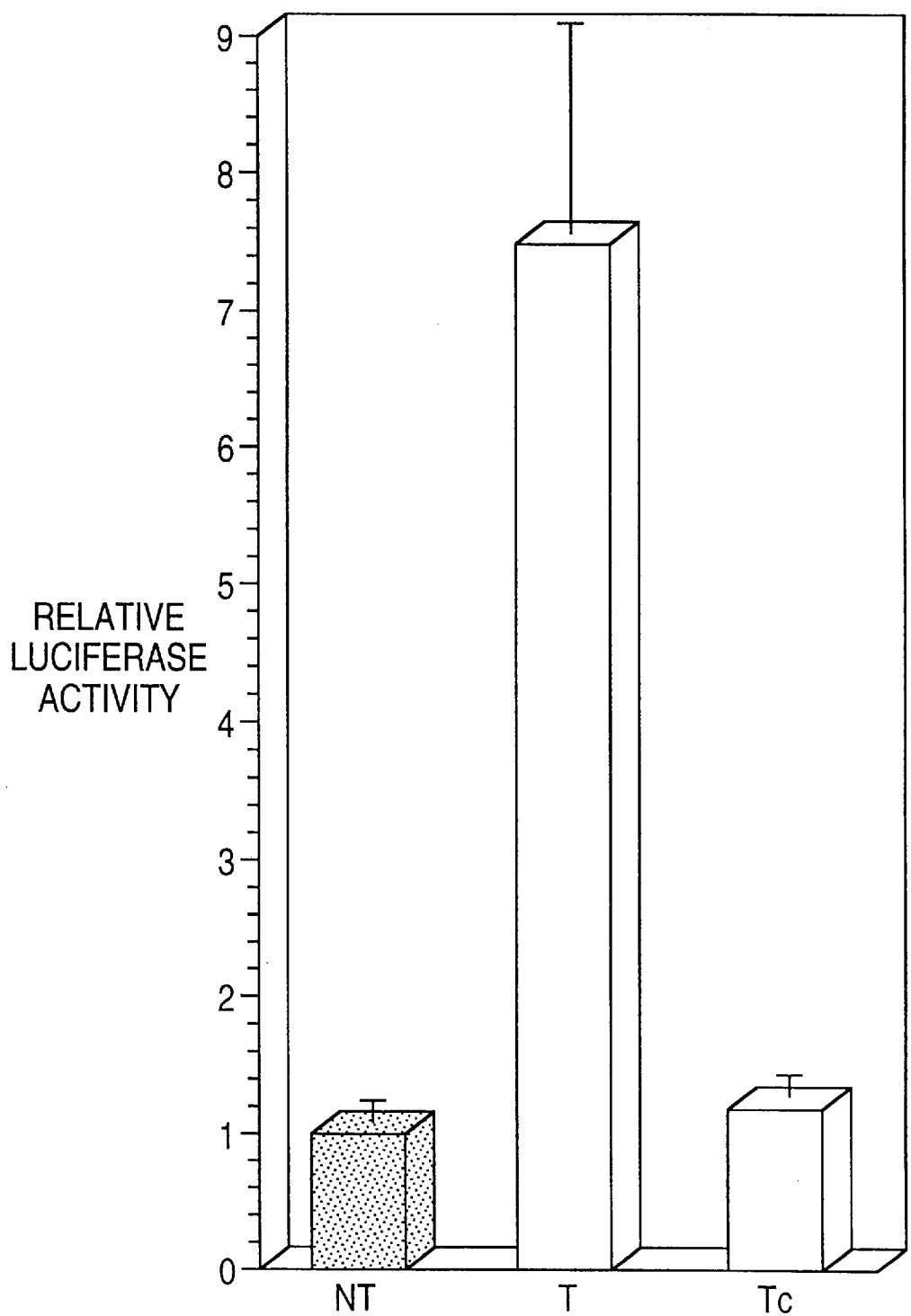

FIG. 5.- Competition between the mannosylated DNA complex and mannosylated bovine serum albumin for binding to the Mannose receptor of macrophages. Primary culture of peritoneal macrophages were transfected with mannosylated poly-L-lysine conjugated to SV40/luciferase DNA (T). Prior to the addition of the DNA complex a 100-fold excess mannosylated bovine serum albumin was added to one set of plates (Tc). Non-transfected controls (NT) were also assayed for luciferase activity 24 hours after transfection. The luciferase activity is plotted as Relative Luciferase Activity after being standardized relative to the activity found in untransfected controls. Data are expressed as means±standard error of the mean (SEM).

Figure 6:
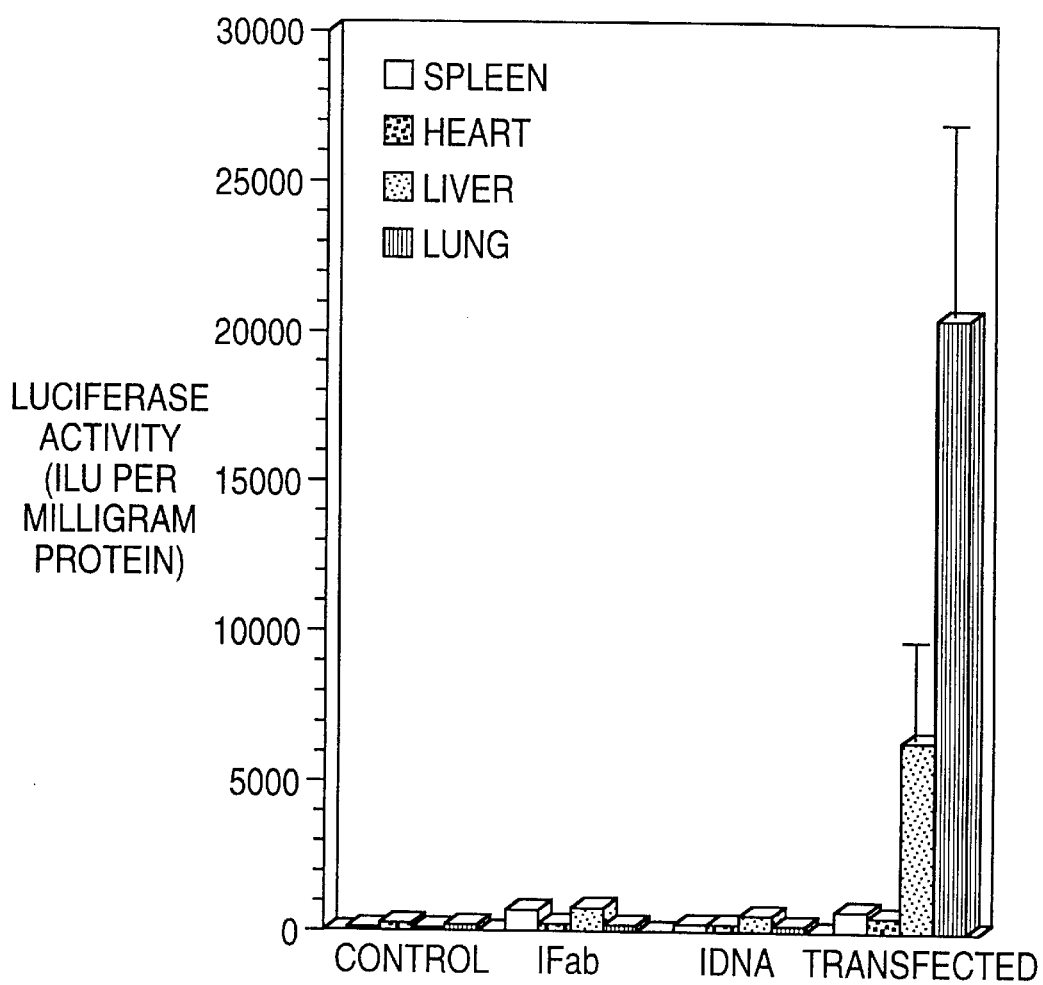

FIG. 6.- In vivo gene transfer using the anti-rat plg-R Fab-poly-L-lysine conjugated DNA complex. Fab-poly-L-lysine was conjugated to SV40/luciferase DNA and introduced into the caudal vena cava of rats (Transfected) (n=3). Untransfected controls (Control) (n=3), animals injected with an Fab-poly-L-lysine-DNA complex containing an Fab fragment obtained from an irrelevant IgF (IFab) (n=3), and animals injected with a DNA complex that does not contain an SV40/Luciferase gene (IDNA) (n=3), were run as controls. Two days after injection tissue extracts were prepared and assayed for luciferase activity. The luciferase activity is plotted as Integrated Light Units per milligram of protein extract. Data are expressed as means±standard error of the mean (SEM).

Figure 7:
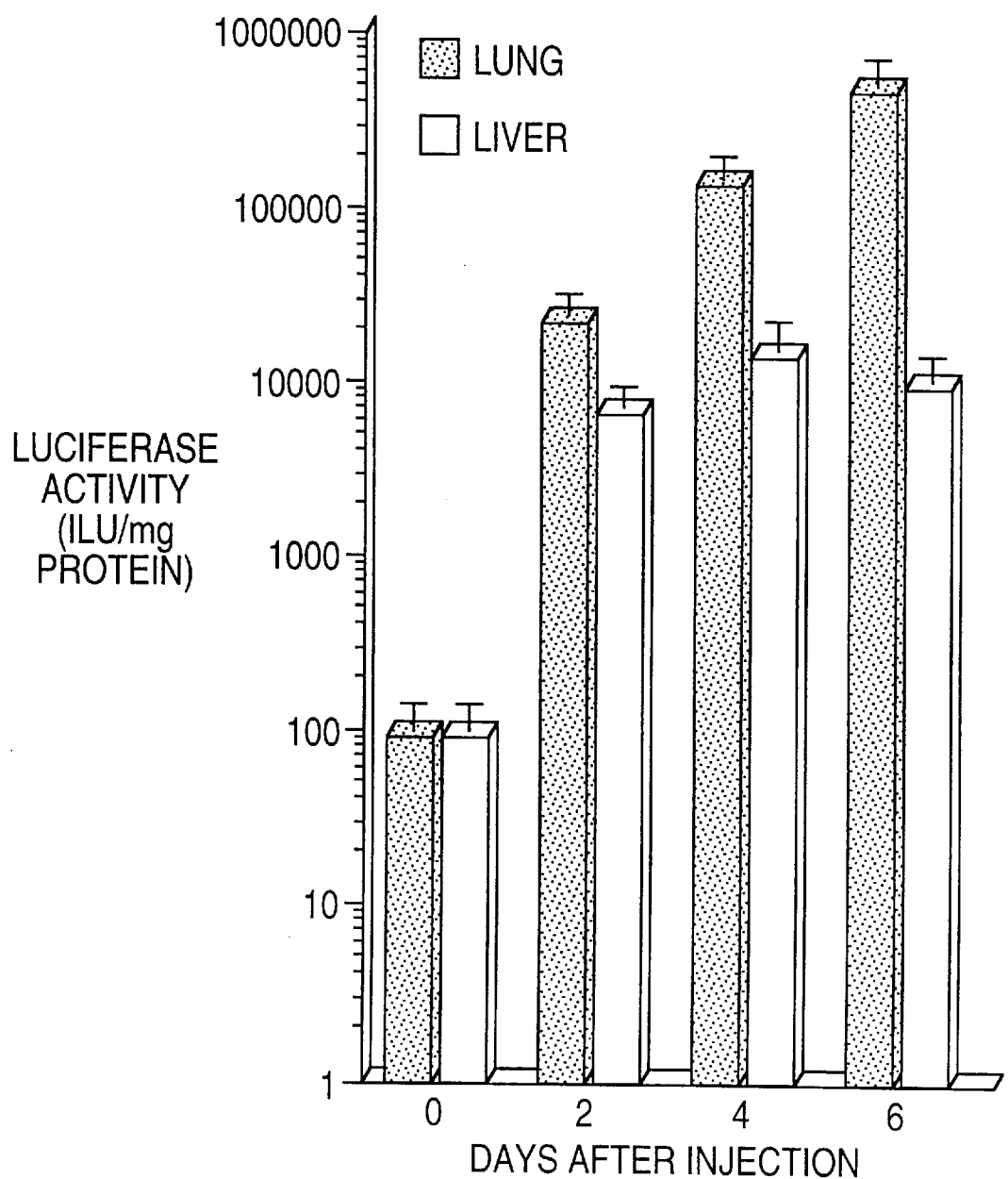

FIG. 7.- Time-course of expression in lung and liver of animals injected using the anti-rat plg-R Fab-poly-L-lysine conjugated DNA complex. Fab-poly-L-lysine was conjugated to SV40/luciferase DNA and introduced into the caudal vena cava of rats (n=9). Rats were killed 2 (n=3), 4 (n=3) and 6(n=3) days after injection. Lung and liver extracts were prepared and assayed for luciferase activity. The luciferase activity is plotted as Integrated Light Units per milligram of protein extract using a logarithmic scale. Data are expressed as means±standard error of the mean (SEM).

Figure 8:
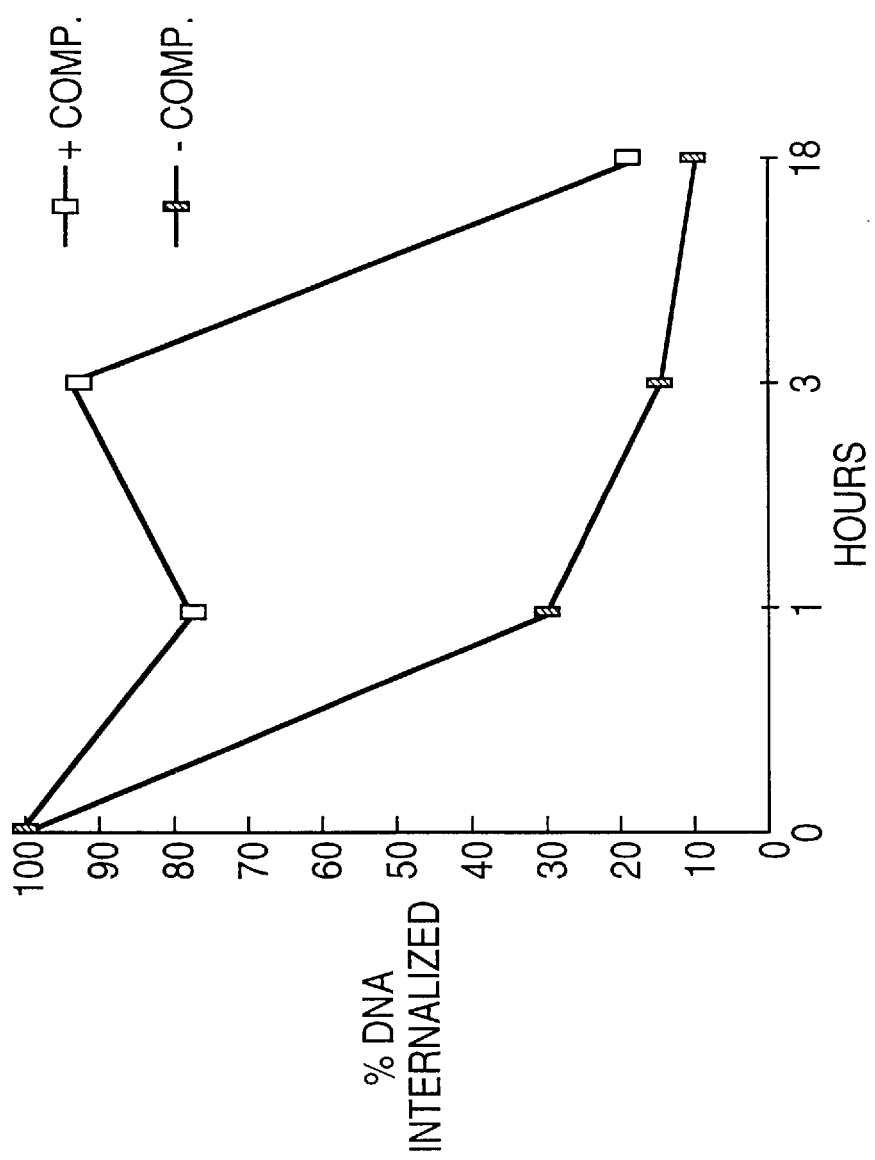

FIG. 8.- Competition between the galactoslyated DNA complex and asialoorosomucoid for binding to the ASGP receptor of HepG2 cells. HepG2 hepatoma cells were transfected with galactosylated poly-L-lysine conjugated to PEPCK-hFIX DNA. Prior to the addition of the DNA complex a 100-fold excess asialoorosomucoid was added to one set of plates (+ Comp.). DNA internalization was monitored by slot-blot hybridization of the culture medium containing the DNA complex. Data are expressed as percentage of DNA internalized by the receptor at different times after transfection.

Figure 9:
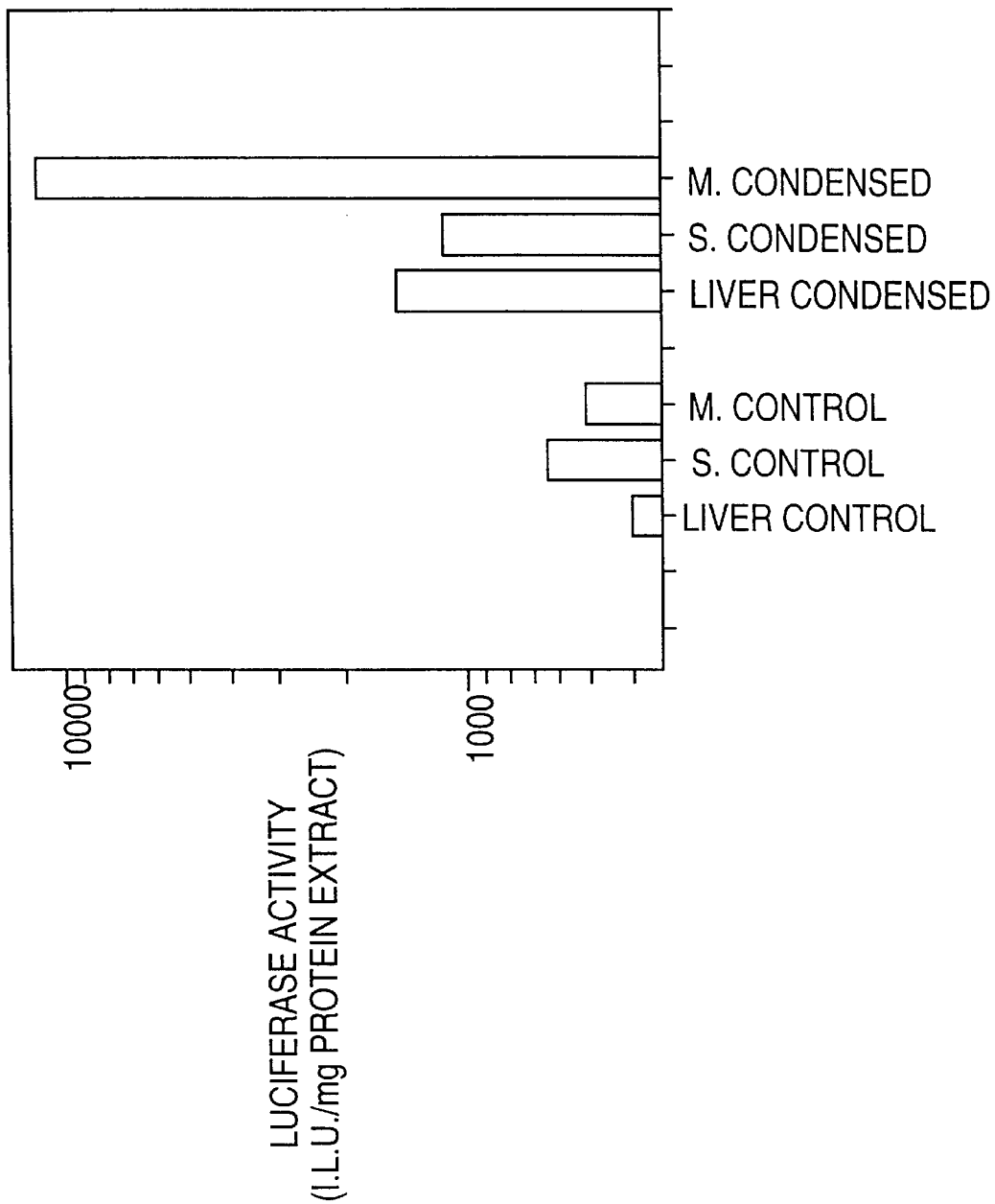

FIG. 9 Direct injection to the muscle and liver of naked DNA vs. condensed DNA. One hundred micrograms of naked DNA encoding SV40-luciferase were injected into the liver and abdominal muscle of two rats. The same amount of the pSV40-luciferase plasmid complexed to poly-L-lysine and condensed as described in Example 1 was injected as well into the liver and abdominal muscle of another two animals. Rats were sacrificed 48 hours post-injection. A piece of liver and abdominal muscle were homogenized in lysis buffer and cell lysates were analyzed for luciferase activity. All luciferase measurements were performed in triplicate, expressed as an average of the values and standardized for total protein. FIG. 9 shows the integrated luciferase units per mg of protein in the two different sets of animals.

Figure 10:
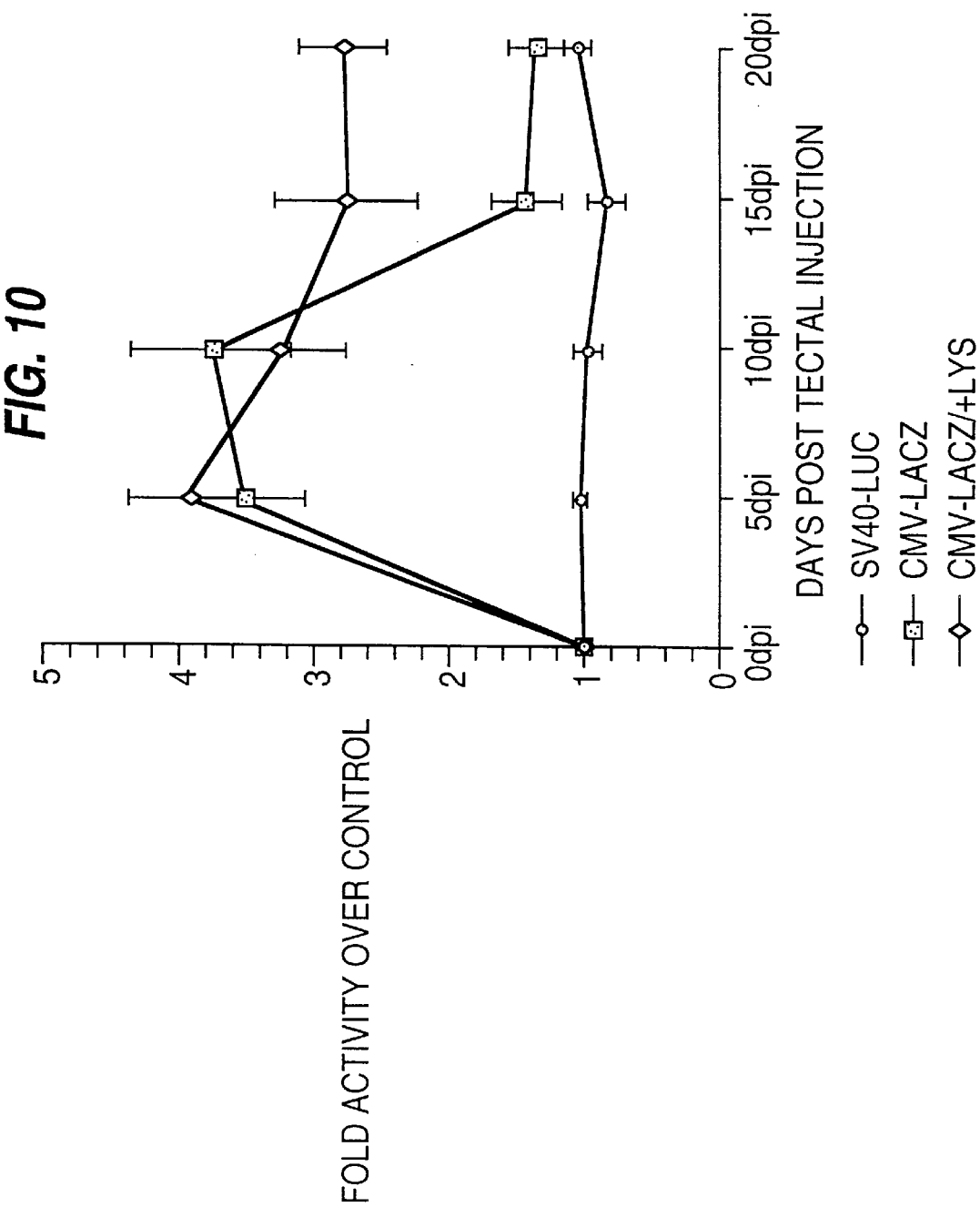

FIG. 10 Direct injection into the brain tectum of naked DNA vs. condensed DNA. Intratectal injections of naked and poly-L-lysine condensed plasmid DNA can achieve high levels of expression in the cell body of the neuron over 20 days. β-galactosidase activity in retinas from rats whose brains were injected into the tectal areas and administered with either naked pCMV-lacZ, or condensed pCMV-lacZ (pCMV-lacZ+lys) at the concentrations shown. When the DNA is not condensed with poly-L-lysine the level of expression returns to background after 10 days post-injection.

Figure 11:
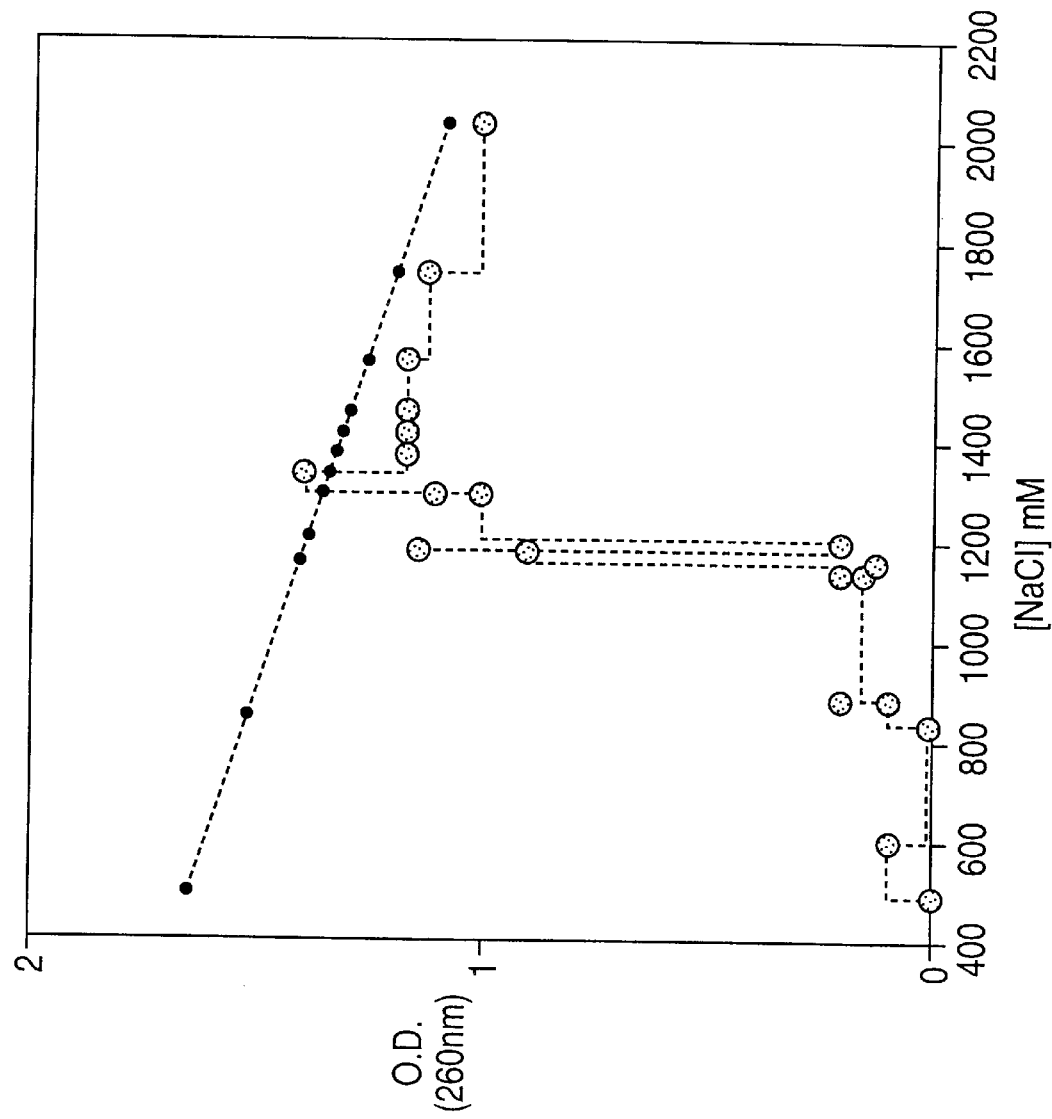

FIG. 11. Changes in the absorbance of the DNA complexes during the condensation process. A plasmid containing the chimeric CMV-hLDL receptor gene was condensed with poly-L-lysine, using the procedure described in detail in Example 1. After the addition of poly-L-lysine the absorbance of the solution at 260 nm was determined. Concentrated NaCl was then added stepwise and the absorbance determined. The expected absorbance for the DNA contained in the complex is indicated by the dotted line. The initial NaCl concentration used in the condensation reaction was 500 mM.

Figure 12:
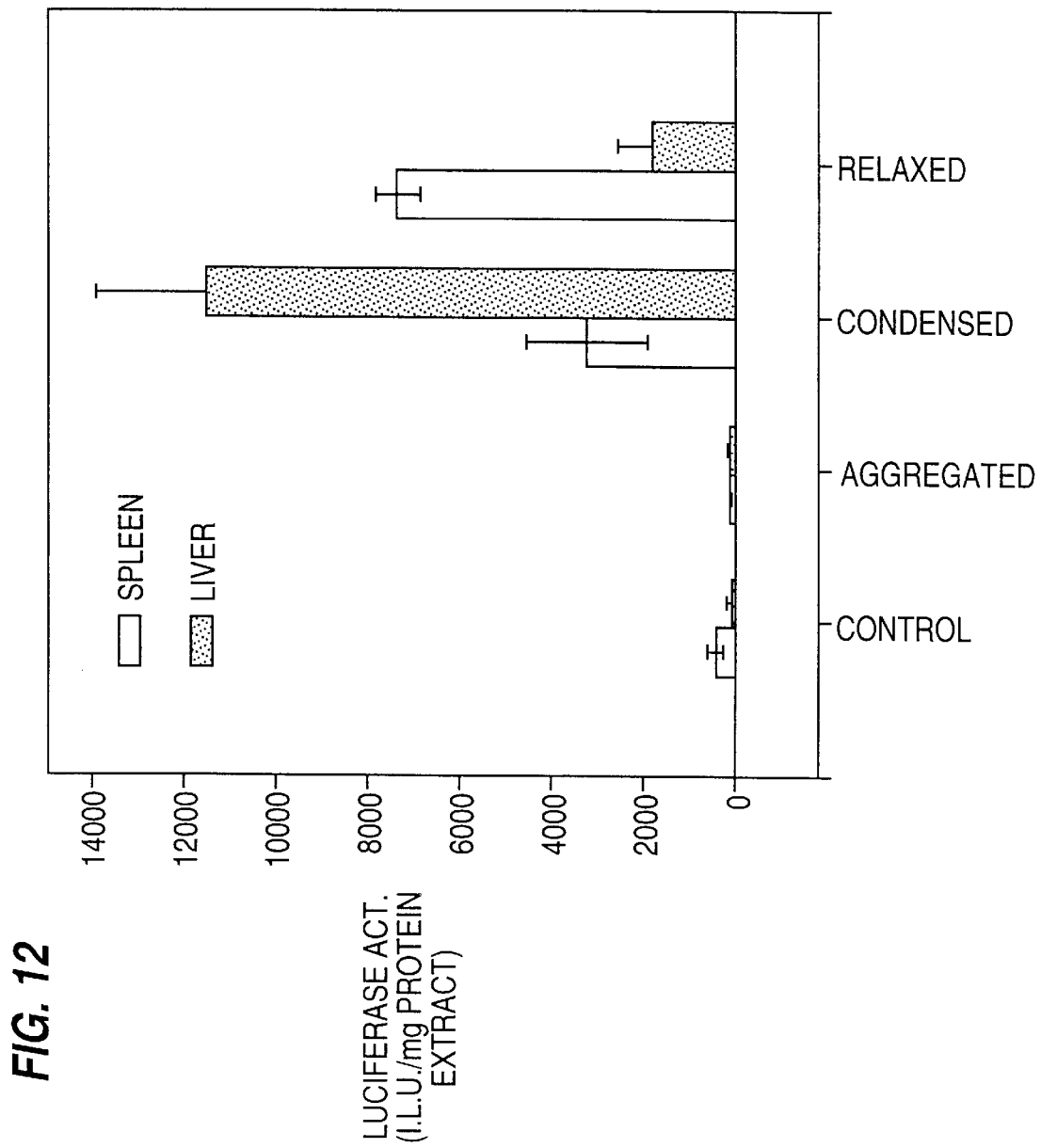

FIG. 12 Relationship between the structure of the DNA complex and its function in adult rats. DNA-galatosylated poly-lysine complexes were prepared which correspond to various states of condensation/aggregation shown in FIG. 1B–1G. The DNA consisted of the SV40 promoter linked to the structural gene for P. pyralis luciferase gene. Rats were injected in the caudal vena cava with 300 µg of the various DNA complexes and the activity of luciferase was determined in extracts from the liver and the spleen 48 hr after injection. Each bar represents the mean±SEM for three rats; control rats were not injected with the DNA complex.

Figure 13:
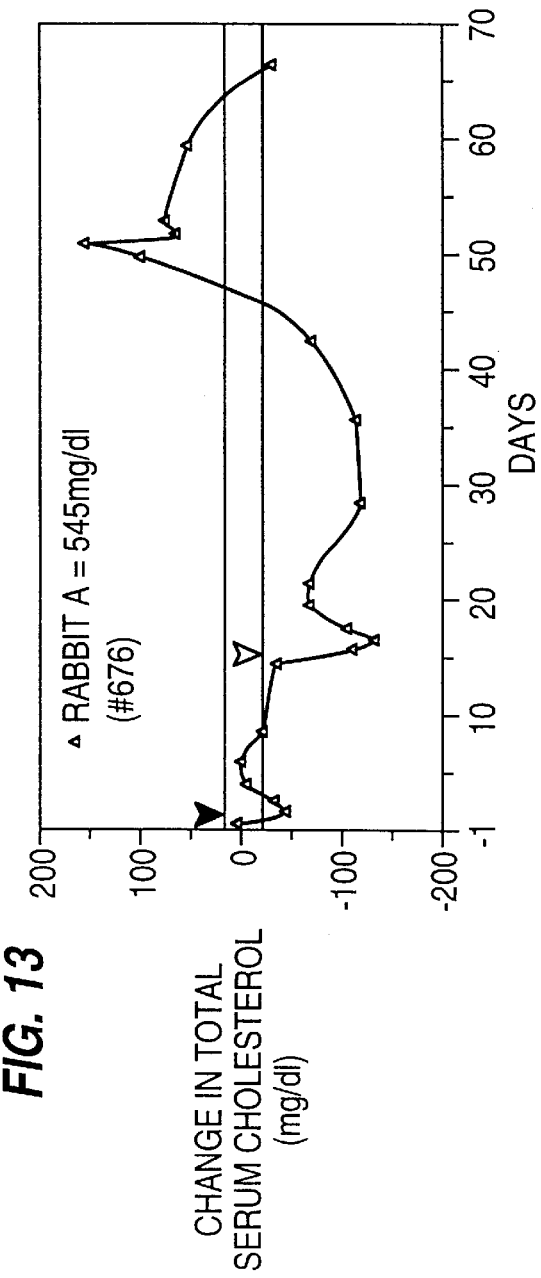

FIG. 13 Introduction of 3 mg of PEPCK-hLDLr in its relaxed (non complexed) vs. condensed form. In order to introduce the DNA complex into the animal, we perform a single injection of 3–10 ml of the DNA-complex solution (~400–900 mM NaCl) into the marginal ear vein of the rabbit. Approximately 1.5 ml of blood was drawn at the times indicated from the ear artery at 4 p.m. The determination of the concentration of serum cholesterol was performed in the Clinical Laboratory of University Hospitals of Cleveland from 300 μl of serum. The administration of a DNA complex solution containing 3 mg of the pPEPCK-hLDLR plasmid in a relaxed state to rabbit #676 did not result in a significant decrease (first arrow) in total serum cholesterol levels. A second injection of DNA complexes appropriately condensed containing 3 mg of the same DNA (second arrow) caused a 20% reduction of the levels of cholesterol in the blood. Four weeks after this second administration, cholesterol returned to approximately pre-treatment levels, reaching a peak at about 35 days.

Figure 14:
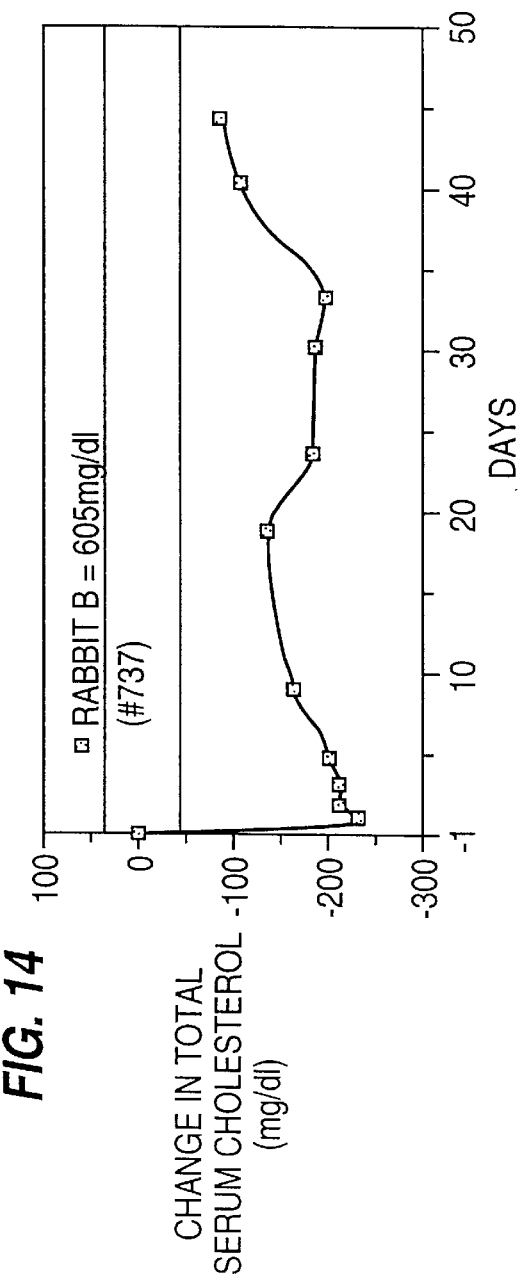

FIG. 14 Injection of the poly-L-lysine/DNA complex containing 9 mg of the chimeric PEPCK-hLDLr gene. In our second experiment, 9 mg of the PEPCK-hLDLr gene appropriately condensed with galactosylated poly-L-lysine were administered to rabbit #737. As shown in FIG. 14, the treatment resulted in a 38% reduction of total serum cholesterol levels which lasted for about 5 weeks. Thus, a 3-fold increase in the dose of DNA complex resulted in a 2-fold reduction in total serum cholesterol levels.

Figure 15:
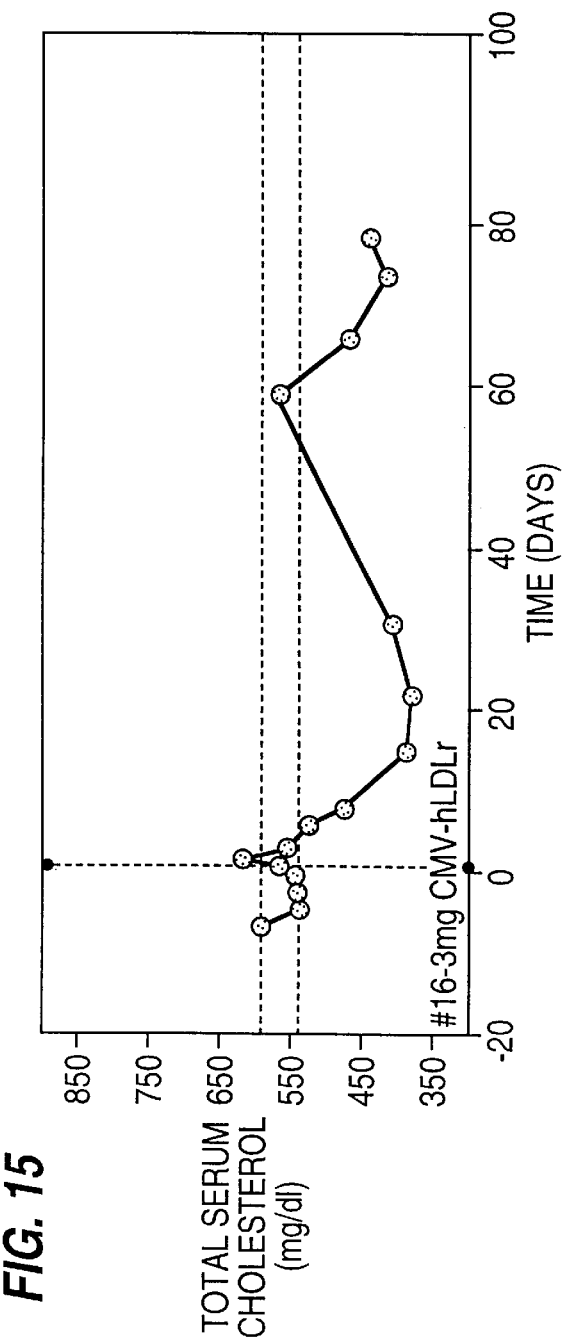

FIG. 15 Injection of the poly-L-lysine/DNA complex containing 3 mg of the chimeric CMV-hLDLr gene. The administration of a DNA complex solution containing 3 mg of the chimeric CMV-hLDL receptor gene to rabbit #16 resulted in a maximal reduction of 30% in total serum cholesterol levels (FIG. 15). Eleven weeks after the injection, cholesterol levels are still 20% below those observed before the treatment.

Figure 16A:
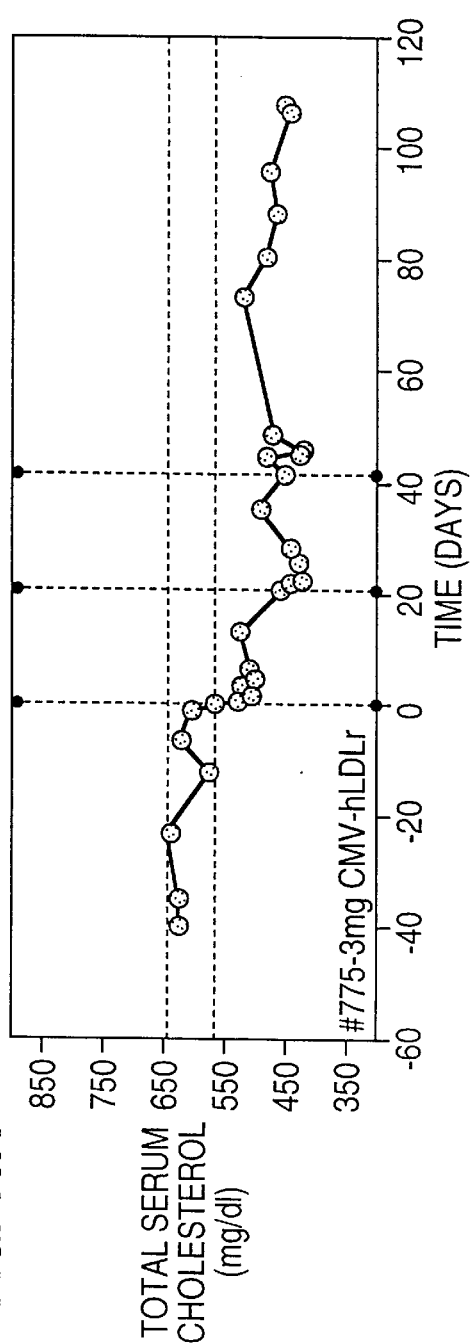
Figure 16B:
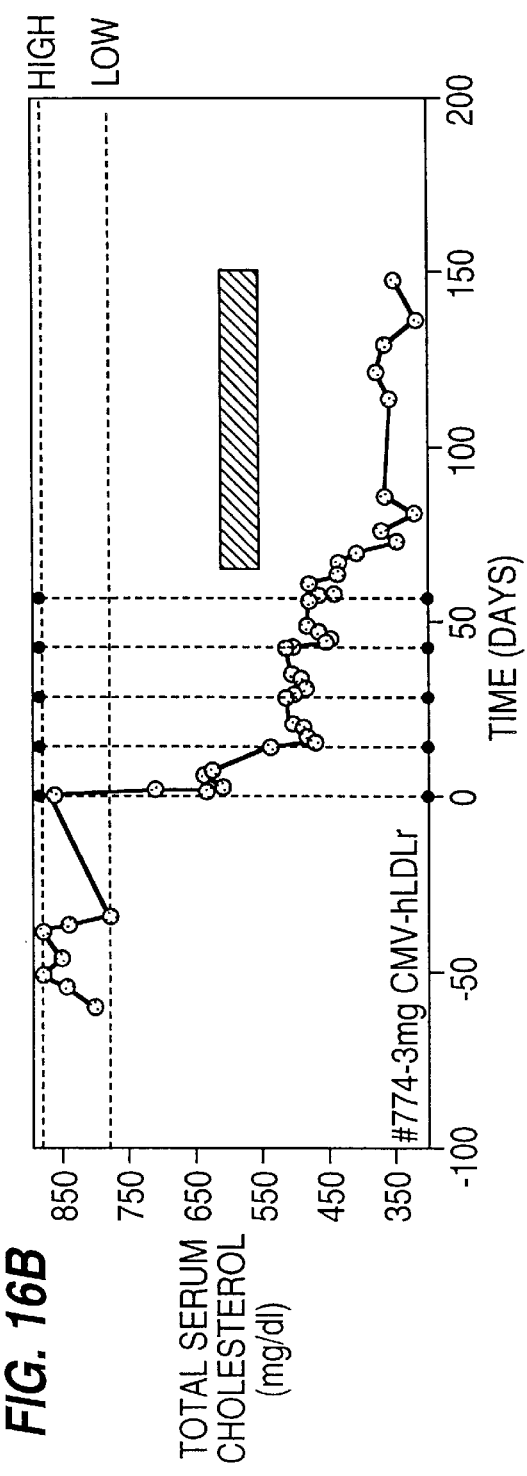

FIGS. 16A and 16B Injection of multiple doses of the poly-L-lysine/DNA complex containing 3 mg of the chimeric CMV-hLDLr gene. Rabbits #775 (FIG. 16A) and #774 (FIG. 16B) were injected with 3mg of the pCMV-hLDLR complex. In rabbit #775, this caused a maximal 24% reduction in cholesterol concentration in the blood, 3 weeks after treatment. Two additional injections did not result in a further significant reduction in serum cholesterol. In Rabbit #774, we observed a 36% decrease in the cholesterol levels in the blood (FIG. 16B) after the initial injeciton. Four reinjections once every 2 weeks were performed with the same amount of DNA complex. Two of them resulted in a minimal effect while the other two in a null reduction of total serum cholesterol levels. However, after five administrations of the DNA complex solution containing 3 mg of pCMNV-hLDLr, the concentration of cholesterol had dropped about 48% with respect to pre-treatment levels.

Rabbit #774 was then treated with 10 mg of lovastatin (striped bar) per day for 10 weeks. A further 20% reduction in the levels of cholesterol has been observed. mhe inhibition of the endogenous pathway for cholesterol synthesis has thus brought the cholesterol concentration of rabbit #774 to 40% of that prior to the first gene transfer (FIG. 16B).

Figure 17:
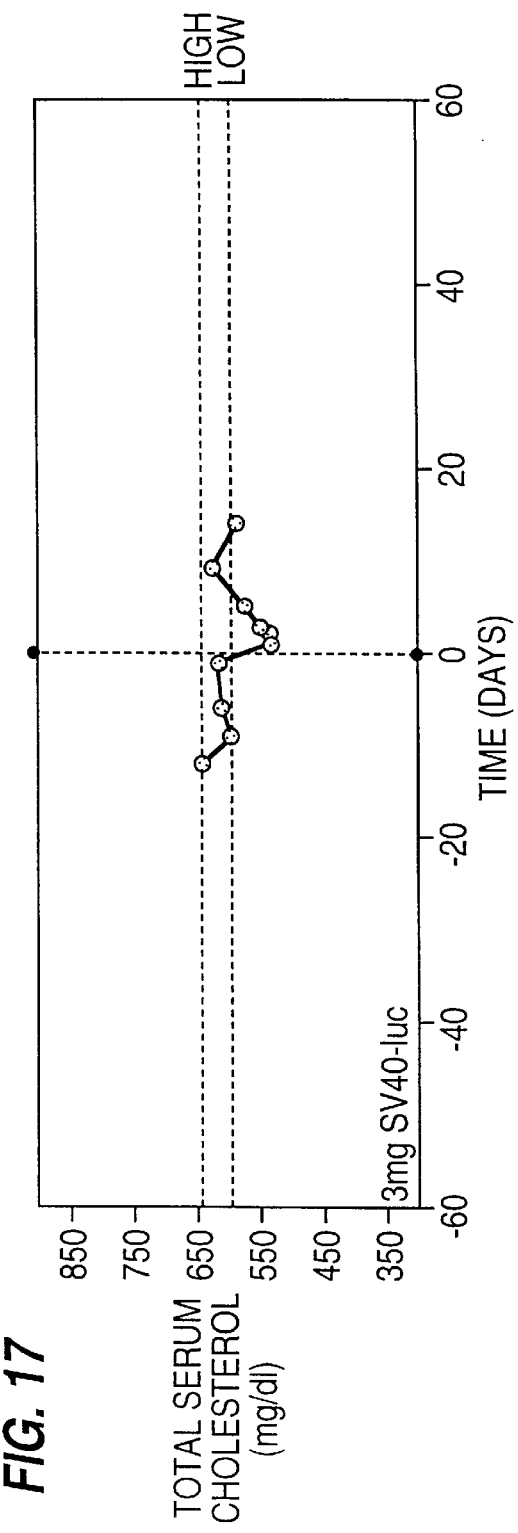

FIG. 17 Mock-injection of the poly-L-lysine/DNA complex containing 3 mg of the chimeric SV40-luciferase gene (irrelevant DNA). In order to control for a possible nonspecific reduction in total serum cholesterol levels by injecting rabbits with the galactosylated poly-L-lysine/DNA complexes in a solution with high NaCl concentration (~900 mM), we have administered a DNA complex solution containing an irrelevant DNA such as the luciferase gene into rabbit #775. FIG. 17 shows that the injection results in a non-significant ($\leq 12\%$) and transient ($\leq 5$ days) reduction in the serum cholesterol concentration. Thus, we have confirmed that the reduction in total serum cholesterol levels after the injection of appropriately condensed DNA particles encoding the human LDL receptor gene are not a result of either the high NaCl concentration of the solution or the presence of galactosylated poly-L-lysine/DNA particles.

Figure 18:
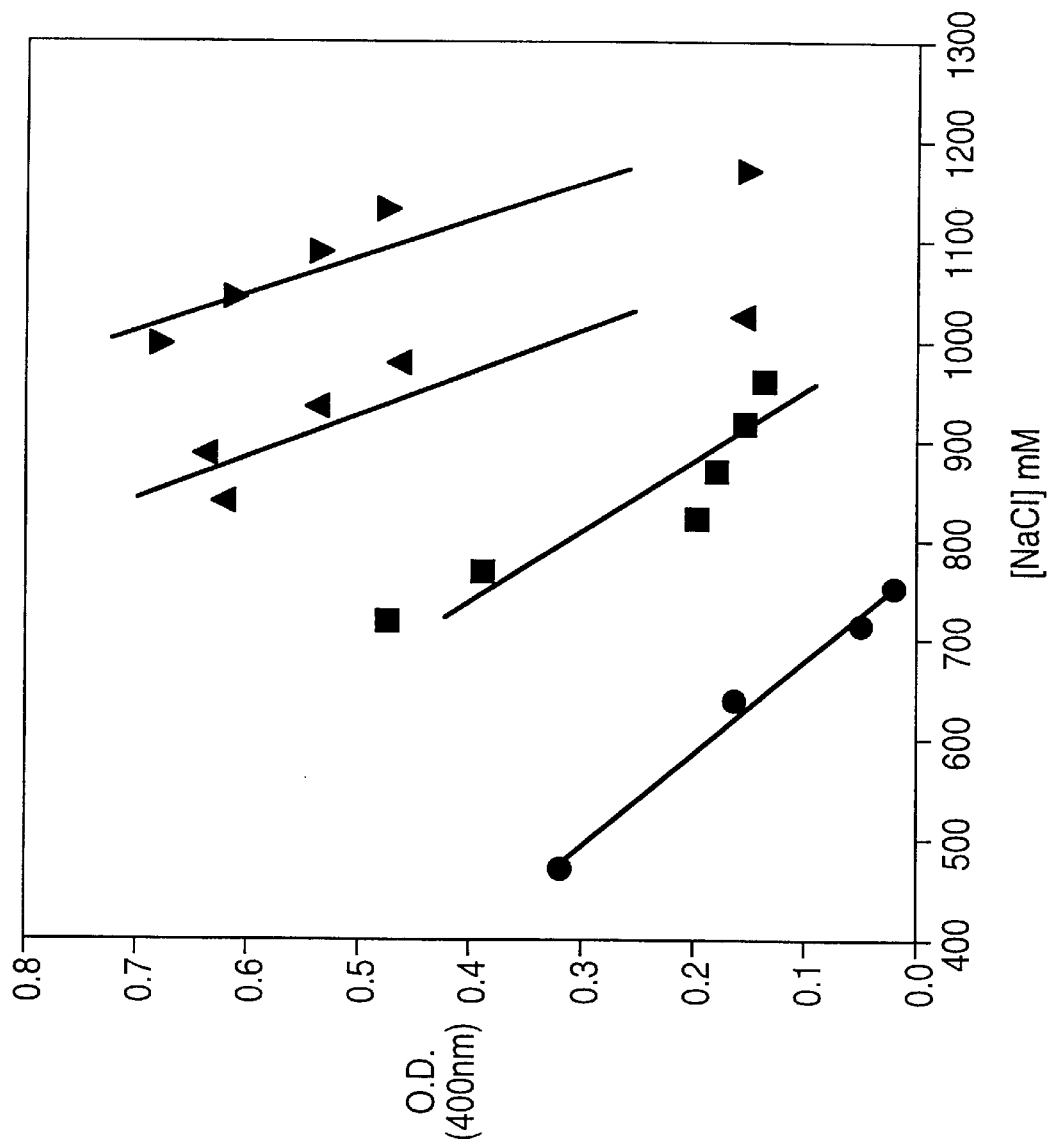

FIG. 18 Relationship of turbidity to NaCl concentration. The figure shows the effect of initial and current NaCl concentration on the turbidity of a DNA/poly-lysine solution. Each line represents a different initial concentration.

Figure 19:
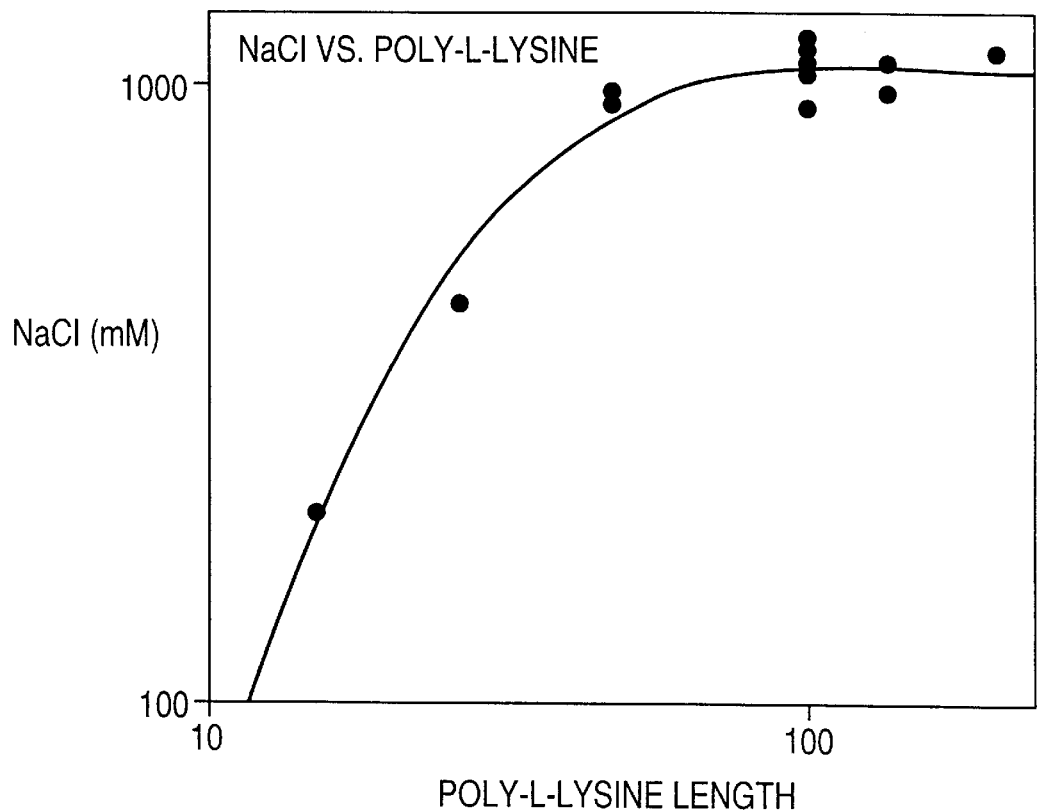
Figure 20A:
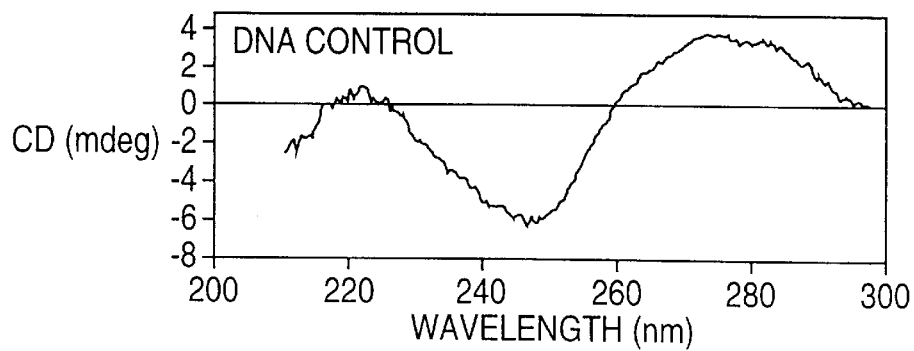
Figure 20B:
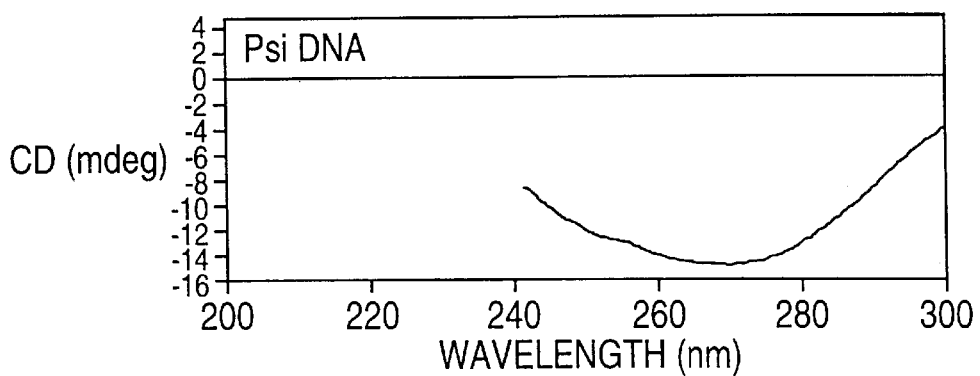
Figure 20C:
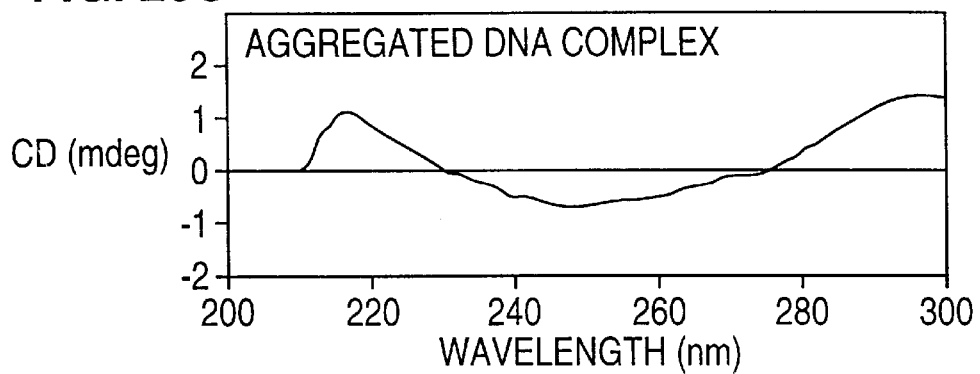
Figure 20D:
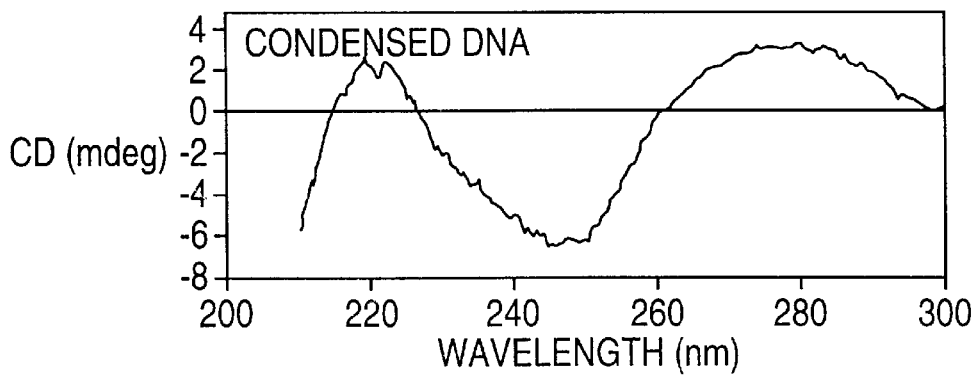
Figure 20E:
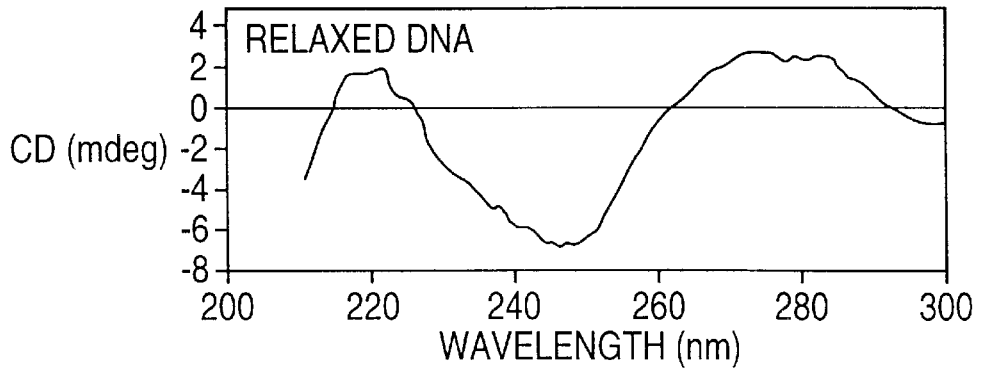

FIG. 19 Effect of poly-L-lysine length on condensation concentration of NaCl.

FIGS. 20A–20E CD spectra for different complexes. CD spectra were taken in a 0.1 cm path-length cuvette. The DNA was complexed with poly-L-lysine at identical molar ratios of amino to phosphate groups and various CD spectra compared: (FIG. 20A) standard control for DNA in 1M NaCl; (FIG. 20B) Ψ-DNA as observed at a concentration of NaCl at which multimolecular aggregation occurs; (FIG. 20C) aggregated DNA shows turbidity and decreased ellipticity; (FIG. 20D) condensed, unimolecular complexes of DNA; (FIG. 20E). relaxed DNA complex spectrum. The specta was taken at equal concentrations of polymer and the signal for the buffer was subtracted in each case. details of the assay are presented in the Methods.

DETAILED DESCRIPTION OF THE PREFERRED EMBODIMENTS

The Multicellular Organism

Any multicellular organism into which it may be desirable to introduce exogenous nucleic acid is a potential subject for the present invention. The multicellular organism may be a plant or an animal, preferably the latter. The animal is preferably a vertebrate animal, and more preferably a higher vertebrate, i.e., a mammal or bird, the former being especially preferred. Among mammals, preferred subjects are human and other primates, laboratory animals such as mice, rats, rabbits and hamsters, pet animals such as dogs and cats, and farm animals such as horses, cows, goats, pigs and sheep. It will be noted that these animals come from four orders of class Mammalia: Primata, Rodenta, Carnivora and Artiodactyla.

The Target Cell

The target cells may belong to tissues (including organs) of the organism, including cells belonging to (in the case of an animal) its nervous system (e.g., the brain, spinal cord and peripheral nervous cells), the circulatory system (e.g., the heart, vascular tissue and red and white blood cells), the digestive system (e.g., the stomach and intestines), the respiratory system (e.g., the nose and the lungs), the reproductive system, the endocrine system (the liver, spleen, thyroids, parathyroids), the skin, the muscles, or the connective tissue.

Alternatively, the cells may be cancer cells derived from any organ or tissue of the target organism, or cells of a parasite or pathogen infecting the organism, or virally infected cells of the organism.

A useful procedure for hepatic gene therapy requires an efficient and relatively non-invasive approach to the introduction of genes of interest into the liver. Several techniques, employing receptor mediated gene transfer, have been used with some success. However, there is a need for a readily reproducible procedure which results in the prolonged expression of the transgene in the liver, even in the absence of partial hepatectomy, and which therefore could be used for human gene therapy. Exogenous DNA has been introduced into hepatocytes of adult animals by targeting the asialoglycoprotein (ASGP) receptor by means of a ligand-poly-L-lysine biconjugate. For the ligand-targeting technique to be efficient, the DNA must be in a form which permits it to remain intact in the blood and is small enough to be recognized by the ASGP receptor on the surface of the hepatocytes. Wagner, et al. (1991) have targeted genes to the transferrin receptor in hepatoma cells by condensing the DNA with a poly-L-lysine/transferrin conjugate, into a complex with a diameter of 80–100 nm. This size DNA conjugate is appropriate for recognition by the transferrin receptor in hepatoma cells, but the ASGP receptor of hepatocytes discriminates against ligands larger than 10–20 nm in diameter.

We have developed a procedure for the introduction of genes into the liver of adult animals by receptor mediated uptake which resulted in the expression of the gene for 140 days (the duration of the experiment). This procedure has potential for application to human gene therapy. The major advantages of this method are (i) the ease of preparation of the DNA complex; (ii) the ability to target genes to specific tissues; (iii) the prolonged expression of the gene in the liver; (iv) the relative safety of the complex, since it is devoid of infectious viral DNA; and (v) the episomal maintenance of the introduced gene.

Targeting

A. Generally

"Targeting" is the administration of the compacted nucleic acid in such a manner that it enters the target cells in amounts effective to achieve the clinical purpose. In this regard, it should be noted that DNA and RNA are capable of replication in the nucleus of the target cell, and in consequence the ultimate level of the nucleic acid in the cell may increase after uptake. Moreover, if the clinical effect is mediated by a protein expressed by the nucleic acid, it should be noted that the nucleic acid acts as a template, and thus high levels of protein expression can be achieved even if the number of copies of the nucleic acid in the cell is low. Nonetheless, it is desirable to compact high concentrations of DNA to increase the number of target cells which take up the DNA and the number of DNA molecules taken up by each cell.

The route and site of administration may be chosen to enhance targeting. For example, to target muscle cells, intramuscular injection into the muscles of interest would be a logical choice. Lung cells might be targeted by administering the compacted DNA in aerosol form. The vascular endothelial cells could be targeted by coating a balloon catheter with the compacted DNA and mechanically introducing the DNA.

In some instances, the nucleic acid binding moiety, which maintains the nucleic acid in the compacted state, may also serve as a targeting agent. Polymers of positively charged amino acids are known to act as nuclear localization signals (NLS) in many nuclear proteins. A pSV40-luciferase DNA condensed with poly-L-lysine, was injected in situ into the abdominal muscle of rats. Despite the absence of an explicit target cell binding moiety, we observed a 20-fold higher luciferase activity in rats injected with the complexed DNA than in the rat injected with naked DNA. Nonetheless, in some embodiments, targeting may be improved if a target cell binding moiety is employed.

B. Use of a Target Cell Binding Moiety

If a TBM is used, it must bind specifically to an accessible structure (the "receptor") of the intended target cells. It is not necessary that it be absolutely specific for those cells, however, it must be sufficiently specific for the conjugate to be therapeutically effective. Preferably, its cross-reactivity with other cells is less than 10%, more preferably less than 5%.

There is no absolute minimum affinity which the TBM must have for an accessible structure of the target cell, however, the higher the affinity, the better. Preferably, the affinity is at least $10^3$ liters/mole, more preferably, at least $10^6$ liters/mole.

The TBM may be an antibody (or a specifically binding fragment of an antibody, such as an Fab, Fab, $V_M$, $V_L$ or CDR) which binds specifically to an epitope on the surface of the target cell. Methods for raising antibodies against cells, cell membranes, or isolated cell surface antigens are known in the art:

a. production of immune spleen cells: immunization with soluble antigens Hurrell, J. G. R. (1982) Monoclonal Antibodies: Techniques and Applications. CRC Press, Boca Raton, Fla.

b. immunization with complex antigens: membranes, whole cells and microorganisms. Hurrell, J. G. R. (1982) Monoclonal Antibodies: Techniques and Applications. CRC Press, Boca Raton, Fla.

c. production of monoclonal supernatants and ascots fluids. Andrew, S. M. and Titus, J. A. (1991). Purification of Immunoglobulin G. in Current Protocols in Immunology (J. E. Coligan, A. M. Kruisbeek, D. H. J. Margulies, E. M. Shevach and W. Strober, ed.) pp. A.3.9–A.3.12. Greene Publishing Wiley-Interscience, New York.

d. production of polyclonal antiserum in rabbits. Garvey J. S., Cremer, N. E. and Sussdorf, D. H (eds) (1977) Methods in Immunology: A Laboratory Text for Instruction and Research, Third Edition. W. A. Benjamin, North Hampton, Mass.

e. production of anti-peptide antibodies by chemical coupling of synthetic peptides to carrier proteins Jemmerson, R., Morrow, P. I., Klinman, N. I and Patterson, Y. (1985). Analysis of an evolutionary conserved site on mammalian cytochrome C using synthetic peptides. Proc. Natl Acad. Sci, U.S.A. 82, 1508–1512.

The TBM may be a lectin, for which there is a cognate carbohydrate structure on the cell surface.

The target binding moiety may be a ligand which is specifically bound by a receptor carried by the target cells.

One class of ligands of interest are carbohydrates, especially mono- and oligosaccharides. Suitable ligands include galactose, lactose and mannose.

Another class of ligands of interest are peptides (which here includes proteins), such as insulin, epidermal growth factor(s), tumor necrosis factor, prolactin, chorionic gonadotropin, FSH, LH, glucagon, lactoferrin, transferrin, apolipoprotein E, gp120 and albumin.

The following table lists preferred target binding moieties for various classes of target cells:

| Target Cells | Target Binding Moiety |
| --- | --- |
| liver cells | galactose |
| Kupffer cells | mannose |
| macrophages | mannose |
| lung | Fab fragment vs. polymeric immunoglobulin receptor (Pig R) |
| adipose tissue, | insulin |
| lymphocytes | Fab fragment vs. CD4 or gp120 |
| enterocyte | Vitamin B12 |
| muscle | insulin |
| fibroblasts | mannose-6-phosphate |
| nerve cells | Apolipoprotein E |

Target binding moiety is not strictly necessary in the case of direct injection of the NABM/NA condensed complex. The target cell in this case is passively accessible to the NABM/NA condensed complex by the injection of the complex to the vicinity of the target cell.

C. Liposome-Mediated Gene Transfer

The possibility of detecting gene expresson by encapsulating DNA into a liposome (body contained by a lipid bilayer) using various lipid and solvent conditions, and injecting the liposome into animal tissues, has been extensively demonstrated (1–7). However, despite the potential of this technique for a variety of biological systems, the DNA used in these experiments has not been modified or compacted to improve its survival in the cell, its uptake into the nucleus or its rate of transcription in the nucleus of the target cells. Thus, these procedures have usually resulted in only transient expression of the gene carried by the liposome (4,5).

Cationic lipids have been successfully used to transfer DNA. The cationic component of such lipids can compact DNA in solution (1–3, 7). This method has been shown to result in heavily aggregated DNA complexes (1,2) that, when used for transfecting the DNA in vitro, results in increased efficiency of gene transfer and expression (relative to naked DNA). Although the formation of these complexes can promote gene transfer in vitro, the injection of such complexes in vivo does not result in long lasting and efficient gene transfer. Our condensation procedure could thus provide structural features to the DNA/cationic lipid complex that will make it more amenable to prolonged in vivo expression. We believe that the combination of such methods could be accomplished by either of two procedures:

1. Formation of condensed DNA complex that is later encapsulated using neutral lipids into liposome bodies, or
2. Using the procedure described in this patent, the formation of highly condensed unimolecular DNA complexes upon condensation with cationic lipids could be accomplished.

These complexes should provide a higher efficiency of gene transfer into tissues of animals in vivo.

Our procedure for the condensation of DNA, if coupled to the encapsulation of the resulting compacted DNA into a liposome body, could provide a variety of advantages for transfection into animals:

1. The liposome promotes the passive fusion with the lipid bilayer of the cytoplasmic membrane of mammalian cells in tissues.
2. The condensed DNA could then transfer the genetic information with a higher efficiency through the cell compartments to the nucleus for its expression.
3. Condensed DNA could be protected against degradation inside the cell, thus augmenting the duration of the expression of the newly introduced gene.
4. Possible immunological response to the polycation condensed DNA could be avoided by the encapsulation with the immunologically inert lipid bilayer.

References

1 Ghirlando, R., Wachtel, E. J, Arad, T., and Minsky, A. (1992) DNA packaging induced by micellar aggregates: A novel in vitro DNA condensation system. Biochemistry, 31, 7110–7119.
2 Braulin, W. H., Strick, T. J., and Record, M. T.,Jr. (1982) Biopolymers 21, 1301–1309.
3 Zhu, N., Liggitt, D., Liu, Y., Debs, R. (1993) Systemic gene expression after intravenous DNA delivery into adult mice. Science, 261, 209–211.
4 Alino, S. F., Bobadilla, M., Garcia-Sanz, M., Lejarreta, M., Unda, F., and Hilario, E. (1993) In vivo delivery of human α1-antitrypsin gene to mouse hepatocytes by liposomes. Biochem. Biophys. Research Communications 192, 174–181.
5 Takeshits, S., Losordo, D. W., Kearney, M., Rossow, S. T., and Isner, J. M. (1994) Time course of recombinant protein secretion after liposome-mediated gene transfer in a rabbit arterial organ culture model. Lab. Invest. 71, 387–391.
6 Jarnagin, W. R., Debs, R. J., Wang, S. S., and Bissell, D. M. (1992) Nucleic Acids Res. 20, 4205–4211.
7 Philip, R., Liggitt, D., Phillip, M., Dazin, P., Debs, R. (1993) In vivo gene delivery. Efficient transfection of T lymphocytes in adult mice. J. Biol. Chem. 268, 16087–16090.

The Nucleic Acid Binding Moiety

Any substance which binds reversibly to a nucleic acid may serve as the nucleic acid binding moiety (NABM), provided that (1) it binds sufficiently strongly and specifically to the nucleic acid to retain it until the conjugate reaches and enters the target cell, and does not, through its binding, substantially damage or alter the nucleic acid and (2) it reduces the interactions between the nucleic acid and the solvent, and thereby permits condensation to occur. The ultimate criterion is one of therapeutic effectiveness of the conjugate.

Preferably, the NABM is a polycation. Its positively charged groups bind Ionically to the negatively charged DNA, and the resulting charge neutralization reduces DNA-solvent interactions. A preferred polycation is polylysine. Other potential nucleic acid binding moieties include Arg-Lys mixed polymers, polyarginine, polyornithine, histones, avidin, and protamines.

The Nucleic Acid

Basic procedures for constructing recombinant DNA and RNA molecules in accordance with the present invention are disclosed by Sambrook, J. et al., In: *Molecular Cloning: A Laboratory Manual*, Second Edition, Cold Spring Harbor Press, Cold Spring Harbor, N.Y. (1989), which reference is herein incorporated by reference.

The nucleic acid may be a DNA, RNA, or a DNA or RNA derivative such as a derivative resistant to degradation in vivo, as discussed below. Within this specification, references to DNA apply, mutatis mutandis, to other nucleic acids as well, unless clearly forbidden by the context. The nucleic acid may be single or double stranded. It is preferably of 10 to 1,000,000 bases (or base pairs), more preferably 100 to 100,000, and the bases may be same or different. The bases may be the "normal" bases adenine (A), guanine (G), thymidine (T), cytosine (C) and uracil (U), or abnormal bases such as those listed in 37 CFR § 1.822 (p) (1). The nucleic acid may be prepared by any desired procedure.

In a preferred embodiment, the nucleic acid comprises an expressible gene which is functional in the target cell. For example, the gene may encode coagulation factors, (such as Factor IX), enzymes involved in specific metabolic defects, (such as urea cycle enzymes, especially ornithine transcarbamylase, argininosuccinate synthase, and carbamyl phosphate synthase); receptors, (e.g., LDL receptor); toxins; thymidine kinase to ablate specific cells or tissues; ion channels (e.g., chloride channel of cystic fibrosis); membrane transporters (e.g., glucose transporter); and cytoskeletal proteins, (e.g., dystrophin). The gene may be of synthetic, cDNA or genomic origin, or a combination thereof. The gene may be one which occurs in nature, a non-naturally occurring gene which nonetheless encodes a naturally occurring polypeptide, or a gene which encodes a recognizable mutant of such a polypeptide. It may also encode an mRNA which will be "antisense" to a DNA found or an mRNA normally transcribed in the host cell, but which antisense RNA is not itself translatable into a functional protein.

For the gene to be expressible, the coding sequence must be operably linked to a promoter sequence functional in the target cell. Two DNA sequences (such as a promoter region sequence and a coding sequence) are said to be operably linked if the nature of the linkage between the two DNA sequences does not (1) result in the introduction of a frame-shift mutation in the region sequence to direct the transcription of the desired gene sequence, or (3) interfere with the ability of the gene sequence to be transcribed by the promoter region sequence. A promoter region would be operably linked to a DNA sequence if the promoter were capable of effecting transcription of that DNA sequence. In order to be "operably linked" it is not necessary that two sequences be immediately adjacent to one another. A nucleic acid molecule, such as DNA, is said to be "capable of expressing" a mRNA if it contains nucleotide sequences which contain transcriptional regulatory information and such sequences are "operably linked" to nucleotide sequences which encode the RNA. The precise nature of the regulatory regions needed for gene expression may vary from organism to organism, but in general include a promoter which directs the initiation of RNA transcription. Such regions may include those 5'-non-coding sequences involved with initiation of transcription such as the TATA box.

If desired, the non-coding region 3' to the gene sequence coding for the desired RNA product may be obtained. This region may be retained for its transcriptional termination regulatory sequences, such as those which provide for termination and polyadenylation. Thus, by retaining the 3'-region naturally contiguous to the coding sequence, the transcriptional termination signals may be provided. Where the transcriptional termination signals are not satisfactorily functional in the expression host cell, then a 3' region functional in the host cell may be substituted.

The promoter may be an "ubiquitous" promoter active in essentially all cells of the host organism, e.g., for mammals, the beta-actin promoter, or it may be a promoter whose expression is more or less specific to the target cells. Generally speaking, the latter is preferred. A promoter native to a gene which is naturally expressed in the target cell may be used for this purpose, e.g. the PEPCK (phosphoenol pyruvate carboxykinase) promoter for expression in mammalian liver cells. Other suitable promoters include albumin, metallothionein, surfactant, apoE, pyruvate kinase, LDL receptor HMG CoA reductase or any promoter which has been isolated, cloned and shown to have an appropriate pattern of tissue specific expression and regulation by factors (hormones, diet, heavy metals, etc.) required to control the transcription of the gene in the target tissue. In addition, a broad variety of viral promoters can be used; these include MMTV, SV-40 and CMV. An "expression vector" is a vector which (due to the presence of appropriate transcriptional and/or translational control sequences) is capable of expressing a DNA (or cDNA) molecule which has been cloned into the vector and of thereby producing an RNA or protein product. Expression of the cloned sequences occurs when the expression vector is introduced into an appropriate host cell. If a prokaryotic expression vector is employed, then the appropriate host cell would be any prokaryotic cell capable of expressing the cloned sequences. Similarly, when a eukaryotic expression vector is employed, then the appropriate host cell would be any eukaryotic cell capable of expressing the cloned sequences.

In addition to or instead of an expressible gene, the nucleic acid may comprise sequences homologous to genetic material of the target cell, whereby it may insert itself ("integrate") into the genome by homologous recombination, thereby displacing a coding or control sequence of a gene, or deleting a gene altogether.

In another embodiment, the nucleic acid molecule is "antisense" to a genomic or other DNA sequence of the target organism (including viruses and other pathogens) or to a messenger RNA transcribed in cells of the organisms, which hybridizes sufficiently thereto to inhibit the transcription of the target genomic DNA or the translation of the target messenger RNA. The efficiency of such hybridization is a function of the length and structure of the hybridizing sequences. The longer the sequence and the closer the complementarily to perfection, the stronger the interaction. As the number of base pair mismatches increases, the hybridization efficiency will fall off. Furthermore, the GC content of the packaging sequence DNA or the antisense RNA will also affect the hybridization efficiency due to the additional hydrogen bond present in a GC base pair compared to an AT (or AU) base pair. Thus, a target sequence richer in GC content is preferable as a target.

It is desirable to avoid antisense sequences which would form secondary structure due to intramolecular hybridization, since this would render the antisense nucleic acid less active or inactive for its intended purpose. One of ordinary skill in the art will readily appreciate whether a sequence has a tendency to form a secondary structure. Secondary structures may be avoided by selecting a different target sequence.

An oligonucleotide, between about 15 and about 100 bases in length and complementary to'the target sequence may be synthesized from natural mononucleosides or, alternatively, from mononucleosides having substitutions at the non-bridging phosphorous bound oxygens. A preferred analogue is a methylphosphonate analogue of the naturally occurring mononucleosides. More generally, the mononucleoside analogue is any analogue whose use results in oligonucleotides which have the advantages of (a) an improved ability to diffuse through cell membranes and/or (b) resistance to nuclease digestion within the body of a subject (Miller, P. S. et al., *Biochemistry* 20:1874–1880 (1981)). Such nucleoside analogues are well-known in the art. The nucleic acid molecule may be an analogue of DNA or RNA. The present invention is not limited to use of any particular DNA or RNA analogue, provided it is capable of fulfilling its therapeutic purpose, has adequate resistance to nucleases, and adequate bioavailability and cell take-up. DNA or RNA may be made more resistant to in vivo degradation by enzymes, e.g., nucleases, by modifying internucleoside linkages (e.g., methylphosphonates or phosphorothioates) or by incorporating modified nucleosides (e.g., 2'-0-methylribose or 1'-alpha-anomers).

The naturally occurring linkage is

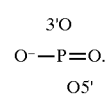

Alternative linkages include the following:

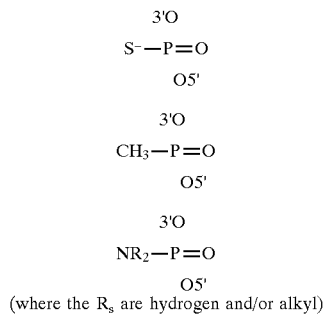

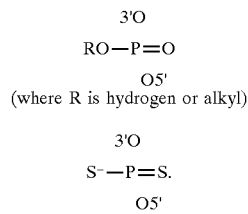

(where the $R_s$ are hydrogen and/or alkyl)

$$\begin{array}{c} 3'O \\ RO-P=O \\ O5' \end{array}$$

(where R is hydrogen or alkyl)

$$\begin{array}{c} 3'O \\ S^--P=S. \\ O5' \end{array}$$

It is also possible to replace the 3'O-P-O5' with other linkages such as 3'O-$CH_2$C(O)-O5', 3'O-C(O)-NH5', and 3'C- $CH_2CH_2$S-C5'.

The entire nucleic acid molecule may be formed of such modified linkages, or only certain portions, such as the 5' and 3' ends, may be so affected, thereby providing resistance to exonucleases.

Nucleic acid molecules suitable for use in the present invention thus include but are not limited to dideoxyribonucleoside methylphosphonates, see Mill, et al., Biochemistry, 18:5134–43 (1979), oligodeoxynucleotide phosphorothioates, see Matsukura, et al., Proc. Nat. Acad. Sci., 84:7706–10 (1987), oligodeoxynucleotides covalently linked to an intercalating agent, see Zerial, et al., Nucleic Acids Res., 15:9909–19 (1987), oligodeoxynucleotide conjugated with poly(L-lysine), see Leonetti, et al., Gene, 72:32–33 (1988), and carbamate—linked oligomers assembled from ribose-derived subunits, see Summerton, J., Antisense Nucleic Acids Conference, 37:44 (New York 1989).

Compaction of the Nucleic Acid

It is desirable that the complex of the nucleic acid and the nucleic acid binding moiety be compacted to a particle size which is sufficiently small to achieve uptake by receptor mediated endocytosis, passive internalization, receptor-mediated membrane permeabilization, or other applicable mechanisms. Desirably, the complex of the compacted nucleic acid, the target binding moiety, and the nucleic acid binding moiety is small, e.g., less than 100 nm, because the sinusoidal capillary systems of the lung and spleen will trap aggregates of that size, and more preferably less than 80 or 90 nm, as that is the typical internal diameter of coated-pit endocytic vesicles.

Since complexes larger than 30 nm may be susceptible to nonspecific takeup by macrophages in the spleen and liver, the conjugate is preferably also smaller than 30 nm.

In the case of the ASGP receptor of the liver, complexes larger than 15–23 nm are excluded from uptake. This size limitation in vivo for the receptor is probably directly related to the existence of another receptor for galactosylated proteins in the Kupffer cells of the liver. The Kupffer cell receptor is very efficient in taking up and degrading galactosylated molecules of larger size in vivo and thus, would compete for the uptake of the galactosylated DNA complex with the ASGP receptor on the surface of hepatocytes. Most preferably, for liver delivery, the complex is less than 23 nm, more preferably less than 15 nm, still more preferably no more than 12 nm in diameter.

The present invention calls for the complex of the nucleic acid and the nucleic acid-binding carrier to be compacted without causing aggregation or precipitation, and preferably to a condensed state (see FIG. 12). For the purpose of the present invention, it is helpful to characterize DNA as having one of the following states: normal (uncondensed); condensed; relaxed; uni-aggregated (clusters of unimolecular toroids); multi-aggregated (clusters of multimolecular toroids); and precipitated. These states are defined in terms of their appearance under electron microscopy (see Table 103).

Condensed DNA is in a state in which interaction with the solvent is minimal and therefore the DNA is in the form of isolated spheres or toroids. It is not fibrous to an appreciable degree. Relaxed DNA, typically formed by dissociation of polycation from the DNA, forms fibers. Aggregated DNA forms clumped or multimolecular toroids.

The theoretical size of a unimolecular DNA complex can be calculated by the formulae set forth in legends "b" and "c" of Table 106. Preferably, the complexes of this invention have a diameter which is less than double the size calculated by one or both of these formulae. Larger complexes are likely to correspond to multimolecularly aggregated DNA.

DNA can be compacted to a condensed state by neutralizing its charge, e.g., by addition of a polycation, or otherwise reducing its interactions with solvent. However, the polycation can cause aggregation or precipitation of the DNA if a chaotropic agent is not employed to prevent it. Compaction therefore can be accomplished by judicious use of both the polycation (to condense the DNA) and (as needed) of a chaotropic agent (to prevent aggregation or precipitation).

Overuse of the chaotropic agent can, however, result in relaxation of the DNA. Preferably, the complex has a unaggregated, unimolecular toroid structure condensed to smaller than 23 nm in diameter; the degree of compaction may be determined by electron microscopy. For example, a complex of the PEPCK-hFIX gene with galactosylated polylysine has been compacted to a unimolecular toroid with a mean diameter of about 12 nm, as shown in Table 106.

The term "unimolecular toroid" indicates that the toroid contains only one nucleic acid molecule; the toroid may contain many carrier (e.g., galactosylated poly-Lys) molecules. A typical ratio is one DNA molecule to about 100 carrier molecules, per "unimolecular" toroid. Alternatively, and perhaps more precisely, this structure may be referred to as a mono-nucleic acid toroid. Unimolecular and multimolecular toroids (the latter each contain more than one DNA molecule) may be distinguished by the different size of each of the complexes when viewed by the electron microscope, indicating the multi- or unimolecular (counting only the DNA molecules) composition of the toroids.

We have also used other techniques to identify structural changes in the DNA upon poly-L-lysine binding. The first of these is the spectrophotometric determination of the turbidity in the solution using the absorbance at 400 nm. Turbidity is primarily an indicator of aggregation. Aggregation is confirmed by a circular dichroism (CD) value greater than 0 at wavelengths from 300 to 340 nm.

FIG. 18 illustrates the effect on turbidity of adding the poly-L-lysine to the DNA solution at different starting concentrations of NaCl. Turbidity increases as the initial concentration of salt is increased (this could be easily confirmed by eye), indicating that the condensation of the DNA complex at lower ionic strength results in a suspension of particles composed of unimolecular DNA-poly-L-lysine complexes interacting with each other. We noted that the solutions of DNA condensed at lower salt concentration were clear, with the presence of particulate matter in suspension. Solutions containing the DNA complex with different degrees of turbidity were analyzed by EM to visualize the DNA structures formed in each situation. Appropriately condensed, unimolecular DNA complexes were found with both clear and slightly turbid solutions. This was not true for the condensation of DNA complexes at initial low ionic strength where we noted minimal absorbance at 400 nm (FIG. 18) because the solutions containing particles in suspension did not absorb at 400 nm. However, when these solutions were analyzed using EM, we noted the expected transitional structures shown in FIG. 1. When the particles in suspension became totally dispersed, the structures identified by EM were essentially identical to condensed unimolecular DNA complexes. Thus, turbidity of the solution containing the DNA complexes is dependent on the initial concentration of salt used for condensation of the complex. Although the mechanisms responsible for the observed differences in the condensation of DNA at initial low and high ionic strength is not clear, we adapted our protocol to appropriately condense DNA, avoiding the formation of turbid solutions.

A more reliable technique for diagnosing the structural transition of DNA-poly-L-lysine complexes in solution is the absorbance of the condensing complex at 260 nm as the concentration of NaCl increases. The uni-aggregated DNA complex in suspension has only 10–30% of the expected absorbance because the particulate matter does not absorb at 260 nm. The addition of NaCl disperses the uni-aggregated DNA complex in suspension which results in the observed steep increase in the absorbance noted in FIG. 11. At this point the solution is clear and there are no visible particulate structures in suspension. This feature of the DNA-poly-L-lysine condensation clearly correlates with the structures shown in FIG. 1. At a concentration of NaCl which causes a steep increase in the absorbance at 260 nm, we observed unaggregated, condensed complexes by EM; before this critical concentration of NaCl was attained, the DNA complex appear aggregated and at higher NaCl concentrations the DNA complex was relaxed. A second transition in absorbance at 260 nm, as a result of the relaxation of the condensed DNA complex that was in suspension, indicates the full solubilization of the DNA complex.

Circular dichroism (CD) can be used to monitor the condensation of DNA. When the spectrum is identical to that of DNA alone, then the DNA complex is assumed to be correctly compacted, i.e., into unimolecular complexes. In another words, the positive spectrum at 220 nm is quantitatively similar to the 220 nm spectrum of DNA alone, and the cross-over (the wavelength at which the spectrum of the complex crosses the 0 point) is essentially identical to that of DNA alone. When the DNA aggregates into multimolecular complexes, the positive spectrum at 270 nm is inverted into a negative spectrum at that wavelength (this is called psi-DNA structure or ψ-DNA).

Table 103 sets forth the characteristics of each state as determined by naked eye observation, circular dichroism spectroscopy, electron microscopy, and absorbance at 260 nm. I t should be noted that any other techniques which are capable of identifying condensed DNA complexes may be used instead of or in combination with those discussed above.

To compact the nucleic acid, the carrier is added to the nucleic acid solution, whereby the carrier disrupts the nucleic acid: solvent interactions allowing the nucleic acid to condense. Preferably, at least the turbidity of the solution is monitored as the carrier is added, so that a change in state is promptly detected. Once turbidity appears, the state of the DNA may be further analyzed by CD spectroscopy to determine whether the DNA is in the condensed or the aggregated state. (Precipitation should also be detectable with the naked eye.) Preferably, the carrier is added sufficiently slowly to the nucleic acid solution so that precipitation and aggregation are minimized. If precipitation or aggregation occur, a chaotropic salt should be added slowly, and the result again examined by CD spectroscopy. The preferred salt is NaCl. Other chaotropic salts can be used as long as they are tolerated by the animal (or cells) to which they will be administered. Suitable agents include Sodium sulfate ($Na_2SO_4$). Lithium sulfate ($Li_2SO_4$), Ammonium sulfate (($NH_4)_2SO_4$, Potassium sulfate ($K_2SO_4$), Magnesium sulfate ($MgSO_4$), Potassium phosphate ($KH_2PO_4$), Sodium phosphate ($NaH_2PO_4$), Ammonium phosphate ($NH_4H_2PO_4$), Magnesium phosphate ($MgHPO_4$), Magnesium chloride ($Mg\ Cl_2$), Lithium chloride (LiCl), Sodium chloride (NaCl), Potassium chloride (KCl), Cesium chloride (CaCl), Ammonium acetate, Potassium acetate, Sodium acetate, Sodium fluoride (NaF), Potassium fluoride (KF), Tetramethyl ammonium chloride (TMA-Cl), Tetrabutylammonium chloride (TBA-Cl), Triethylammoniym chloride (TEA-Cl), and Methyltriethylammonium chloride (MTEA-Cl)

We have investigated variables that affect condensation of DNA in vitro and the functional relevance of these parameters for efficient delivery of DNA complexes into animals by receptor-mediated endocytosis. We noted a strong correlation between the ionic strength at which the condensed DNA-poly-L-lysine complex remains stable in solution and the concentration of DNA. These experiments were performed using a 4.5 kb plasmid containing the promoter from the gene for PEPCK linked to the structural gene for hFIX, using a ratio of DNA to poly-L-lysine that resulted in a 1 to 1 ratio of negative to positive charges in solution. The variation in the final concentration of NaCl necessary to solubilize the particles is a logarithmic function of DNA concentration, in which the condensation of highly concentrated DNA-poly-L-lysine complexes occurs with only a slight increase in ionic strength. This physical characteristic of DNA condensation has clear advantages for the delivery of the DNA particles to tissues of adult animals in vivo since it has little effect on the ionic load in the animal's blood.

The linear fit of the data using the least square method is described by the following function:

$$\log_{10}(NaCl, mM) = b0*(DNA, \mu M\ Phosphate) + b1\ r2 = 0.97$$

where b0=2.52×10E-3, b1=0.577

We have observed variations in the function described by the above equation when we use different DNA plasmids and different DNA preparations during the condensation process. These differences are probably related to the variation in the affinity of poly-L-lysine for DNA of different sources and compositions. For maximum binding affinity we generally use DNA precipitated twice with sodium acetate and 2.5 volumes of −40 ¡C. ethanol (see Methods). We have not found an apparent difference in binding affinity of poly-L-lysine for DNA of different forms (i.e. supercoiled, nicked and linear) and for DNA extracted using anionic exchange chromatography or cesium chloride gradient centrifugation. This may indicate the presence of a contaminant in the DNA preparations from different sources which has poly-L-lysine binding activity, that is eliminated by sequential DNA precipitation.

We have also investigated the effect of the length of the poly-L-lysine on the concentration of NaCl necessary for the effective condensation of DNA (FIG. 19). The correlation between these variables was assessed using a fixed concentration of DNA from different sources. We have used a broad range of poly-L-lysine lengths; essentially the sizes of poly-L-lysine available commercially. However, the length of the poly-L-lysine in an average of various sizes of the protein as determined by low-angle light scattering analysis of individual lots of chemically synthesized poly-L-lysine. The actual distribution of sizes within each sample varies from 60 to 80% of the material being distributed, which is +/− 20% from the average size. This broad distribution within a single size is a source of error in our determinations. Nevertheless, there is a clear correlation observable in FIG. 19 between the length of the poly-L-lysine and the necessary concentration of NaCl needed for the condensation of the DNA complex in solution. This correlation is a linear function of poly-L-lysine length up to a size of 150 lysine residues, after which the function reaches saturation and there is no increase in the concentration of NaCl needed for the condensation of DNA with longer poly-L-lysine. These data are consistent with a cooperative binding between the poly-L-lysine and the DNA phosphate backbone. Thus, by reducing the length of the poly-L-lysine molecules used to condensed the DNA the solution of DNA complex injected into the animals will be less hypertonic. It is also important to consider the dilution of the DNA complex in the blood of the animal to evaluate the functional significance of these changes in ionic strength on the efficiency of this method for gene therapy. We have injected rats with DNA complexes containing longer range of poly-L-lysine lengths than those shown in FIG. 19 and rabbits with the shorter range of sizes of poly-L-lysine, and noted positive and persistent expression of the transfected genes in both cases.

The preferred minimum initial salt concentration is dependent on the compaction activity of the carrier and the chaotropic activity of the salt. If the NABM were $(Lys)_8$, or $(Lys)_{27}$, the initial NaCl concentration could be zero. With longer polyols chains, however, in the absence of NaCl, precipitation would be immediate. With $(Lys)_{50}$, the initial NaCl concentration is preferably be at least about 300 mM. Nonetheless, if the TBM is a protein that affects the condensation, the initial salt concentration could be as low as zero.

The carrier may be added continuously, or in small discrete steps. One may begin with a higher flow rate, or larger aliquots, and reduce the flow rate or aliquot size as the desired endpoint of the reaction is neared. Typically 0.1 to 10% of the carrier solution is added at a time to the DNA solution. Each addition is preferably made every 2 seconds to 2 minutes, with constant vortexing. However, longer settlement times may be allowed.

In one embodiment, a nucleic acid, contained in a salt solution, which is preferably at least 0.5M, but less than 1.5M NaCl, is mixed with poly-L-lysine (109 lysines) containing the covalently linked target cell binding moiety (for example, galactose), which is contained in a solution of NaCl at the same concentration (e.g., 0.5 to 1.5M NaCl). Preferably, the molar ratio of nucleic acid phosphate group to positively charged group of the DNA binding moiety is in the range of 4:1 to 1:4, and more preferably is about 1.5:1.

Some of Applicants' experimental results are set forth in Table 104. We have taken 16 examples (asterisked in the first column of Table 104) which were tested and worked in vivo, and regressed final NaCl concentration (the independent variable) against DNA concentration and poly-L-Lys length (the dependent variables), with the results given in Table 105.

The Conjugation

In the embodiments relying on a target-binding carrier molecule, the nucleic acid binding moiety will be conjugated, covalently or noncovalently, directly or indirectly, to the target cell binding moiety. The conjugation may be performed after, or, more usually before, the loading of the nucleic acid binding moiety with the nucleic acid of interest. Either way, the conjugation should not substantially interfere with the binding of the nucleic acid to the nucleic acid binding moiety, or, for that matter, with the ability of the target cell binding moiety to bind to the target cell.

Pharmaceutical Compositions and Methods

The compacted nucleic acid, optionally conjugated with a TBM, may be admixed with a pharmaceutically acceptable carrier for administration to a human or other animal subject. It will be appreciated that it is possible for a DNA solution to contain both condensed DNA and relaxed DNA. The compositions of this invention preferably are sufficiently rich in condensed complexes so that the absorbance at 260 nm is less than 50% that of naked DNA of equal concentration. As stated in Table 103, condensed DNA usually has an absorbance of 20–30%, and relaxed DNA, 80–100%, that of naked DNA.

The administration may be by any suitable route of administration. The dosage form must be appropriate for that route. Suitable routes of administration and dosage forms include intravascular (injectable solution), subcutaneous (injectable solution, slow-release implant), topical (ointment, salve, cream), and oral (solution, tablet, capsule). With some routes of administration, the dosage form must be formulated to protect the conjugate from degradation, e.g., by inclusion of a protective coating or of a nuclease inhibitor.

The dosage may be determined by systematic testing of alternative doses, as is conventional in the art.

Rats (200–300 g) tolerate as much as 600 μg doses of the DNA complex of Example 1 without any apparent ill effects on growth or health. Mice (25 g) have been injected with 150 μg of that DNA complex without any apparent problem.

In humans, a typical trial dose would be 60–120 mg of DNA; if this dose is too low to be effective or so high as to be toxic, it may be increased, or decreased, respectively, in a systematic manner, until a suitable dose is identified.

For short life span cells, e.g., macrophages, a typical dosing schedule might be one dose every two weeks. For long life span cells, e.g., hepatocytes, one dose every two months might be preferable.

Adjuvants may be used to decrease the size of the DNA complex (e.g. 2–10 mM MgCl), to increase its stability (e.g., sucrose, dextrose, glycerol), or to improve delivery efficiency (e.g., lysosomotropic agents such as chloroquine and monensine). The complexes may be enclosed in a liposome to protect them and to facilitate their entry into the target cell (by fusion of the liposome with the cell membrane).

The invention is illustrated, but not limited, by the following examples.

EXAMPLE 1

Introduction

Christmas disease, or Hemophilia B, is a sex-linked recessive bleeding disorder due to a deficiency of functional coagulation factor IX in the circulation. Human factor IX (hFIX) is a plasma glycoprotein normally synthesized in the liver, that plays an integral role in the intrinsic coagulation pathway. Once it has been converted to its serine protease form (IX$a$) by activated plasma thromboplastin antecedent (factor XI$a$), the activated protein interacts with coagulation factor VIII$a$, calcium ions, and phospholipids to produce a complex that converts factor X to Xa. Factor IX undergoes several post-translational modifications in the liver that are essential for its function before secretion into the blood. These include Vitamin K dependent γ-carboxylation of amino-terminal glutamic acid residues and β-hydroxylation of aspartic acid.

Christmas disease accounts for approximately 10 to 20 percent of all inherited clotting disorders. Affected individuals exhibit a wide range of clinical severity that generally correlates with the level of circulating factor IX. Patients with severe deficiencies of functional factor IX may bleed spontaneously into soft tissues and joints or after minor trauma. Transfusions of plasma or concentrates rich in factor IX are used to abort bleeding episodes by temporarily correcting the deficiency. Unfortunately, clinical management has been confounded by viral contamination of pooled plasma. Blood-borne infections, such as hepatitis and the acquired immunodeficiency syndrome, have become significant problems in the treatment of the hereditary clotting disorders. These complications stress the importance of developing alternative treatments.

The gene for human coagulation factor IX has been identified and sequenced; 1,248 base pairs, in length, the complementary DNA predicts a protein of 416 amino acids, and, after post-translational modifications, the mature protein has a molecular weight of approximately 54,000 Da. A gene encoding human coagulation factor IX may be used for genetic correction of hemophilia B.

A chimeric P-enolpyruvate carboxykinase-human factor IX(PEPCK-hFIX) gene (50% supercoiled/ 50% open circular) was condensed with galactosylated poly-L-lysine (average length 50 or 109 amino acids) by titration with NaCl. This process was monitored using CD spectroscopy and electron microscopy and resulted in the formation of a DNA-carrier complex of 10–12 nm in diameter at a critical NaCl concentration. We have introduced the PEPCK-hFIX gene, conjugated using this procedure, into the intact livers of adult rats and have demonstrated that the DNA-carrier complex specifically targets the gene to this organ and that hFIX DNA, MRNA and hFIX protein can be demonstrated up to 140 days (the duration of the experiment) after administration of the DNA-carrier complex. The gene is present as an episome as determined by Southern analysis of DNA isolated from the liver of an animal 32 days after injection of the DNA-conjugate. Transcription of the PEPCK-hFIX gene was controlled by diet for the entire time course of the experiment; feeding the animals a carbohydrate-free diet for one week resulted in the predicted induction of hFIX in the blood, as detected by Western blot hybridization.

Methods

A. Galactosylation

Polymers of L-lysine-HBr or L-lysine-Cl with an average chain length of 109 (Sigma) were galactosylated essentially as described by Monsigny, et al. (1984) Biol. Cell., 51, 187. Briefly, 2 mg of poly-L-lysine was reacted with 89 g of α-D-galactopyranosyl phenyl-isothiocyanate (Sigma G-3266) dissolved in N,N-Dimethyl formamide (5 mg/ml). The solution was adjusted to pH 9.0 by the addition of 1/10 volume of 1M sodium carbonate pH 9.0. Since the reaction is 10% efficient, 0.8% of the ε-$NH_3$ groups present in the solution are glycosylated. The tube was shielded from light by aluminum foil and mixed for 6 hours at room temperature. The solution was then dialyzed, using Spectra-Por dialysis tubing (Fisher 3500 M.W. cutoff), against 500 ml of 5 mM NaCl buffer for 2 days with frequent changes of buffer (2 changes/day).

B. Analysis of the ligand

The dialyzed solution was then analyzed spectrophotometrically at 205 Å and 250 Å for the concentration of poly-L-lysine and the concentration of phenyl-galactose residues, respectively. This step ensures that significant losses during dialysis have not occurred, and that the galactosylation reaction was complete, since in the solution only the modified galactose will absorb at 250 Å.

C. Complex formation

Plasmid DNA was prepared using standard techniques. The DNA was re-suspended in 10 mM Tris-HCl, pH 8.0, containing 1 mM EDTA and the concentration of the DNA determined spectrophotometrically. The DNA preparation was digested twice with RNAses A+T1. This step ensures that RNA is not present in the solution (RNA inhibits the condensation of DNA by poly-L-lysine). A solution containing a high concentration of DNA (1.5–2 mg/ml) was used in further steps. An example of a typical protocol for DNA condensation is described as follows:

a) 300 μg of DNA in 200 μl of 0.75M NaCl (added from 5M NaCl solution) is vortexed at medium speed, using a VIBRAX machine (IKA-VIBRAX-VXR). This procedure is desirable to increase the effective length of the DNA polymer in high salt solutions, thus achieving efficient binding of the poly-L-lysine moiety to the DNA backbone.

b) 84 μg of poly-L-lysine-galactose in 200 μl of 0.75M NaCl (added from a 5M NaCl solution) is added dropwise over a period of 30 minutes to 1 hour in 20 μl aliquots. This amount translates into a molar ratio of 1 DNA $PO_4^-$ group to 0.7 carrier $NH_3^+$ groups.

c) The solution becomes turbid at the end of the process. 3 μl aliquots of 5M NaCl are added dropwise to the vortexing solution until turbidity disappears as monitored by eye. This process is slow, allowing 30 seconds between the addition of each new aliquot of 5M NaCl. Then the solution is subjected to CD spectroscopic monitoring while 2 μl aliquots of 5M NaCl are gradually added. The condensation process is complete when the diagnostic spectrum of the DNA complex is observed. For subsequent preparations of DNA complex consisting in the same plasmid DNA at the same concentration of nucleotide, the protocol can be followed without monitoring with CD and the results will be fully reproducible. When using different concentration of DNA or a different plasmid the CD monitoring should be repeated.

We have found that an alternative technique for monitoring DNA complex formation gives similar results. This technique consists of the following steps:

a) and b) Idem.

c) The solution becomes turbid at the end of the process. 3 μl aliquots of 5M NaCl are added dropwise to the vortexing solution until turbidity disappears as monitored by eye. This process is slow, allowing 30 seconds between the addition of each new aliquot of 5M NaCl. The solution is then centrifuged at full speed (12000× g) for 30 seconds using a microcentrifuge and the appearance of precipitate is monitored. If a precipitate is observed 2 μl aliquots of 5M NaCl are added. The solution is further vortexed for 0.5 minutes and the centrifugation step is repeated. The appearance of a precipitate is due to the aggregation of the DNA-complex in solution and indicates that the DNA has not been fully collapsed.

Results and Discussion

In developing the procedure described herein, we have monitored the physical structure of the DNA/ligand-poly-L-lysine conjugate using circular dichroism (CD) and electron microscopy and studied the conditions by which a functional complex is generated. We then determined the functional relevance of the physical structure of the DNA/ligand-poly-L-lysine conjugate using intact animals. The DNA was condensed by the addition of the ligand-poly-L-lysine in the presence of varying concentrations of NaCl. Either 60 μg of RNA-free CMV -β-galactosidase (A) or phFIX (B,C,D, and E), diluted to a final volume of 150 μl in 700 mM NaCl were vortexed at medium speed in a VIBRAX apparatus (IKA-VIBRAX-VXR). 19 μg of α-galactopyranosyl-phenyl isothiocyanate/poly-L-lysine biconjugate (Sigma) were diluted in the same way and added dropwise to the vortexing solution of DNA. For in vivo studies, 300 μg of DNA (dissolved in TE buffer, pH 8) in 150 μl of 700 mM NaCl were condensed with 95 μg of α-galactopyranosyl-phenyl isothiocyanate/poly-L-lysine biconjugate in 150 μl of 700 mM NaCl. The slow addition of the polycation results in the formation of a turbid solution which is dissolved by the stepwise addition of 3 μl aliquots of 5M NaCl. The disappearance of the turbidity was monitored by eye and at the point of no turbidity the solutions of DNA/poly-L-lysine complexes were investigated by both electron microscopy (E.M.) and CD spectroscopy. Continuing addition of. 2 μl aliquots of 5M NaCl resulted in structural changes as shown in FIGS. 1A–1F. Representative spectra demonstrating different structural conformations of the DNA complex at various concentrations of NaCl and in the presence and absence of added poly-L-lysine, are presented in FIG. 1. Polycation binding to DNA results in a specific spectrum characterized by a displacement of the cross-over to longer wavelengths; this shift can be correlated with the chiral packing of DNA/poly-L-lysine conjugates in high order, asymmetric structures similar to the Ψ-form of DNA. As shown in FIG. 1A, double stranded DNA (in 1M NaCl) has a characteristic spectrum which was markedly altered by the addition of poly-L-lysine at varying ionic strengths. (FIG. 1a). When the ionic strength of the DNA/ligand-poly-L-lysine conjugate was increased the complex proceeded through a transition from an aggregated (FIG. 1C) to a condensed state (FIG. 1D & FIG. 1E). This corresponds to a shift in the spectrum of the complex as shown in FIG. 1A. The change in the CD spectra at 220 nm and the shift in the cross-over (0 line in FIG. 1A) that occurs with increasing ionic strength of the solution is of particular importance in monitoring the formation of condensed DNA complex by means of CD spectroscopy. If the ionic strength is increased above the critical range required for the condensation of the DNA complex, the complex assumes a non-condensed, relaxed conformation (FIG. 1F). This transition in the conformation of the DNA complex cannot be monitored by CD spectroscopy so that a rigorous titration of NaCl is critical to the success of this procedure. It is important to note that the diameter of the DNA complex observed in FIG. 1D (about 10 nm) conforms with the discrimination range desirable for internalization of molecular ligands by the hepatic receptor for asialoglycoproteins.

We therefore verified the functional relevance of the observed DNA structures as vehicles to transfer of the DNA into hepatocytes in vivo by receptor-mediated endocytosis. In order to establish the nature of the uptake process, we followed the removal of the DNA complex from the media by HepG2 cells, which contain the asialoglycoprotein receptor. The uptake of the DNA complex was completely inhibited when a 100-fold molar excess asialogetuin was used as a competitor, indicating that the complex was being taken up by receptor-mediated endocytosis via the ASGP.

A plasmid (pPFIX) containing a chimeric gene composed of the promoter of the gene for the cytosolic form of P-enolpyruvate carboxydinase (PEPCK) from the rat, linked to the cDNA for human coagulation Factor IX (hFIX) (Ferkol, et al., *FASEB J.*, 7:1081 (1993)) was used to follow the delivery and expression of the DNA in the liver. The time-course of expression of hFIX gene in the transfected animals was determined by Western blot hybridization, using a monoclonal antibody against the mature hFIX peptide.

Adult, male Sprague-Dawley rats, approximately 250 g in weight, were anesthetized with ether. 300–400 μl of a solution containing 300 μg of PPFIX complexed as previously described with galactose-poly-L-lysine, were infused into the caudal cava vein. Rats were killed at 0, 4, 8, 12, 32, 72 and 136 days after transfection and tissues and blood samples taken.

Plasma samples (1 μl) from transfected animals and a 1:4 dilution of a human plasma control were subjected to electrophoresis in SDS/10% polyacrylamide gels and transferred onto nitrocellulose membrane filters using standard techniques. the blots were block with 1× PBS, pH 7.4, 0.03% polyoxyethylene sorbitan monolaurate (Tween 20), and 10% (w/v) dry skim milk for two hours at room temperature, followed by incubation with a 1/1000 dilution of a monoclonal murine anti-human factor IX antibody (3 μg/ml) for two hours at room temperature. The monoclonal antibody was kindly provided by Dr. Kenneth Smith (United Blood Services, Albuquerque, N.Mex.). The membrane was washed three times in 1× PBS, pH 7.4 and 0.039% Tween 20, then incubated with a 1/500 dilution of goat anti-murine lgg (H+L)—horseradish peroxidase conjugate. The membrane was then washed vigorously four times with 1× PBS, pH 7.4 and 0.03% Tween 20, and 10 ml of Western blot enhanced chemiluminescence detection solution was applied for one minute. The luminescence emitted from the filter was detected by a 20 second exposure to photographic film. We detected a band hybridizing specifically to the hFIX monoclonal antibody for as long as 140 days. No hybridizing band was detected in untransfected controls.

The liver from an animal 32 days after transfection was taken and genomic DNA isolated using standard techniques. 5 μg of total DNA from the transfected animal and from a nontransfected control were digested with either EcoRI or BgI II overnight. Southern blot electrophoresis was performed by established methods. The DNA from the transfected animal only hybridized to 4.5 kb BglII and a 2.6 kb EcoRI probes.

Spleen, lung, heart and liver tissues were obtained from a rat transfected with 300 μg of the DNA complex. PCR analysis was carried out on total genomic DNA isolated from these tissues. Only the liver of the transfected rat, and not its spleen, lung or heart, or the liver of a control animal, was positive for the 720 bp probe.

The presence of mRNA transcripts for human factor IX in the livers of rats transfected with pFIX was determined after treatment of total cellular hepatic RNA with Moloney Murine Leukemia virus reverse transcriptase and amplification of the resultant cDNA by the polymerase chain reaction. Briefly, 1 μg of total rat liver RNA was treated with 10 U DNAse I (RNAse free), and added to a solution containing 500 nM of $(dT)_{16}$ oligonucleotide primer and 500 nM of each dNTP, and heated to 42° C., and 1 μl of the cDNA pool was amplified by the polymerase chain reaction, using primers expanding the 5' UTR region of the PEPCK promoter and the cDNA for hFIX. As a control, the same RNA samples not converted to cDNA by reverse transcriptase were also used as polymerase chain reaction templates to ensure that contaminating plasmid DNA had not been amplified. The products were separated by agarose gel electrophoresis and Southern blot hybridization using a radiolabeled human factor IX cDNA probe. We observed a band that hybridized specifically with the hFIX probe only in the transfected animals. No bands were detected in either non-transfected controls or transfected samples not converted to cDNA by reverse transcriptase.

The functional activity of hFIX in the plasma of transfected animals was analyzed by measuring the procoagulant activity of human Factor IX. A modification of the one stage, kaolin-activated, partial thromboplastin time with factor IX-deficient human plasma was used. Blood samples were obtained from experimental animals by venipuncture. One fiftieth volume of 500 mM sodium citrate pH 5.0, was added to prevent coagulation, and the plasma was stored at 20° C. The samples were assayed in duplicate, and their activity ws compared to the functional activity of pooled plasma from 24 normal adult human males. In normal human plasma is equivalent 100% functional activity or approximately 3 $\mu$g of human Factor IX per ml. Background Factor IX activity in rat plasm (approximately 0.15 units/ml of Factor IX activity in rat serum) was subtracted from each value of human Factor IX determined in individual animals. The background values is non-specific cross activity of rat Factor IX determined in the human Factor IX assay used in this analysis. Blood samples were obtained from experimental animals by venipuncture. One fiftieth volume of 500 mM sodium nitrate, pH 5.0, was added to prevent coagulation, and the plasma was stored at 20° C. The normal concentration of hFIX in human plasma is 3 $\mu$g/ml, Approximately 15 ng/ml (72 days after transfection) to 1050 ng/ml (48 days after transfection) of active human factor IX were produced in individual animals injected with the DNA complex (Table 102). It is not clear if the small variations in the concentration of recombinant hFIX found in the animals represent a difference in delivery efficiency or in the expression of the newly introduced gene. The hFIX gene was expressed in the animals for up to 140 days (the duration of the experiment), with the highest level noted at 48 days (Table 102).

It has been established using transgenic animals (McGrane, et al., 1988, 1990; Short, et al. 1992) that transcription from the PEPCK promoter can be induced by the administration of a high protein-low carbohydrate diet. In order to demonstrate the regulated expression of the transgene, we analyzed the blood of transfected animals for the presence of hFIX by Western blot hybridization before and after feeding a high protein-low carbohydrate or a normal chow diet for 1 week. We noted up to 3-fold induction of PFIX gene expression in animals containing the PFIX gene for up to 140 days after injection of the DNA complex. The same PEPCK-hFIX gene, introduced into the livers of rats using an alternative method of receptor-mediated gene transfer targeting the ASGE, was active for only two days (Ferkol, et al., 1993); this suggests that the use of a highly compacted DNA complex may be responsible for the prolonged expression of the transgene noted in the present study.

Detection of maintained levels of hFIX protein at time points as long as 140 days is evidence for expression throughout the experimental time course. A human FIX 800 bp. specific transcript was detected by PCR amplification of cDNA generated from total cellular RNA by reverse transcriptase, in the livers of animals expressing functional hFIX protein (FIG. 3A). The presence of mRNA along the experimental time-course would indicate that there is a maintained pool of transcriptionally active DNA in these animals which persistence will explain the prolonged expression and detection of hFIX and specific mRNA.

We have also established the presence of the transfected DNA in the liver of animals 32 days after transfection, and investigated its physical state. The DNA extracted was subjected to restriction enzyme analysis with Bgl II that linearizes the plasmid (4.5. Kb) and with EcoR I that releases the 2.6 Kb chimeric gene from the plasmid. Southern blot hybridization using a hFIX specific probe demonstrated that the transfected DNA remains in episomal state in the transfected livers, since BglII produced a single band consistent with the size of the linear plasmid in contrast to the expected smeared hybridization when random integration occurs (FIG. 3B). We cannot rule out the possibility that a small proportion of the transfected DNA may have undergone random integration into the enome of the transfected animals. However, we believe that this event is improbable since the liver has not been subjected to stimulation of mitosis (i.e., partial hepatectomy).

The asialoglycoprotein receptor is present only in parenchymal cells of the liver. Nevertheless, it has been shown that asialoglycoproteins and other galactose terminal ligands can be taken up by macrophages by a mechanism dependent on the size of the molecular ligand. See Schlepper-Schafer, J. et al., *Exp. Cell. Res*. 165:494 (1986); Bijsterbosch, M. K., et al., *Mol. Pharmacol* 36:484 (1989); and Bijsterbosch, M. K., et al., *Mol. Pharmacol* 41:404 (1992). The size of the DNA/ligand-poly-L-lysine complex in our experiments would be compatible with the discriminating range of the asialoglycoprotein receptor. In order to investigate the specificity of the DNA complex we have obtained DNA from different tissues in a transfected animal and amplified the transfected DNA by PCR. Our results show the absence of amplifiable DNA in tissues other than liver, which would indicate specific uptake by hepatocytes. It is especially interesting that there is no detectable uptake in macrophage-containing tissues like lung and spleen. In contrast, we have detected transfected DNA in the lung and spleen of animals transfected using the method described by Wu, et al. for receptor-mediated endocytosis by means of the asialoglycoprotein receptor. We believe that the small size of the molecular ligand achieved in our experiments is responsible for the specificity of uptake reported here.

EXAMPLE 2

In this Example a different promoter-gene construct (SV40/luciferase) is delivered to a different cell type (macrophages) by means of a different target cell binding moiety.

Introduction

The recognition and uptake of circulating glycoproteins by specific cells are determined by the nature of the exposed sugar residues present on the surface of the molecule. The clearance systems of specific glycoproteins are relatively exclusive and are mediated by specific types of cells. The mannose receptor recognizes glycoproteins with mannose, glucose, fucose, and N-acetylglucosamine residues in exposed, non-reducing positions. Various proteins and glycoprotein conjugates bearing these carbohydrate residues bind to isolated alveolar macrophages, and mannose-terminal glycoproteins infused into the circulation of rats are cleared by Kupffer cells in vivo. Conversely, galactose-terminal glycoproteins, which are cleared by the asialoglycoprotein receptor on hepatocytes, are not recognized by these cells. This cell-surface receptor is expressed by a variety of macrophage subtypes but not circulating monocytes, and mediates the delivery and internalization of mannose-terminal glycoproteins. The mannose receptor recycles constituitively from a pre-lysosomal compartment to the cell surface, and receptor expression is regulated by macrophages.

Macrophages present in various organs (i.e. liver, spleen, lung, and bone marrow) which bind mannose-terminal glycoproteins and therefore may be a target cell for receptor-mediated gene transfer. We tested this hypothesis by examining our ability to deliver functional exogenous genes cells which express the mannose receptor. In this report, a mannose-terminal neoglycoprotein carrier was synthesized and employed as a ligand for receptor-mediated gene transfer to primary murine macrophages isolated from the peritoneal exudates, which abundantly express the receptor on their surface. In addition, the reporter genes were transferred successfully into macrophages present in the liver and spleen of intact rats using the mannose-terminal neoglycoprotein carrier.

Methods

Materials: DNA-modifying enzymes, nucleotides, and 5-Bromo-4-chloro-3-indolyl-β-D-galactopyranoside were purchased from Boehringer Mannheim (Indianapolis, Indiana, USA). All chemicals, including poly (L-lysine), a-D-mannopyranosylphenyl isothiocyanate albumin, and a-D-galactopyranosylphenyl isothiocyanate, were obtained from the Sigma Chemical Company (St. Louis, Mo., USA). Luciferase assay system was obtained from Promega (Madison, Wis., USA). The rabbit anti-β-galactosidase antibody and fluorescein isothiocyanate-conjugated goat anti-rabbit IgG was obtained from the 5 Prime to 3 Prime, Inc. All media, sera, and antibiotics were obtained from Gibco Laboratories (Grand Island, N.Y., USA).

Preparation of mannose-terminal glycoprotein carrier- Synthetic glycoprotein carriers were constructed in which poly (L-lysine), average chain length 100 ($M_r$ 20,000 Da), was glycosylated using a-D-mannopyranosyl phenylisothiocyanate dissolved in N,N-dimethylformamide. The solution was adjusted to pH 9.5 by the addition of 1M Sodium carbonate, pH 9.5. Shielded from light and incubated for 16 hours at 22° C., the solution was dialyzed against 5 mM Sodium chloride for two days. Approximately 0.8 to 1.0% of the amine side chains in the polylysine are glycosylated, as determined by absorbance spectroscopy at 250 nm. As a control, an alternative glycoprotein carrier was synthesized by substituting a-D-mannopyranosyl phenylisothiocyanate with a-D-galactopyranosyl phenylisothiocyanate.

Reporter genes and plasmid preparation: The expression plasmid pGEMluc contained the SV40 viral promoter and enhancer elements ligated to the *P. pyralis* luciferase gene. The plasmids PCMVZ and pCMVIL2r, consisting of the cytomegalovirus (CMV) promoter linked to the *E. coli* lacZ and the interleukin 2 receptor genes, respectively, were also used as reporter genes. The plasmids were grown in *E. coli* DH5a, extracted, and purified by standard techniques (14). Digestions of the plasmids with restriction endonucleases yielded the appropriate size fragments, and purity was established by 1.0% agarose gel electrophoresis. The sizes of plasmids are as follows: pGEMluc , 6.0; pCMVlacZ, 10.9; and pCMVIL2r, 5.4 kB. No bacterial genomic DNA was present in the plasmid preparations.

Preparation of mannose-terminal glycoprotein carrier-DNA complexes. Complexes were formed analogously to Example 1, however, the DNA was about 80% supercoiled and 20% open circular.

Cells and cell culture. Primary macrophages were isolated from the peritoneal cavity of mice four days after the intraperitoneal injection of one milliliter of Brewer's thioglycolate medium. The macrophages from the peritoneal exudate were collected as previously described, and maintained in RPMI Media 1640. This method yielded approximately $5 \times 10^6$ cells per mouse, of which 40–75% were mononuclear phagocytes based on morphological characteristics of the cells and cytochemical identification. Transfections were performed one or two days after collection. The isolated cells were approximately 30–60% confluent at the time of transfection. Viability of cells was determined by serial cell counts and trypan blue exclusion.

DNA delivery to macrophages in culture: One day after isolation, the cells isolated from the peritoneal exudates of mice were washed once with PBS (pH 7.4) and the media was changed immediately before transfection. The conjugate-DNA complex, containing 5 μg (0.4–0.7 pmol) plasmid, was applied to the culture medium and permitted to remain on the cells for 24 hours unless the experiment dictated otherwise. The cells were then either harvested for protein extraction or fixed for in situ β-galactosidase assays at several timepoints after transfection.

Animals: Adult, male Sprague-Dawley rats, weighing approximately 250 g., were anesthetized with ether. Using aseptic technique, 0.3 to 0.6 ml of a solution containing 300 μg (20.8–42.0 pmol) of an expression plasmid complexed to the carrier was injected into the caudal vena cava. The rats were killed at different intervals after infusion of the complexes and the livers, lungs, and spleens of transfected animals were removed for analysis. Furthermore, macrophages were isolated from the alveoli, the bone marrow, and spleen. Bone marrow cells were obtained from the rat's femur. The femur was surgically removed after the experimental animal was sacrificed, and one milliliter of media was infused into and aspirated from the marrow cavity. A single-cell suspension of the marrow was prepared by gently aspirating the cells with a Pasteur pipette. The cells extracted from the bone marrow were maintained in RPMI Media 1640 for 8–12 hours and permitted to attach to glass slides, at which time the adherent cells were fixed for immunocytochemical staining. Non-transfected and mock transfected animals were used as controls in all analyses. The animal research protocol was reviewed and approved by the Case Western Reserve University Institutional Animal Care Committee.

Cytochemical assay for β-galactosidase activity: Individual cells expressing β-galactosidase were identified following incubation with 5-Bromo-4-chloro-3-indolyl-β-galactopyranoside (X-gal) as described previously. Briefly, the cells were fixed with a solution of it glutaraldehyde in PBS for 15 minutes, and then incubated with a solution containing 0.5% X-gal for 12 hours at 37° C. The cells were also stained for nonspecific esterase activity, which produces an insoluble grey-black dye. A minimum of 100 cells in tissue culture were counted to determine the percentage of cells expressing β-galactosidase.

Individual cells expressing β-galactosidase in tissues were identified following incubation with X-gal as described previously. Briefly, the cells were fixed with a solution of 0.5% glutaraldehyde in PBS for 10 minutes, washed twice with PBS, pH 7.5, and then incubated with a solution containing 0.5% X-gal, 5 mM Potassium ferricyanate, 5 mM Potassium ferrocyanate, and 1 mM Magnesium chloride in phosphate-buffered saline (pH 7.4) for 6 hours at 37° C. The stained tissues were fixed in 2% paraformaldehyde/0.5% glutaraldehyde in PBS overnight at 4° C., paraffin embedded by standard procedure, and cut into 5 μm sections. The sections were counterstained with 0.1% nuclear fast red. The adjacent tissue sections were also stained for nonspecific esterase activity, which appears brown-black. Blue colored cells were identified by light microscopy.

Cytochemical identification of macrophages. Cells and tissue sections were stained nonspecific esterase activity, which is relatively specific for mononuclear phagocytes. The cell smears were fixed as described above, and incubated with a filtered solution containing a-naphthyl acetate and Fast Blue BB salt for 10 minutes at room temperature. Tissue sections were stained with this solution for 1–3 hours, and counterstained with 0.1% nuclear fast red.

Immunocytochemical staining for beta-galactosidase: The expression of the transgene in cells isolated from tissues (spleen and bone marrow) transfected in vivo with the plasmid PCMVZ was determined by indirect immunofluorescence. Cell smears were fixed with methanol/acetone for 2 minutes at room temperature, and the cells were incubated with a rabbit anti-b-galactosidase polyclonal antibody for one hour at 37° C. The primary antibody was diluted 1:100 in PBS for immunodetection in the fixed cell smears. Fluorescein isothiocyanate conjugated anti-rabbit immunoglobulin G diluted 1:100 in PBS was used as the secondary antibody. The cells were also counterstained with propidium iodide, which produces red fluorescence in the cell nucleus. Between each incubation, the cells were washed three times for five minutes with PBS. The stained cells were examined by fluorescent microscopy.

Assays for luciferase activity: Cells in culture were harvested, lysed, and analyzed for luciferase activity as described previously. Tissues were harvested from transfected and control rats after the animals were sacrificed and perfused in situ with 50 milliliters of cold PBS, pH 7.5. The tissues were homogenized in lysis buffer and permitted to incubate at 22° C. for 10 minutes. The cell lysates were subsequently centrifuged for 5 minutes at 4° C., and the protein extracts were analyzed for luciferase activity. The lysates were assayed for protein content and the measured integrated light units were standardized for total protein content. All measurements were performed in triplicate and expressed as an average of the values.

Statistical analysis: Data are expressed as means +standard error of the mean (SEM), and evaluated by an analysis of variance using the Student-Newman-Keuls (SNK) test.

Results

In vitro Transfection of Primary Macrophages using the Mannose-terminal Glycoprotein Carrier Using an expression plasmid (PCMVZ) encoding the *E. coli* lacZ gene as a reporter gene, complexes of the plasmid and the mannose-terminal glycoprotein carrier were applied to cells peritoneal exudates cells isolated from mice. Twenty-four hours after transfection, the cells were examined for β-galactosidase activity. The number of transfected cells varied from 5 to 26 per cent of all cells examined. In addition, the proportion of cells with non-specific esterase activity, a cytochemical marker characteristic of monocytes and macrophages, that expressed the transgene ranged from 40% to 75%. Transfections using complexes consisting of an irrelevant plasmid (pGEMluc) bound to the carrier or the expression plasmid (pCMVZ) bound to a galactose-terminal glycoprotein carrier no significant β-galactosidase activity in the exudate cells. Faint blue staining was noted in these control cells, which was most likely due to endogenous β-galactosidase activity. Nevertheless, the percentage and intensity of blue stained cells in the controls was markedly less than that in the transfected dishes, The mannose-terminal glycoprotein carrier-DNA complex appeared to be non-toxic to cells since the percentage of cells viable, based on cell counts and trypan blue staining, after treatment was not significantly different than controls.

Complexes of the mannose-terminal glycoprotein carrier and the expression plasmid pGEMluc were applied to cells isolated from peritoneal exudates for increasing periods of time, and luciferase activity was measured in protein extracts of the transfected cells 24 hours following transfection. As noted in the previous experiments, the level of expression of the transferred gene varied. An eight-fold increase in relative luciferase activity in transfected cells was present ($p<0.01$), whereas protein extracts obtained from cells treated with a complexes formed using a galactose-terminal glycoprotein carrier did not express activity significantly different than the non-transfected control. Furthermore, the addition of a one hundred-fold molar excess of mannosylated bovine serum albumin over complex to the culture media immediately before transfection, which should compete with the carrier for the mannose receptor, completely inhibited the uptake and expression of the reporter gene ($p<0.01$). The duration of the transgene expression in these cells was also examined. The complexes of the mannose-terminal glycoprotein carrier and the expression plasmid pGEMluc were applied to cells for 24 hours, and protein extracts were assayed for luciferase activity at several timepoints after transfection. Optimal transgene expression was detected one day after treatment, and luciferase activity decreased to control levels eight days post transfection.

In vivo Transfection of Macrophages using the Mannose-terminal Glycoprotein Carrier The mannose-terminal glycoprotein carrier was used to transfer reporter genes into the spleen and livers of intact animals. Rats were anesthetized, and 300 μg of plasmid (pGEMluc) was complexed to the mannose-terminal glycoprotein carrier and infused slowly into the caudal vena cava over several minutes. Control and mock transfections of animals using complexes consisting of an irrelevant plasmid (pCMVlacZ) bound to the carrier were also performed in parallel. All animals injected with the complex survived. Luciferase assays were performed four days after infusion of the complexes in tissue homogenates extracted from liver, lungs, and spleen. We observed significant levels of transgene expression in the protein extracts from the spleen obtained from transfected animals. Lower levels of luciferase activity was found in the liver and lung. Non-transfected rats and animals treated with the complexes consisting of an irrelevant plasmid (pCMVlacZ) bound to the mannose-terminal glycoprotein carrier had no significant luciferase activity in protein extracts from any tissue. Twelve days after transfection, luciferase activity approximated background levels in all tissues examined.

The cellular distribution of the transgene expression was examined in sections of spleen and liver three days after the injection of complexes containing pCMVlacZ. The tissues were analyzed for b-galactosidase activity by a cytochemical stain. An animal treated with complexes made using an irrelevant plasmid (pCMVIL2r) served as control. Beta-galactosidase expression was detected in several small cells in the spleen located in the subcapsular region, which conformed to the distribution of cells that expressed non-specific esterase activity based on cytochemical staining. No beta-galactosidase activity was found in the corresponding cells of the control spleen. Rare, blue-stained cells were present in hepatic sections of the transfected animal, and no hepatic endothelial cells, which also have surface mannose receptors, expressed the transgene. Nucleated cells were also isolated from the spleen and stained in vitro. Furthermore, cells extracted from the bone marrow and bronchoalveolar lavage fluid of the transfected and control animals were also treated with a solution containing X-gal and examined for beta-galactosidase activity. Approximately 10–20 percent of the nucleated cells obtained from the spleen stained blue. Rare cells from the mock transfected animal were also faintly blue stained, most likely due to an endogenous β-galactosidase. Nevertheless, the percentage and intensity of blue stained cells in the controls was significantly less than that found in the control animal.

A polyclonal antibody directed against the bacterial beta-galactosidase was used for the immunocytochemical localization of the transgene product to establish that the blue-stained cells in the spleen are not due to endogenous beta-galactosidase or the nonspecific hydrolysis of X-gal. Nucleated cells isolated from the spleen and bone marrow of the animals described above were stained with antibody directed against beta-galactosidase and fluorescein isothiocyanate conjugated anti-rabbit and examined for immunofluorescence. A number of the isolated cells, which were morphologically similar to the blue stained cells demonstrated in the cytochemical assay, had immunofluorescent staining. In addition, these cells had nonspecific esterase activity.

Discussion

We have developed a synthetic glycoprotein complex capable of mediating transfer of functional genes into macrophages in culture and the livers of whole animals. Expression plasmids noncovalently bound to an mannose-terminal glycoprotein carrier can be introduced efficiently into cells that express the mannose receptor. The delivery of DNA by a receptor-mediated gene transfer system is dependent on the presence of receptors on the surface of the targeted cell. Cells that fail to express the asialoglycoprotein receptor were not transfected by this system. In addition to macrophages, other cell types present in the peritoneal exudate that fail to express the mannose receptor, i.e., granulocytes, lymphocytes and fibroblasts, were not transfected. The expression of the reporter gene was localized to cells that had either non-specific esterase or peroxidase activity, reliable cytochemical markers used for macrophage identification.

The specificity and affinity of the ligand for the specific receptor are of considerable importance for the delivery of exogenous genes. Macrophages bind mannose-terminal glycoproteins with high affinity and specificity. The mannose-terminal glycoprotein carrier successfully introduced reporter genes into macrophages in culture and in intact animals, whereas transgene expression was not detected in cells transfected using a galactose-terminal glycoprotein carrier. Uptake does not appear to be due to a non-specific increase in pinocytosis or phagocytosis secondary to the presence glycoprotein in the culture medium. The delivery and expression of the plasmid is inhibited by the addition of mannosylated bovine serum albumin to the culture medium, which presumably competes for the binding site(s) on the mannose receptor. Finally, the substitution of an alternative monosaccharide for mannose could increase the affinity of the DNA-carrier complex, since the mannose receptor also recognizes glycoproteins with glucose, fucose, and N-acetylglucosamine residues in exposed positions. In addition, gene transfer efficiency could potentially be improved by altering the carbohydrate residue to an oligosaccharide, i.e. oligomannose, since monosaccharides are poorer ligands for the receptor than are polyvalent glycoproteins.

A major factor in determining the level of expression of the genes transferred into target cells involves the survival and delivery of the exogenous DNA to the nucleus. Expression of genes introduced by receptor-mediated mechanisms may be limited by the trapping and degradation of the complex in endosomal compartments. Mannose-terminal glycoproteins are introduced into macrophages by receptor-mediated endocytosis, delivered to a pre-lysosomal acidic compartment, and subsequently trafficked to the secondary lysosomes. Apparently, a portion of the introduced conjugate avoids destruction since the transferred DNA must escape degradation after the complex has entered the cell in order for the transgene to be expressed. The physical state of the DNA transferred into cells by these delivery systems may also contribute to its survival and subsequent expression, and highly compact form of DNA may be more resistant to nuclease digestion. Furthermore, the small size of the carrier-DNA complex may also permit the introduction of the plasmid into the cells of the reticuloendothelial system specifically via the mannose receptor and not by phagocytosis.

This study illustrates the potential of specifically directing gene transfer into macrophages by targeting the mannose receptor, and theoretically could provide an approach to the treatment of various inborn errors of metabolism, like Gaucher disease. Pharmacologic therapies that also target the mannose receptor have been shown to be effective in patients with Gaucher disease. Repeated treatments of affected individuals with modified human glucocerebrosidase, in which the outer carbohydrate moieties are cleaved to expose terminal mannose residues, have had substantial clinical improvement in their disease, as demonstrated by reduction in hepatosplenomegaly and resolution of anemia. Unfortunately, the cost of this therapy has been prohibitive to many patients. Bone marrow transplantation has been shown to be curative in the non-neuropathic form of the disease, yet the potential complications of transplantation precludes this procedure in many patients, particularly those in individuals with mild disease. However, because Gaucher disease can be corrected by bone marrow transplantation, one potential approach that has been proposed for the gene therapy of Gaucher disease involves the ex vivo transfer of the normal glucocerebrosidase gene into autologous hematopoietic stem cells and their subsequent introduction into the patient. Alternatively, lymphoblasts could be harvested from the affected individual, infected with replication-incompetent, recombinant retrovirus containing the wild-type gene, and returned to the patient. The secreted enzyme would enter the macrophages via the mannose receptor, thus becoming the secondary targets of therapy. In the system we describe in this manuscript, the macrophage would be the primary target for genetic correction. Practical questions regarding the efficiency of gene delivery, duration and level of expression achieved using this technique, and the immunologic properties of the DNA-carrier complexes need to be addressed. Nevertheless, receptor-mediated gene therapy has the potential of providing a non-invasive approach to the treatment of such diseases.

EXAMPLE 3

We have also used a Fab fragment of a monoclonal antibody directed against the rat polymeric immunoglobulin receptor that is expressed in the airway epithelia. The Fab peptide was covalently coupled to poly-L-lysine and complexed to an SV40-luciferase expression vector using the procedure described below. Rats injected with the DNA complex had luciferase activity for as long as 8 days (the duration of the experiment) only in tissues that expressed the receptor. These finding underline the flexibility of this system for delivering DNA to specific tissues of an adult animal. Introduction Several methods of gene transfer into the respiratory tract have been developed that permits the introduction of functional genes into cells in vivo. However, many of these approaches have lacked specificity and are cytotoxic. Replication deficient, recombinant adenoviruses have been used to deliver the reporter genes to respiratory epithelial cells in a variety of animal models. However, the physiologic effects of treatment with adenovirus are not well understood, and recent-evidence suggests that the first-generation adenoviral vectors administered at high viral titers to animals produce a substantial inflammatory response in the lung. Liposomes have also been used to transfer functional genes to the airway epithelium, but this approach has generally been toxic to cells and lack specificity.

Receptor-mediated gene transfer may provide a method for delivering DNA to specific target cells using a non-infectious, non-toxic vector. This form of gene transfer allows specific tissue targeting with DNA plasmids of considerable size, allowing for delivery of not only the transgene, but also promoter and enhancer elements. In the case of receptor-mediated systems, the delivery of exogenous DNA is dependent on the stability of the DNA-carrier complex, the presence and number of specific receptors on the surface of the targeted cell, the receptor-ligand affinity and interaction, and efficient internalization of the complex. Furthermore, expression of the transferred genes rely on their escape from the endosomal vesicles and trafficking to the target cell's nucleus. The duration of transgene expression in whole animals delivered by exploiting receptor-mediated endocytosis has been generally been transient, returning to background levels within seventy-two hours after treatment. This has been the case for reporter genes introduced into airway epithelial cells via the intratracheal route using adenovirus-polylysine and transferrin-adenovirus-polylysine vectors.

We have demonstrated that in primary cultures of human tracheal epithelial cells, targeting the polymeric immunoglobulin receptor (pIgR) permits the efficient delivery of the transgene specifically to cells that bear the receptor. The polymeric immunoglobulin receptor is expressed only in mucosal epithelial cells, including airway epithelial and submucosal gland cells, and is specifically adapted for the internalization and nondegradative transfer of large molecules. In this report, we show that targeting the polymeric immunoglobulin receptor in vivo results in expression of the transgene in tissues that contain receptor-bearing cells which was maximal six days after transfection.

Methodology

Materials. DNA-modifying enzymes, nucleotides, and 5-Bromo-4-chloro-3-indolyl-β-D-galactopyranoside were purchased from Boehringer Mannheim (Indianapolis, Ind., USA). Luciferase assay system was obtained from Promega (Madison, Wis., USA). Protein A MAPS agarose columns were purchased from BioRad (Richmond, Calif., USA). Papain and poly (L-lysine) were obtained from Sigma Chemical Company (St. Louis, Mo., USA), and N-Succinimidyl-3-(2-pyridyldithio)proprionate was from Pierce Chemical Company (Rockford, Ill., USA). The mouse monoclonal anti-human interleukin 2 receptor antibody was obtained from Dako Corporation. (Carpenteria, Calif., USA), and the fluorescein isothiocyanate-labelled secondary goat anti-mouse antibody was from Sigma Immunochemicals (St. Louis, Mo., USA). The Vectastain ABC method, used in the immunoperoxidase staining procedure, was purchased from Vector Laboratories (Burlingame, Calif., USA). All media, sera, and antibiotics were obtained from Gibco Laboratories (Grand Island, N.Y., USA).

Preparation of Fab fragments. The isolation and papain digestion of antibodies derived from rabbits immunized with rat secretory component has been described previously. Briefly, polyclonal antibody was isolated from rabbit serum using a Protein A MAPS agarose column as described by the manufacturer. Isolated immunoglobulin G (2 mg) was treated with 20 μg papain for 12 hours at 37° C. in the presence of loo mM sodium acetate (pH 5.5) 50 mM cysteine, and 1 mM EDTA. The Fab fragment was separated from intact antibody and Fc fragments by Protein A chromatography. An irrelevant Fab (IFab) was generated by papain digestion of IgG from pre-immune rabbit serum.

Preparation of Fab-polylysine conjugates. The Fab fragment of the anti-pIgR immunoglobulin G was covalently linked to poly (L-lysine) ($M_r$ 10,000 Da) using the heterobifunctional crosslinking reagent N-Succinimidyl 3-(2-pyridyldithio) proprionate (SPDP). The Fab fragment was incubated with a seventy-five fold molar excess of SPDP in 0.1M phosphate buffered saline (PBS), pH 7.5, at 22° C. for 60 minutes. After introduction of 2-pyridyl disulfide structures onto the Fab fragment, unreacted SPDP and low molecular weight reaction products were removed by dialysis. The disulfide bridges of the modified Fab fragment were cleaved with 25 mM dithiothreitol. Both the poly (L-lysine) and SPDP was added in fifteen fold molar excess to the modified Fab fragment, and the reaction was carried out at 22° C. for 24 hours. The conjugate was dialyzed to remove low molecular weight reaction products, and analyzed by separating the resultant proteins on a 0.1% SDS-7.5% polyacrylamide gel electrophoresis. As described previously, analysis of the conjugate demonstrated a protein that migrated slowly, corresponding to a protein greater than 200 kDa in size.

Reporter genes and plasmid preparation. The expression plasmid pGEMluc contained the SV40 viral promoter ligated to the P. pyralis luciferase gene. The plasmids pCMVZ and pCMVIL2r, consisting of the cytomegalovirus (CMV) promoter linked to the E. coli lacZ and the interleukin 2 receptor genes, respectively, were also used as reporter genes. For studies of luciferase activity, these plasmids were employed as irrelevant DNA (IDNA) controls. The plasmids were grown in E. coli DH5a, extracted, and purified by standard techniques. Digestions of the plasmids with restriction endonucleases yielded the appropriate size fragments, and purity was established by 1.0% agarose gel electrophoresis. The sizes of plasmids are as follows: pGEMluc , 6.0; pCMVlacZ, 10.9; and pCMVIL2r, 5.4 kB. No contamination with bacterial genomic DNA or RNA was present in the plasmid preparations.

Preparation of Fab-polylysine-DNA complexes. The carrier-DNA complexes were formed using a method described previously.

Animals: The anti-rat secretory component Fab antibody-polylysine carrier was used to transfer reporter genes into the airways and livers of intact animals. Adult, male Sprague-Dawley rats, weighing approximately 250 g., were anesthetized. Using aseptic technique, 0.3 to 0.6 ml of a solution containing 300 μg of an expression plasmid complexed to the carrier was injected into the caudal vena cava. The rats were sacrificed at several different times after infusion of the complexes and various organs were removed for analysis. Mock transfections of animals using complexes consisting of an irrelevant plasmid bound to the carrier or the expression plasmid bound to a carrier made with an irrelevant Fab fragment were also performed in parallel. The animal research protocol was reviewed and approved by the Case Western Reserve University Institutional Animal Care Committee.

Cytochemical assay for β-galactosidase activity: Individual cells expressing β-galactosidase in tissues were identified following incubation with 5-Bromo-4-chloro-3-indolyl-β-galactopyranoside (X-gal) as described previously. Briefly, the cells were fixed with a solution of 0.5% glutaraldehyde in PBS for 10 minutes, washed twice with PBS, pH 7.5, and then incubated with a solution containing 0.5% X-gal, 5 mM Potassium ferricyanate, 5 mM Potassium ferrocyanate, and 1 nM Magnesium chloride in phosphate-buffered saline (pH 7.4) for 4 hours at 37° C. The stained tissues were fixed in 2% paraformaldehyde/0.5% glutaraldehyde in PBS overnight at 4° C., paraffin embedded by standard procedure, and cut into 5 μm sections. The sections were counterstained with nuclear fast red. Blue colored cells were identified by light microscopy. A minimum of 100 cells were counted to determine the percentage of cells per section that express β-galactosidase. In addition, adjacent sections were stained with Alcian blue/periodic acid Schiff or haematoxylon/eosin using standard protocols.

Assays for luciferase activity: Cells in culture were harvested, lysed, and analyzed for luciferase activity as described previously. Tissues were harvested from transfected and control rats after the animals were sacrificed and perfused in situ with cold PBS, pH 7.5, for five minutes. The tissues were homogenized in lysis buffer and permitted to incubate at 22° C. for 10 minutes. The cell lysates were subsequently centrifuged for 5 minutes at 4° C., and the protein extracts were analyzed for luciferase activity. The lysates were assayed for protein content and the measured integrated light units (10 second interval) were standardized for total protein content. All measurements were performed in triplicate and expressed as an average of the values.

Immunohistochemical staining for the interleukin 2 receptor. The expression of the transgene in tissues transfected with the plasmid pCMVZ was determined by indirect immunofluorescence. Frozen sections of various tissues were fixed with acetone for 10 minutes at −20° C., and treated with for ten minutes at 22° C. to reduce autofluorescence. The sections were then incubated with 10% goat serum in PBS, pH 7.5, for one hour at room temperature. The cells were incubated sequentially with a mouse monoclonal anti-interleukin 2 receptor antibody and fluorescein isothiocyanate-conjugated goat anti-mouse IgG. Both antibodies were diluted 1:100 in PBS, and between each incubation, the cells were washed three times for five minutes with PBS, pH 7.5. The stained cells were examined by fluorescent microscopy.

Results

In vivo Transfection using the Anti-Secretory Component Fab Antibody-Polylysine Carrier All animals injected with the anti-rat secretory component Fab antibody-polylysine carrier-DNA complex survived. Luciferase assays were performed 48 hours after infusion of the complexes in tissue homogenates extracted from liver, lungs, spleen, and heart. We observed significant levels of transgene expression in the protein extracts from the liver and lungs obtained from transfected animals. No detectable luciferase activity was found in the spleen and heart, tissues that do not express the pIgR. Furthermore, animals treated with the complexes consisting of an irrelevant plasmid (pCMVlacZ) bound to the carrier or the expression plasmid (pGEMluc) bound to a carrier based on an irrelevant Fab fragment resulted in no significant luciferase activity in any tissue examined. Thus, only tissues that contain cells bearing pIgR are transfected, and transfection cannot be attributed to the nonspecific uptake of an irrelevant Fab antibody-based complex.

A time course of the expression of the transferred gene, in which luciferase activity in protein extracts derived from the four tissues was measured at different timepoints after injection of the complex, was developed. Luciferase activity persisted in the liver and lung, tissues which have pIgR, achieving maximum values of $13795 \pm 4431$ and $461402 \pm 230078$ integrated light units (ILU) per milligram of protein extract, respectively, at four to six days after injection. Tissues that failed to express the receptor did not have significant transgene expression.

The cellular distribution of the transgene expression was examined in sections of various tissues. Three days after the injection of complexes containing pCMVlacZ, tissue sections of trachea, lung, and liver underwent cytochemical staining for b-galactosidase activity. An animal treated with complexes made using an irrelevant plasmid (pCMVIL2r) served as control. Expression in the trachea was limited to the cells lining the epithelial surface. No beta-galactosidase activity was detected in the tracheal sections from the mock transfected animal. The expression of the transgene was variable, and in some areas of the respiratory epithelium greater than 50% of the cells stained blue. In general, expression ranged from 10–20% of the tracheal epithelial cells. Both ciliated and secretory (goblet) respiratory epithelial cells expressed beta-galactosidase activity, based on Alcian blue/periodic acid Schiff staining of adjacent sections of the airway. No expression from the transgene was detected in the terminal airways or alveoli in either the transfected or control animal (data not shown). This conforms to the distribution of epithelial cells that express the pIgR based on in situ immunohistochemical staining. Rare submucosal glands were evident in the tracheal sections, and only faint blue staining was noted. No inflammatory response was found in any of the tracheal sections from the non-, mock-, and transfected animals. In addition, a mouse monoclonal antibody directed against the human interleukin 2 receptor, a surface protein that has been used as a reporter in the transduction of respiratory epithelial cells in vitro but is not naturally expressed in these cells, was used for immunofluorescent localization of the transgene product in the trachea of the animal transfected with the plasmid pCMVIL2r. Serial sections of the trachea were examined for the presence of fluorescence, and the apical membrane of numerous respiratory epithelial cells from the transfected animal stained appropriately. No specific fluorescent staining was detected in the airway epithelia of an animal mock-transfected with pCMVlacZ. Rare, blue-stained hepatocytes were also found in hepatic sections of the transfected animal. Transgene expression was not identified in the livers from either non- or mock-transfected rats.

Discussion

We report the successful transfer of reporter genes into the airway epithelium in vivo following the injection of a targeting complex consisting of the Fab portion of immunoglobulin G directed against the rat polymeric immunoglobulin receptor conjugated to poly (L-lysine), and noncovalently bound to plasmid DNA. This technique specifically delivered the transgene to the liver and lung, tissues in which this receptor is expressed. Other tissues that do not express the receptor, like the spleen and heart, were not transfected. In addition, following injection of a conjugate prepared with irrelevant Fab fragments no expression was detected, and a complex prepared with a plasmid containing an irrelevant reporter gene also failed to produce detectable luciferase activity. Thus, this complex specifically targets receptor-bearing tissues and the normal trafficking of the receptor's natural ligands does not interfere with the uptake of the transgene in vivo.

Most of the strategies for gene transfer into the respiratory tract currently available depend on viral vectors which do not specifically target respiratory epithelial cells, and rely upon the intratracheal route of delivery to permit targeting of the airway. Intratracheal instillation has also been used to specifically direct gene transfer by other means, like liposomes and adenovirus-transferrin-polylysine conjugates, to the airway epithelium. Systemic delivery of DNA bound to cationic liposomes has not been selective and transfers functional genes to a number of cell types in different tissues. The specificity of receptor-mediated gene transfer for cells that bear the pIgR may be useful in targeting defective cells in the airways of patients with cystic fibrosis.

EXAMPLE 4

INTRODUCTION

Familial hypercholesterolemia (FH) is a human genetic disease characterized by fulminant atherosclerosis and cardiovascular disease. A mutation in the gene for the receptor that mediates the uptake of the low density lipoprotein (LDL) is responsible for this disease. One in every 500 people is heterozygote for a mutation in the LDL receptor gene that is responsible for FH. As a result, LDL is removed from their plasma at only two thirds the normal rate. In the fourth to fifth decade of life, the elevated levels of LDL in plasma cause symptomatic atherosclerosis in these patients. FH-homozygotes (one in a million people) have little or no functional LDL receptor, depending on the domain of the protein that is affected by the mutation. This results in symptomatic coronary atherosclerosis before the age of 20. Treatment with bile acid-binding resins and inhibitors of cholesterol synthesis has been considerably successful in heterozygous FH patients by stimulating the production of LDL receptor from the single normal gene. In FH homozygotes there is no response to drug therapy. Because of the absence of a normal gene that can be stimulated, the replacement of the mutated gene is the only possible approach for the treatment of homozygous FH patients. Since the liver is the major organ responsible for LDL catabolism, the two approaches taken for the treatment of the disease target this organ: liver transplantation and gene therapy. Transplantation of a normal liver into a patient with FH can correct hyperlipidemia, suggesting that reconstitution of the hepatic LDL receptor should be sufficient for phenotypic improvement. Based on this results, all the approaches undertaken using gene therapy for the treatment of FH have targeted the hepatocytes.

In order to understand the mechanism of disease, it is necessary to be aware of the metabolism/fate of cholesterol in the organism. Every cell needs cholesterol for the synthesis of the plasma membrane. The adrenal glands and the corpus luteum in the ovary, in addition, require cholesterol for the synthesis of steroid hormones. The liver is the organ with the highest demand because of the production of bile acids. Cholesterol is obtained in peripheral tissues either from receptor-mediated uptake of low density lipoproteins (LDL), which are the main carriers of endogenous cholesterol in the blood, or by biosynthesis. HMG CoA reductase is the rate-determining enzyme in the pathway. Dietary cholesterol is carried in the bloodstream by chylomicron particles, which are taken up by specific receptors in the liver. In order to provide the different tissues with cholesterol, the liver secretes very low density lipoprotein (VLDL) particles composed of triglycerides, cholesteryl esters and apoproteins C, E and B-100. The uptake of triglycerides from VLDL by adipose tissue and muscle converts these particles into intermediate density lipoproteins (IDL). The LDL receptor, present at highest concentration in the liver and adrenal glands but also in the rest of tissues, recognizes the apo E and apo B-100 components of IDL. Thus, under normal conditions IDL is mostly cleared from the bloodstream by LDL receptor-mediated uptake. The remaining IDL is converted to LDL, which is taken up as well by the LDL receptor that recognizes the apo B-100 component. The clearance of cholesterol from the organism is carried out by the liver, where it is converted to bile acids and secreted into the digestive tract. Although most of the cholesterol is reabsorbed in the terminal ileum for liver reutilization, this pathway provides the route of exit.

Thus, the presence of non-functional LDL receptors that are unable to clear IDL and LDL from the blood results in elevated serum LDL levels, and therefore total serum cholesterol. This is responsible for cholesterol deposition in the artery walls and thus, atherosclerosis.

The Watanabe Heritable Hyperlipidemic (WHHL) rabbit has been previously used to study the effectiveness of gene therapy techniques in correcting hypercholesterolemia. A 12 nucleotide in-frame deletion in the ligand-binding domain of the LDL receptor, similar to one class of mutation found in FH patients, results in symptoms, evolution and histopathology that parallel those of FH.

MATERIALS AND METHODS

Construction of the DNA plasmids

The plasmid DNAs used in this work are pLDLR-17, PCK-hLDLR, PCK-rLDLR and SV40-luciferase. pLDLR-17 was provided by Dr. David Russell (University of Texas, Medical Center, Dallas) and consists of the cytomegalovirus (CMV) promoter/enhancer linked to the human LDL receptor cDNA. It contains a fragment of DNA corresponding to the 5' untranslated region (UTR) of the Alfalfa Mosaic Virus 4 (AMV4) RNA linked to the human LDL receptor cDNA. This sequence acts as a translational enhancer by decreasing the requirements for initiation factors in protein synthesis. The PCK-hLDLR plasmid has been constructed by subcloning the hLDL receptor cDNA from the pLDLR-17 into a pTZ18R vector (Pharmacia) containing the phosphoenolpyruvate carboxykinase (PEPCK) promoter (−460 to +73) and an intron and polyadenylation signal from the simian virus 40 (SV40) small T antigen. In a two step process, the hLDL receptor cDNA was excised with SacI and SmaI from the pLDLR-17 and blunted using T4 DNA polymerase. The blunted fragment was subcloned into the HincII site of a pTZ18R vector. The cDNA was then excised with XbaI and SalI and introduced into the homologous sites of the pTZ18R-PEPCK promoter-SV40 polyA plasmid. For the construction of pPCK-rLDLR, the EcoRI-EcoRI fragment from prLDLR-9 (provided by Dr. James Wilson, University of Pennsylvania) containing the rabbit LDL receptor cDNA was subcloned into the EcoRI site of a pBluescript (Stratagene). This construct was digested with SacI and blunted and then digested with XbaI, and directionally subcloned into the XbaI-blunted HindIII sites of a pTZ18R vector containing the PEPCK promoter (−460 to +73) and an intron and polyadenylation signal from SV40 small T antigen. The SV40-luciferase plasmid (Promega) contains the SV40 viral promoter and enhancer ligated to the P. pyralis luciferase gene inserted into the pUC19 vector (Pharmacia).

Formation of the poly-L-lysine-DNA complex

Production of the galactosylated poly-L-Lysine. Poly-L-lysine was galactosylated as described (PNAS). Two mg of poly-L-lysine-HBr (Sigma P-7890, average chain length, 100) was reacted with 85 mg of a-D-galactopyranosyl phenyl-isothiocyanate (Sigma G-3266). The solution was adjusted to pH 9 by the addition of 1/10 volume of 1M sodium carbonate pH 9. The tube was shielded from light by aluminum foil and mixed for 16 hours at room temperature, then dialyzed using Spectra-Por dialysis tubing (3500 M.W. cutoff) against 500 ml of 5 mM NaCl for 2 days with frequent changes of buffer (4 changes/day). The reaction is stoichiometric and resulted in the galactosylation of 0.8 to 1% of the $NH_3$ groups present in the solution.

Basic protocol for the condensation of DNA. Plasmid DNA was prepared using standard techniques. The DNA was resuspended in 10 mM Tris-HCl, pH 8.0, containing 1 mM EDTA and the concentration of the DNA determined spectrophotometrically. The DNA preparation was treated twice with RNAse A+T1. This step ensures that RNA is not present in the solution (RNA inhibits the condensation of DNA by poly-L-lysine). A solution containing a high concentration of DNA (1.5–2 mg/ml) was used in further steps. An example of a typical protocol for DNA condensation is described as follows:

a) 300 mg of DNA in 200 ml of 0.75M NaCl (added from 5M NaCl solution) is vortexed at medium speed, using a VIBRAX apparatus (IKA-VIBRAX-VXR). This step is necessary to increase the effective length of the DNA polymer in high salt solutions, thus achieving efficient binding of the poly-L-lysine moiety to the DNA backbone.

b) 120 mg of poly-L-lysine or galactosylated poly-L-lysine (average chain length 100) in 200 ml of 0.75M NaCl (added from a 5M NaCl solution) is added dropwise over a period of 30 minutes to 1 hour in 5 µl aliquots. This amount translates into a molar ratio of 1 DNA $PO_4^-$ group to 1 carrier $NH_3^+$ group.

c) The solution becomes turbid at the end of the process. Three µl aliquots of 5M NaCl are added dropwise to the vortexing solution until turbidity disappears as monitored by eye. This process is slow, allowing 60 seconds between the addition of each new aliquot of 5M NaCl. Then the solution is subjected to circular dichroism (CD) spectroscopic monitoring. The solutions of DNA/poly-L-lysine complexes were also analyzed using a JEOL-100C electron microscope. The condensation process is complete when the diagnostic spectrum of the DNA complex is observed and is further established by EM. For subsequent preparations of DNA complex consisting in the same plasmid DNA at the same concentration of nucleotide, the protocol can be followed without monitoring with CD. When using different concentration of DNA or a different plasmid the CD monitoring should be repeated.

Animals

Six adult male Watanabe rabbits (2.8–3.2 Kg of bodyweight) were used in these studies. These animals have been purchased from an established colony at the National Institutes of Health. In order to introduce the DNA complex into the animal, we perform a single injection of 3–10 ml of the DNA-complex solution (˜400–900 mM NaCl) into the marginal ear vein of the rabbit. Approximately 1.5 ml of blood was drawn from the ear artery at 4 p.m. The determination of the concentration of serum cholesterol was performed in the Clinical Laboratory of University Hospitals of Cleveland from 300 µl of serum. At different time points following the introduction of the DNA complex, a rabbit was subjected to a liver biopsy. Total DNA was isolated from the hepatic sample and subjected to PCR amplification in order to detect the presence of the transferred DNA. Rabbit #774 was treated with lovastatin (Mevacor, Merck and Dohme) orally at a dose of 10 mg per day.

Polymerase chain reaction (PCR) amplification

In order to detect the presence of the transferred DNA in the liver of the treated animal, total DNA was isolated from the hepatic sample obtained upon biopsy. In the case of rabbit #737, the DNA of interest was then amplified by PCR using an upstream primer corresponding to positions 32–50 in exon 1 of the 5' UTR of the PEPCK gene and a downstream primer complementary to nucleotides 589–607 of the human LDL receptor cDNA. The amplified fragment corresponds to a 1100 bp band upon hybridization with a 700 bp fragment corresponding to the 5' end of the human LDL receptor cDNA labeled with 32P-dCTP. Appropriate primers corresponding to the chimeric CMV-hLDL receptor gene will be used for the PCR amplification of the transferred plasmid from liver tissue obtained from rabbit #774.

ELISA

Aliquots of 75 µl corresponding to 1 µg of DNA of either newly prepared galactosylated-poly-L-lysine/DNA complex, plasmid DNA or galactosylated-poly-L-lysine were incubated overnight at 4° C. to coat each well of a 96 well microtiter plate. The next day the wells were washed 3 times with phosphate-buffered saline (PBS), then blocked for 2 hours at 37° C. with 5% bovine serum albumin (BSA) in PBS and washed 3 times with the washing buffer containing lo BSA and 0.5% Tween-20 in PBS. Seventy-five µl of serum from rabbit #774 obtained at different time points before and after the repeated administration of the DNA complex at dilutions of 1:3 and 1:30 were added to the wells and incubated for 90 minutes at 37° C. The wells were then washed with washing buffer and incubated with the secondary antibody at 1:3000 dilution. The secondary antibody consists of a mouse monoclonal antibody against rabbit immunoglobulins conjugated to alkaline phosphatase (Sigma). After a final wash with washing buffer, the pNPP substrate at 1 mg/ml in glycine buffer was added to the wells to develop the reaction and spectrophotometric readings at 410 nm were taken in a Dynatech automated ELISA reader. Values taken at 120 minutes were chosen for comparison.

RESULTS

1. Rabbit #676: injection of the poly-L-lysine/DNA complex containing 3 mg of the chimeric PCK-hLDLR gene In a first set of experiments,.we condensed 3 mg and 9 mg of pPCK-hLDLR with galactosylated poly-L-lysine using the techinque developed in our laboratory and we injected them into the peripheral circulation of Watanabe rabbits.

The promoter from the gene for the cytosolic form of the phosphoenolpyruvate carboxykinase (PEPCK) from the rat has been characterized in detail. This promoter was used in these experiments because it is expressed at a high level in the liver and its expression can be controlled by diet and hormones. Starvation and a high protein, carbohydrate-free diet stimulate PEPCK gene transcription while a high carbohydrate diet reduces transcription from the PEPCK promoter. In addition, cAMP and glucocorticoids induce, and insulin inhibits, expression of the PEPCK gene in the liver. The PEPCK promoter is thus suitable for the regulation of a linked structural gene introduced into the liver and was used in our first experiments for the hepatic expression of LDL receptor.

In our first approach we have injected the poly-L-lysine/DNA complex containing 3 mg of DNA. This basic dose of DNA was decided based on previous experiments performed in rats. As shown in FIG. 13, the administration of a DNA complex solution containing 3 mg of the pPCK-hLDLR plasmid in a relaxed state to rabbit #676 did not result in a significant decrease in total serum cholesterol levels. A second injection of DNA complexes appropriately condensed containing 3 mg of the same DNA caused a 20% reduction of the levels of cholesterol in the blood. Four weeks after this second administration, cholesterol returned to approximately pre-treatment levels, reaching a peak at about 35 days.

A 20% decrease in total serum cholesterol levels resulting from the expression of the PCK-hLDL receptor gene will likely be helpful but will not totally alleviate the disorder in FH patients. The number of poly-L-lysine/DNA complexes corresponding to 3 mg of DNA that we have introduced into the animal in our first approximation to these experiments accounts for 0.01% of the total number of asialoglycoprotein receptors in the liver. Consequently, a linear correlation between increasing concentration of.DNA complexes and expression of the PCK-hLDL receptor gene is to be expected.

2. Rabbit #737: injection of the poly-L-lysine/DNA complex containing 9 mg of the chimeric PCK-hLDLR gene In our second experiment, 9 mg of the PCK-hLDLR gene appropriately condensed with galactosylated poly-L-lysine were administered to rabbit #737. As shown in FIG. 14, the treatment resulted in a 38% reduction of total serum cholesterol levels which lasted for about 5 weeks. Thus, a 3-fold increase in the dose of DNA complex resulted in a 2-fold reduction in total serum cholesterol levels.

3. Rabbit #16: injection of the DNA complex containing 3 mg of the CMV-hLDLR gene The promoter for the cytosolic form of the PEPCK gene has the advantage of driving expression in the liver almost specifically and in a regulated fashion. Although they are neither physiologic nor regulated, viral promoters confer high levels of expression to linked structural genes. The chimeric CMV promoter/enhancer has been used with success for gene therapy in WHHL rabbits using adenoviruses for gene transfer. Recently, Kozarsky et al have reported that the CMV promoter/enhancer and the chimeric β-actin/CMV promoter were the promoters of choice in order to obtain highest expression of the human LDL receptor gene transferred to WHHL rabbits using adenoviral infection. Based on these observations, we injected the chimeric CMV-hLDLR gene in order to increase the level of expression of the human LDL receptor gene in the liver of WHHL rabbits.

The administration of a DNA complex solution containing 3 mg of the chimeric CMV-hLDL receptor gene to rabbit #16 resulted in a maximal reduction of 30% in total serum cholesterol levels (FIG. 15). Eleven weeks after the injection cholesterol levels are still 20% below those observed before the treatment.

4. Rabbit #775: repeated administration of the DNA complex containing 3 mg of pCMV-hLDLR Three mg of pCMV-hLDLR contained in a DNA complex solution were injected into rabbit #775, causing a maximal 24% reduction in the concentration of cholesterol in the blood 3weeks after the treatment (FIG. 16A).

The life-span of hepatocytes is reported to be about 108–150 days, so that the persistence of the introduced DNA is limited. Furthermore, a larger therapeutic effect may be of interest after a single injection of the DNA complex. Thus, it may be necessary to inject a patient multiple times to ensure the appropriate level of LDL receptor in the liver. We tested the effect of injecting the DNA complex several times into the same animal. Rabbit #775 has been reinjected twice with 3 mg of the pCMV-hLDLR DNA complex being each injection spaced by 3 weeks. The repeated administration of the complex did not result in a further significant reduction in total serum cholesterol levels.

5. Rabbit #774: repeated administration of the DNA complex containing 3 mg of pCMV-hLDLR Rabbit #774 was injected with 3 mg of the pCMV-hLDLR complex. We observed a 360 decrease in the cholesterol levels in the blood (FIG. 16B). To date four reinjections once every 2 weeks have been performed with the same amount of DNA complex. Two of them have resulted in a minimal effect while the other two in a null reduction of total serum cholesterol levels. However, after five administrations of the DNA complex solution containing 3 mg of pCMV-hLDLR, the concentration of cholesterol has dropped about 48% with respect to pre-treatment levels.

6. Administration of lovastatin to rabbit #774: inhibition of the endogenous synthesis of cholesterol As described in the introduction, there is a pathway for cholesterol synthesis inside the cell. A failure in repressing this metabolic pathway even when the hepatocyte is supplied with cholesterol through the uptake by the human LDL receptor could possibly inhibit further clearance of cholesterol. Lovastatin is a known inhibitor of HMG CoA reductase, the rate-limiting enzyme in the synthesis of cholesterol. Thus, the treatment with this drug of a rabbit that has been injected repeated times with the DNA complex should indicate if cholesterol synthesis was the limiting factor for a further reduction of total serum cholesterol levels. Rabbit #774 has been treated with 10 mg of lovastatin per day for 10 weeks. A further 20% reduction in the levels of cholesterol has been observed. The inhibition of the endogenous pathway for is cholesterol synthesis has thus brought the cholesterol concentration of rabbit #774 to 40% of that prior the first gene transfer (FIG. 16B).

7. Injection of the DNA complex containing an irrelevant DNA

In order to control for a possible artifactual reduction in total serum cholesterol levels by injecting rabbits with the galactosylated poly-L-lysine/DNA complexes in a solution with high NaCl concentration (~900 mM), we have administered a DNA complex solution containing an irrelevant DNA such as the luciferase gene into rabbit #775. FIG. 17 shows that the injection results in a non-significant ($\leq 12\%$) and transient ($\leq 5$ days) reduction in the serum cholesterol concentration. In addition, we have also injected inappropriately condensed DNA complexes encoding the PCK-hLDLR gene. They result in a null or minimal and transient decrease in the cholesterol levels in the blood as well. Thus, we have confirmed that the reduction in total serum cholesterol levels after the injection of appropriately condensed DNA particles encoding the human LDL receptor gene are not a result of either the high NaCl concentration of the solution or the presence of galactosylated poly-L-lysine/DNA particles.

8. Detection of the transferred DNA in the liver of rabbit #774

The DNA complex used in this project is targeted to the hepatic asialoglycoprotein receptor using galactose as a ligand. It is known that macrophages have a similar receptor which is able to clear galactosylated particles larger than 15 nm from the bloodstream.

In order to prove that the human LDL receptor DNA was delivered to the hepatocytes, we performed a liver biopsy in rabbit #737 60 days after the injection of 3 mg of the PEPCK-hLDL receptor gene. Total DNA was isolated and subjected to PCR amplification with the primers described above, together with total DNA from the liver of a non-injected rabbit. The expected band of 1,100 bp was detected in the lane corresponding to the treated rabbit but not in the non-treated animal.

9. Evaluation of the immune response of rabbit #774 after the repeated administration of the poly-L-lysine/DNA complex In the field of gene therapy, immunogenicity of the delivery vehicle is often a concern. While retroviral vectors can escape detection by the immune system, it has been reported that adenoviral vectors do not. The success of a second administration of adenoviral particles for the transfer into Watanabe rabbits of the human LDL receptor gene was blocked by the onset of an immune response against the viral proteins (REF Kozarsky).

The system for receptor-mediated gene transfer has not been studied in depth in regard of its immunogenicity. It has been reported that after the repeated administration of an asialoorosomucoid-poly-L-lysine/DNAcomplexintomice, neutralizing antibodies against the asialoorosomucoid and poly-L-lysine components of the complex but not against the DNA can be detected at a dilution 1:1000 (REF). Ferkol et al also reported the detection of circulating antibodies at a 1:2000 dilution against the Fab fragment-poly-L-lysine but not the DNA moiety of a complex upon repeated administration into mice.

We thus needed to test if the use of galactosylated-poly-L-lysine for the condensation of DNA was immunogenic as well. For this purpose, the presence of antibodies against the galactosylated-poly-L-lysine-DNA complex was evaluated in sera obtained from rabbit #774 at different time points before and after the repeated administration of the complex. In a first experiment, the DNA complex solution containing 1 µg of DNA was adsorbed to the wells of a microtiter plate and then incubated with sera at dilutions 1:3, 1:30 and 1:300. Bound antibodies were detected with an anti-rabbit secondary antibody conjugated with alkaline phosphatase. There is an increase of antibodies in the serum of rabbit #774 upon repeated administration of the DNA complex. In fact, they start to be detectable after the third injection of the DNA complex but not after the first or the second. In addition, it has to be emphasized that only at dilutions 1:3 and 1:30 could a response be detected.

A second experiment was performed in order to establish which moiety of the DNA complex is responsible for inducing the weak though clear immune response. We then adsorbed to the microtiter plate wells either 1 µg of DNA, freshly prepared DNA complex containing 1 µg of DNA or the corresponding amount of galactosylated-poly-L-lysine. The results show that the galactosylated-poly-L-lysine moiety accounts almost entirely for the induction of an immune response against the complex in Watanabe rabbits.

DISCUSSION

The data presented here strongly suggest that the method has been able to at least partially correct hyperlipidemia in WHHL rabbits.

FIGS. 13–16 clearly show that a single injection of the DNA complex containing the human LDL receptor gene results in a significant decrease of total serum cholesterol levels in WHHL rabbits. This reduction ranges from 20% in rabbit #676 to 38% in rabbit #737. In contrast, we show that the administration of a non-relevant plasmid DNA such as pSV40-luciferase (FIG. 17) or of a human LDL receptor-encoding plasmid that is not appropriately condensed (FIG. 17) results in a null or non-significant decrease in serum cholesterol.

We have used two different promoter regions for the regulation of expression of the human LDL receptor gene. It is tentatively suggested that the CMV regulatory region confers higher levels of expression in the liver of rabbits than the promoter for the cytosolic form of the rat PEPCK gene. This observation may not be correct for every species. PEPCK activity in the liver of rabbits is characterized by being only 10'due to the cytosolic isozyme. In addition, stimulation of the cytosolic gene results in only a 2-fold induction of activity. Thus, the PEPCK promoter may not be the best choice for this species. But the use cf a physiologic and tightly regulated promoter as the one for the PEPCK gene may well be the one of choice over a strong but viral promoter as the CMV in other species or for the treatment of other genetic diseases.

In order to determine the time-course of the therapeutic effect rabbits #676, #737 and #16 were subjected to a single injection of the DNA complex containing the human LDL receptor gene. The reduction in the levels of cholesterol in the blood persisted for 4 weeks in rabbit #676 and for 5 weeks in rabbit #737. Based on previous experiments performed in rats where the expression of the transfected pPEPCK-human Factor IX gene was shown for up to 140 days, we were expecting a longer duration of the effect. Different factors can explain this premature termination of the corrective effect of hyperlipidemia. It is well known that rabbits are highly immunogenic and that rats are not. The synthesis in the WHHL rabbits of a human protein after the introduction of the human LDL receptor gene could possibly trigger an immune response against the foreign protein, although there is an 80% homology between both species at the protein level. In addition, hepatocytes seem to have a limited life-span. Some studies in the rat indicate that the life-span of hepatic cells is 108–150 days. Based on this observation, 40% of the increase in cholesterol levels 5 weeks after the introduction of the DNA complex could result from the physiological turnover of liver cells. However, this fact cannot account for 100% of the increase. In addition, it would contradict with the long-term expression observed in rats injected with pPEPCK-human FIX. Another possible explanation for the premature termination in the therapeutic effects resulting from the expression of the human LDL receptor gene would be inactivation or degradation of the transferred DNA.

The theoretical number of poly-L-lysine-DNA complexes that can be formed with 3 mg of DNA accounts for 0.01% of the total number of asialoglycoprotein receptors in the liver. Consequently, we would expect that an increase in the dose of DNA complex results in an enhanced therapeutic effect. To study the dose-response relationship, we have injected rabbit #676 with 3 mg of pPCK-hLDLR and rabbit #737 with 9 mg of the same DNA. As shown in FIGS. 13 and 14, a 3-fold increase in the dose of DNA complex results in a 2-fold higher reduction in cholesterol levels. Although these data do not establish linear correlation, an increase in the dose clearly results in an enhanced response.

If we consider the poly-L-lysine/DNA complex as a potential drug, it is desirable to be able to repeatedly administer it to the same animal. For this reason, rabbit #774 has been subjected to repeated administration of 3 mg of the CMV-hLD>R DNA once every 2 weeks. After an initial decrease of 36% in serum cholesterol levels following the first injection, the effect of the repeated administration of the DNA complex has not been consistent. Rabbit #775 has been treated 3 times with 3 mg of the CMV-hLDLR DNA. Again, after an initial 24% reduction in the cholesterol levels, the second and third treatments have not resulted in a clear effect. We can find three possible explanations for these results. First, that the DNA complexes were not appropriately condensed. DNA upon condensation with poly-L-lysine can result in three different structures: aggregated (condensed particles out of solution), tightly condensed and relaxed. Only DNA tightly condensed into small particles is effective in delivering genes in vivo. Second, that the rabbits are producing neutralizing antibodies against the vehicle. We have some preliminary data regarding the immune response of rabbit #774 against the poly-L-lysine-DNA complex. Third, further clearance of cholesterol from the blood is limited by an impairment in the endogenous metabolism of cholesterol in the hepatocyte of the mutant Watanabe rabbit. In order to test this last hypothesis, rabbit #774 was treated with lovastatin (10 mg/day), a known inhibitor of HMG CoA reductase, for 10 weeks. The observation of a further 20% reduction in the cholesterol concentration suggests that the inhibition of cholesterol synthesis in the hepatocyte is not complete even when the cell is supplied with cholesterol upon uptake of LDL by the heterologous LDL receptor.

Preliminary results regarding the immunogenicity of the galactosylated-poly-L-lysine/DNA complex indicate that the repeated administration triggers the onset of an immune response in the Watanabe rabbit. They also show that circulating antibodies can recognize the galactosylated-poly-L-lysine but not the DNA moiety. These results agree with previous reports regarding the immunogenicity of an asialoorosomucoid-poly-L-lysine/DNA complex and of an Fab-poly-L-lysine/DNA complex. Though it is clear that the complex designed in our laboratory can in fact elicit an immune response upon repeated administration in the same animal, it has to be noticed that we could only detect circulating antibodies at much lower dilutions (1:3 and 1:30 as compared to 1:1000 and 1:2000 in their case). This observation might be indicative of its better ability to escape detection by the immune system. Nevertheless, serum from more animals subjected to repeated administration of the DNA complex need to be tested for the presence of neutralizing antibodies against the complex in order to conclude that immunogenicity is responsible for the failure of repeated injections in further lowering the cholesterol levels in the Watanabe rabbits.

EXAMPLE 5
DIRECT INJECTION OF COMPLEXED VS NAKED DNA INTO MUSCLE
METHODS

Three rats per experimental set were used in the experiments involving direct tissue injection of the DNA complex. One hundred micrograms of naked- DNA containing the SV40-luciferase gene was injected into the liver and abdominal muscle of one of the animals. The same amount of the SV40-luciferase plasmid was complexed to poly-L-lysine and condensed as described above and injected as well into the liver and abdominal muscle of the other two animals. The rats were sacrificed 48 hours post-injection. A piece of liver and abdominal muscle were obtained for the measurement of luciferase activity.
RESULTS Evaluation of direct injections of the DNA complex into the liver and muscle of rats. The successful transfer of naked DNA into muscle cells of mice by direct injection has been reported. Prolonged and high levels of expression of a chimeric gene containing the Roux sarcoma virus (RSV) regulatory region linked to the luciferase cDNA were observed in the experiments. We have investigated the advantages of using DNA complexed to poly-L-lysine and condensed over using free DNA, when DNA has to be transferred into the liver or muscle by direct injection. Three rats have been used for these experiments. One hundred micrograms of naked DNA encoding SV40-luciferase were injected into the liver and abdominal muscle of one of the animals. The same amount of the pSV40-luciferase plasmid complexed to poly-L-lysine and condensed as described above was injected as well into the liver and abdominal muscle of the other two animals. Rats were sacrificed 48 hours post-injection. A piece of liver and abdominal muscle were homogenized in lysis buffer and cell lysates were analyzed for luciferase activity. All luciferase measurements were performed in triplicate, expressed as an average of the values and standardized for total protein. FIG. 9 shows the integrated luciferase units per mg of protein in the two different sets of animals. The efficiency of transfection of DNA complexed to poly-L-lysine and condensed seems to be slightly higher when injected into the liver. However, it appears to result in a much higher efficiency when introduced into muscle tissue. We observe a 20-fold higher luciferase activity in the sample of muscle injected with the condensed DNA compared to the one injected with naked DNA. We think that highly condensed and packaged DNA may be protected against nucleases and may be more stable. In addition, poly-L-lysines may increase the efficiency of nuclear transport once inside the cell. First, the small size of the complex may allow its passage through nuclear pores and second, strings of positively charged aminoacids as lysine and arginine are known to be nuclear localization signals (NLS) in various nuclear proteins. Regarding the differences found between the response in the liver and in the muscle, it is most probable that the characteristic interconnected structure of skeletal muscle cells makes them a better target for the passive diffusion of DNA from cell to cell. This would easily allow the distribution of the DNA complex along the muscle tissue and its transport to the nuclei.

EXAMPLE 6
DIRECT INJECTION OF NAKED VS CONDENSED DNA INTO THE BRAIN: GENE TRANSFER OF RETINAL GANGLION CELLS IN VIVO
INTRODUCTION

Insertion of foreign DNA into adult neurons has potentials for the study of normal neuronal physiology and for the treatment of neural diseases. Gene transfer in neurons has been achieved using viral vectors, however it requires sophisticated methodologies and usually cells transfected can not be restricted to any particular type of neuron.

Axonal Retrograde transport is a continuous physiological process that has been found to transport a large var ̄ety of different types of molecules. Many molecules are known to be incorporated into the axon lumen through endocytosis, whether they are adsorbed or fluid-pase particles. in the situation where axons have been severed, it is postulated that soluble particles from the extracellular space can diffuse into the axon and move towards the soma.

In the present experiments we tested whether plasmid DNA naked or condensed into a compact spheroid, applied to the cut end of retinal ganglion cell axons in the optic nerve or to the tectum of the brain is transported back to the soma and expressed into protein.
METHODS Three plasmids under the control of one of three promoters which are effective in a wide variety of eukariotic cell types were used: RSV-lacZ, CMV-lacZ and SV40-luc. They were prepared at different concentrations ranging from 1 to 20 $\mu g/\mu l$. pCMV-lacZ and pSV40-luc were complexed with poly-L-lysine (1:1) by Jose Carlos Perales (PNAS, 1994).

Assessment of retrograde transport of the plasmid complex to the retinal ganglion cell somas was done using epifluorescence microscopy FITC-poly-L-lysine was used to form complexes with pCMV-lacz. To assess the retrograde transport of pure plasmid, pRSV-lacZ was digested in one site using Hind III. Biotin-dUTP was then linked to the 3'-OH ends of pRSV-lacZ by reaction with Terminal dexynucleotidyl Transferase. Plasmid was then precipitated and washed from free biotin-dtyrp and resuspended at 2 µg/µl.

Adult Wistar rats were anesthetized and their optic nerves were exposed. 1.5 µl of the plasmid solution (different concentrations and plasmids) was applied covering the Optic Nerve. Optic nerve axons were then cut avoiding the retinal blood supply. Another 1.5 µl of the same plasmid solution was applied in soaked gelfoam. The conjunctiva was then closed. Same procedure was done in the contralateral eye using unspecific plasmid. Animals were sacrificed 3 days later. For direct injection into the tectal area, nimals were anesthetized and injected stereoscopically into the tectal area of the brain with naked DNA or condensed DNA.

For liquid β-galactosidase assays, retinas were kept at −70° C. until they were cell-lysed by repeated thawing and freezing. Tissue was centrifuged at 12000 rpm for 2 min aiid the supernatant collected and analyzed for protein content. Volumes containing 360 µg of protein were incubated overnight at 37° C. in buffer A containing 15 mg/ml chlorophenol red B-D-galactopyranoside (CPRG). The absorbance was recorded.

For luciferase assays were done in lysis supernatants of retinas added with luciferase assay buffer. Samples were put into a luminometer which was injected with D-luciferin and then registered luminiscence.

For in situ β-galactasidase assays (for pRSV-lacZ and pCMV-lacZ) retinas were fixed in 2% formaldehyde, 0.5%; glutaraldehyde, PBS for 30 min., washed in PBS and incubated for 6 hrs at 37° C. in 1 mg/ml X-Gal, 4 mM potassium ferrocyanide, 4 mM potassium ferricyanide, 2 mM $MgCl_2$, PBS pH 7.3, 0.02% Nonidet p-40, 0.01% Deoxycholate. Tissue was then rinsed arid analyzed immediately. Counts of blue labeled cells were made to estimate the percentage of transfected cells.

RESULTS

1) Administration of plasmid DNA to the cut end of rat optic axons results in its retrograde transport to the cell body. Double labeled field (confocal microscopy) from a retina 2 days after administration of FITC-poly-lysine/pCMV-lacZ complex at the cut end of the optic nerve and then incubated in propidium iodide showed that FITC (green), Propidium iodide (red) and the mixture of both nuclei double labeled (yellow), counted in randomized fields represented about 45% of the population of retinal ganglion cells.

Microscopic fields taken at different magnifications showed blue colored cells in the retinal ganglion cell layer following in situ β-galactosidase assay in retina. 20 µg/µl of pRSV-lacZ were administered at cut optic nerve and comparison was made with contralateral eye treated with pSV40-luc. Cells positive for β-galactosidase were noted to be in the range size known only for ganglion cells in the retina. These cells were counted in randomized fields and were estimated to represent 35% of total ganglion cells.

2) Plasmid DNA in retinal ganglion cells is expressed in a dose dependent manner and the condensed DNA is expressed at higher efficiency.

Luciferase activity in retinas from rats whose severed optic nerves were administered with pSV40-luc at increasing concentrations, as compared with retinas just axotomized, or treated with the non-specific plasmid pCMV-lacZ (1 µg/µl) showed concentration dependent increase in activity of pSV40-luc.

The results of β-galactosidase activity in retinas from rats whose severed optic nerves were administered with pCMV-lacZ, as compared with retinas just axotomized, or treated with non-specific plasmid pSV40-luc (10 µg/µl) showed that the highest activity was registered from the maximutn concentration of pCMV-lacZ. pCMV-lacZ complexed with poly-lysine produced higher activity in β-galactosidase than non-specific plasmid.

3) This method can be used in the transfer of specific genes to precise neuronal types through their projections.

4) Intratectal injections of naked and polylysine condensed plasmid DNA can achieve high levels of expression in the cell body of the neuron over 20 days. When the DNA is not condensed with poly-L-lysine the level of expression returns to background after 10 days post-injection (FIG. 10).

REFERENCES:

1. Shapiro, J. T., et al., (1969). Deoxyribonucleic acid-polylysine complexes. Structure and nucleotide specificity. *Biochemistry* 8:3219–3232.
2. Haynes, M., et al., (1970). Structure of nucleic acid-polybase complexes. *Biochemistry* 9:4410–4416.
3. Lang, D. (1973). Regular superstructures of purified DNA in ethanolic solutions. *J. Mol. Biol.* 78:247–254.
4. Lerman, L. S. (1971). A transition to a compact form of DNA in polymer solutions. *Proc. Nat. Acad. Sci. USA* 68: 1886–1890.
5. Olins, D. E., et al., (1967). Model nucleoprotein complexes: Studies on the interaction of cationic homopolypeptides with DNA. *J. Mol. Biol.* 24:157–176.
6. Miller, I. R., et al., (1969). *Biopolymers* 7:619.
7. Carroll, D. (1972). Optical properties of deoxyribonucleic acid-polylysine complexes. *Biochemistry* 11:421–426.
8. Cheng, S. M., et al., (1974). The thermal transition of "psi" DNA monitored by circular dichroism. *FEBS letters* 49: 37–42.
9. Chenge, S. M., et al., (1975). Condensed states of nucleic acids. II. Effects of molecular size, base composition, and present of intercalating agents on the transition of DNA. *Biopolvmers* 14:663–677.
10. Onge, E. C., et al., (1976). Chromatin models. The ionic strength dependence of model histone-DNA interactions: circular dichroism.
11. Moran, F., et al., (1989). Kinetic analysis of Ψ-DNA structure formation induced by histone H1 and its C-terminal domain. *Biophysical Chemistry* 33:133–141.
12. Shih, T. Y., et al., (1970). *J. Mol. Biol.* 52:1–25.
13. Cantor, K. P., et al., (1970). *J. Mol. Biol.* 49:213.
14. Li, H. J. (1973). *Biopolymers* 12:287.
15. Li, H. J., et al., (1973). *Biochemistry* 12:1763.
16. Change, C., et al., (1973). Conformational studies of nucleoprotein . Circular dichroism of deoxyribonucleic acid base pairs bound by polylysine. *Biochemistry* 12:3026–3032.
17. Gosule, L., et al., (1976). Compact form of DNA induced by spermidine. *Nature* 259:333–335.
18. Gosule, L., et al., (1978). Condensation of phage DNA by polyamines. *Advances in polyamine research* 1:201–215.
19. Wu, C. H., et al., (1984) *J. Biol. Chem.* 264 (29), 16985–16987
20. Wu, G. Y., et al., (1991) *J. Biol. Chem.* 266 (22), 14338–14342
21. Neda, H., et al., (1991) *J. Biol. Chem* 266 (22), 14143–14146
22. Wilson, J. M., et al., (1992) *J. Biol. Chem.* 267 (2), 963–967

23. Chen, J., et al., (1993) Submitted for publication to FASEB J.
24. Ferkol, T., et al., (1993) *FASEB J.*, 7;1081.
25. Wagner, E., et al., (1991) *Proc. Natl. Acad. Scie. USA*, 88:4255–4259.
26. Laemmli, U. K. (1975) *Proc. Natl. Acad. Sci. USA*, 72:(11), 4288–4292.
27. Lerman, L. S. (1971) *Proc. Natl. Acad. Sci. USA*, 68 (8), 1886–1890
28. Post, C. B., et al., (1982) *Biopolymers*, 21, 2123–2137
29. Hatzoglou, M., et al., (1990) *J. Biol. Chem.* 265:17285–17293.
30. Monsigny, M., et al., (1984) *Biol. Cell.*, 51, 187

TABLE 101

| | Wu et al. | Wagner et al. | Present Invention* |
|---|---|---|---|
| [DNA] mg/ml | ~1 | ~0.01 | ~1 |
| $PO_4/NH_3$ ratio | ~100 | ~1 | ~1.5 |
| Buffer | 150 mM NaCl | 10 mM Hepes (pH 7), 150 mM NaCl | Variable [NaCl] |
| Compaction Method | Annealing | Direct Mixing | Nucleation |
| Structure of the DNA complex | (Psi) | (Psi) or Unimolecular | Unimolecular |
| Size of the complex | ≈200 nm | 80 nm | ~10 nm |
| Diagnostic tools | Gel retardation | Electron microscopy | Circular dichroism and Electron microscopy |
| Expression in vivo | Yes | No | Yes |
| Length of expression | 6 days | — | At least 140 days |

*Preferred embodiment

TABLE 102

Level off Expression of the PEPCK-hFIX Gene in the Livers of Rats Injected with the DNA Complex

| Rat # | Days after injection | Units of hFIX activity |
|---|---|---|
| 1 | 2 | 0.040 |
| 2 | 2 | 0.045 |
| 3 | 4 | 0.045 |
| 4 | 4 | 0.025 |
| 5 | 6 | 0.330 |
| 6 | 8 | 0.135 |
| 7 | 12 | 0.160 |
| 8 | 12 | 0.075 |
| 9 | 32 | 0.125 |
| 10 | 48 | 0.350 |
| 11 | 72 | 0.005 |
| 12 | 136 | 0.105 |

TABLE 103

| State of DNA or DNA/polyca- tion complex | Naked eye (or turdi- metry at 400 nm) | Circular Dichroism | Electron Microscopy | Absorbance at 260 nm |
|---|---|---|---|---|
| Normal DNA (Not complexed) | No turbidity. Clear solution. | Normal DNA spectrum, i.e., maxima at 220 and 269 nm; a minimum at 245 nm, and a zero-point crossover at 258 nm. | Very thin (about 1 nm thick or less) and long (about 300–1,000 nm) fibers. (Fig. 1B) | This absorbance is the reference for the other states |
| Condensed Complex (caused by polycation) | Low turbidity. Almost clear solution. | Identical to the spectrum of unbound (no poly-L-lysine) double stranded DNA in solution; positive maxima at 269 nm and very little contribution from the amide bond of the poly-L-lysine peptide to the spectrum at 220 nm (FIG. 1A) | Individually isolated spherical or toroidal structures. For DNA of about 5 kb, the toroids are about 10–20 nm in external diameter. Larger DNA, will of course compact to form larger toroids Electron dense particles. No tibers. (FIG. 1D) | about 20–30% of reference absorbance |

TABLE 103-continued

| State of DNA or DNA/polycation complex | Naked eye (or turdimetry at 400 nm) | Circular Dichroism | Electron Microscopy | Absorbance at 260 nm |
|---|---|---|---|---|
| Relaxed Complex (caused by excess salt) | No turbidity. Clear solution. | Very difficult to differentiate from the condensed form. The only difference is that there is some contribution from the amide bond of the poly-L-lysine peptide to the spectrum at 220 nm (FIG. 1A) | Rod-like fibers (usually 10–20 times the diameter, of a naked DNA fiber, i.e., usually 10–20 nm thick, and longer than 60 nm) of DNA and branched toroidal structures of increased size (FIG. 1F) | about 80–100% of reference absorbance |
| Precipitated Complex (caused by polycation if insufficient salt) | DNA fibers in solution. | Flat spectrum. (FIG. 1I) | Complex of macroscopic (micrometer range) DNA fibers. | about 1% of reference absorbance |
| Unimolecular Aggregated Complex | Highly variable from fine particulate to highly turbid | Characteristic red-shift and positive ellipticity in the 300–320 nm band | Unimolecular toroidal structures clumping together to form random networks of heterogeneous size and shape | about 10–20% of reference absorbance |
| Multimolecular Aggregated Complex (caused by polycation if insufficient salt)[1] | Clear | Characteristic inversion in the spectrum maxima at 269 nm to the negative. Clear contribution from the amide bond of the poly-L-lysine peptide to the spectrum at 220 mn. (FIG. 1H) | Isolated, multimolecular Toroidal structures of variable size depending on the number of DNA molecules condensed together. The size is usually approximately 10 to 70 times that of the unimolecular toroids (see Wagner et al. and Shapiro et al.) (FIG. 1G) | about 100% of reference absorbance |

[1] The DNA will aggregate into multimolecular complexes when the concentration of poly-L-lysine is increased suddenly in the DNA solution (i.e. by adding poly-L-lysine very rapidly to the vortexing solution of DNA) or the direct mixing of DNA and poly-L-lysine as in the method of Shapiro also used by Wagner et al. Aggregation into multimolecular complexes will be also the result of annealing both components (poly-L-lysine and DNA) in a gradient of decreasing NaCl concentration (i.e. the method of Wu and Wu).

TABLE 104

| Lys# | DNA (% super-coiled) | Initial [NaCl] | Final [NaCl] | [DNA] (mg/ml) | Physical State** | Activity† |
|---|---|---|---|---|---|---|
| 15* | CMV-βGal (50) | 151.6 | 200 | 0.2 | CD: ND EL: ND Turbidity: None | + |
| 20* | MT-hGH (100) | 0 | 267 | 0.85 | CD: ND EL: Relaxed Turbidity: None | − |
| 27* | PEPCK-hLDLR (100) | 178 | 439 | 1 | CD: ND EL: Condensed Turbidity: Low | +++ |
| 56 | RS-Tr (50) | 803 | 1000 | 0.24 | CD: ND EL: ND Turbidity: None | ND |
| 56 | CMV-βGal (50) | 250 | 746 | 0.2 | CD: ND EL: ND Turbidity: Low | ND |
| 56* | PEPCK-hFIX (50) | 800 | 933 | 0.35 | CD: ND EL: Condensed Turbidity: Low | +++ |
| 56* | PEPCK-hFIX (50) | 636 | 970 | 0.6 | CD: ND EL: ND Turbidity: Low | +++ |
| 109* | CMV-βGal (50) | 500 | 909 | 0.2 | CD: + EL: ND Turbidity: Low | +++ |
| 109* | CMV-βGal (50) | 689 | 1000 | 0.39 | CD: ND EL: ND Turbidity: None | ND |
| 109* | CMV-βGal (50) | 616 | 1036 | 0.95 | CD: ND EL: ND Turbidity: Low | +++ |
| 109* | CMV-βGal (50) | 735 | 941 | 0.39 | CD: ND EL: ND Turbidity: Low | +++ |
| 109* | CMV-βGal (50) | 500 | 1031 | 0.7 | CD: + EL: ND Turbidity: Low | ND |
| 109 | PEPCK-βGal (50) | 617 | 1004 | 0.3 | CD: ND EL: ND Turbidity: None | − |
| 109* | PEPCK-βGal (50) | 1085 | 1174 | 0.88 | CD: ND EL: ND Turbidity: Low | +++ |
| 109* | PEPCK-hFIX (50) | 630 | 1063 | 0.8 | CD: + EL: Condensed Turbidity: Low | +++ |
| 109 | PEPCK-hFIX (50) | 636 | 970 | 0.26 | CD: ND EL: ND Turbidity: None | ND |
| 109 | PEPCK-hFIX (50) | 750 | 1120 | 0.8 | CD: ND EL: Relaxed Turbidity: None | ++ |
| 109* | PEPCK-hFIX (50) | 812 | 1098 | 0.7 | CD: ND EL: Condensed Turbidity: Low | +++ |
| 109 | PEPCK-hFIX (50) | 812 | 1127 | 0.69 | CD: ND EL: Relaxed Turbidity: None | ++ |
| 109* | SV40-luc (80) | 1091 | 1144 | 0.9 | CD: ND EL: Condensed Turbidity: Low | +++ |
| 109* | SV40-luc (80) | 1091 | 1144 | 0.9 | CD: ND EL: Condensed Turbidity: Low | +++ |
| 109* | SV40-luc (80) | 961 | 1140 | 0.88 | CD: ND EL: ND Turbidity: Low | +++ |
| 109* | SV40-luc (80) | 1091 | 1144 | 0.8 | CD: ND EL: ND Turbidity: Low | +++ |
| 109 | SV40-luc (80) | 666 | 1000 | 0.19 | CD: + EL: Relaxed Turbidity: None | ND |
| 109* | SV40-luc (80) | 961 | 1121 | 0.8 | CD: ND EL: ND Turbidity: None | +++ |
| 109* | SV40-luc (80) | 735 | 972 | 0.55 | CD: ND EL: ND Turbidity: Low | +++ |
| 109* | Salmon sperm DNA (0) | 900 | 1231 | 1 | CD: ND EL: ND Turbidity: None | ND |
| 109 | PEPCK-OTC (50) | 774 | 948 | 0.9 | CD: ND EL: ND Turbidity: Low | ND |
| 123 | SV40-luc (100) | 719 | 1044 | 0.95 | CD: ND EL: Relaxed Turbidity: None | − |
| 123 | SV40-luc (100) | 905 | 1086 | 1 | CD: ND EL: Relaxed Turbidity: None | − |
| 123 | SV40-luc (100) | 689 | 1019 | 0.95 | CD: ND EL: ND Turbidity: None | − |
| 123 | SV40-luc (100) | 783 | 978 | 0.5 | CD: ND EL: ND Turbidity: None | − |
| 123 | SV40-luc (100) | 905 | 1149 | 0.57 | CD: ND EL: Relaxed Turbidity: None | − |
| 123* | CMV-βGal (ND) | 825 | 1020 | 0.76 | CD: ND EL: ND Turbidity: | ND |

TABLE 104-continued

| Lys# | DNA (% super-coiled) | Initial [NaCl] | Final [NaCl] | [DNA] (mg/ml) | Physical State** | Activity† |
|---|---|---|---|---|---|---|
| 150* | CMV-βGal (ND) | 886 | 1077 | 0.5 | CD: ND EL: Condensed Turbidity: Low | +++ |
| 150* | SV40-luc (80) | 800 | 972 | 0.36 | CD: ND EL: ND Turbidity: Low | +++ |
| 150 | SV40-luc (80) | 821 | 868 | 0.3 | CD: Psi DNA EL: Aggregated Turbidity: High | – |
| 150* | SV40-luc (80) | 821 | 968 | 0.3 | CD: + EL: Condensed Turbidity: Low | +++ |
| 150 | SV40-luc (80) | 821 | 1071 | 0.3 | CD: + EL: Relaxed Turbidity: None | – |
| 240* | SV40-luc (80) | 711 | 1125 | 1 | CD: ND EL: Condensed Turbidity: Low | +++ |
| 240 | SV40-luc (80) | 711 | 1162 | 1 | CD: ND EL: Relaxed Turbidity: Low | + |
| 240 | SV40-luc (80) | 711 | 1280 | 1 | CD: ND EL: Relaxed Turbidity: None | – |
| 240 | SV40-luc (80) | 800 | 1007 | 1 | CD: ND EL: Aggregated Turbidity: High | – |
| 240 | T7-T7 (90) | 708 | 1187 | 0.9 | CD: + EL: Condensed Turbidity: Low | ND |
| 240 | T7-T7 (90) | 708 | 1250 | 0.9 | CD: + EL: Relaxed Turbidity: None | – |
| 240 | PEPCK-hLDLR (100) | 642 | 947 | 0.73 | CD: Psi DNA EL: Aggregated Turbidity: None | – |
| 240 | PEPCK-OTC (50) | 706 | 1174 | 0.35 | CD: ND EL: ND Turbidity: None | ND |
| 240 | PEPCK-OTC (50) | 898 | 1153 | 0.64 | CD: ND EL: ND Turbidity: None | ND |

*Used in compiling Table 105.

ND = Not determined

**Physical state of the DNA complex after polycation binding.

1. When circular dichroism (CD) was determined the results are indicated as follows: spectral changes due to the polycation condensation of DNA are insignificant (+); polycation condensation resulted in Psi-form DNA due to aggregation into multimolecular complexes (either rod-like or toroidal) (Psi DNA); appearance of an aberrant spectrum associated with a highly aggregative state (–).

2. Electron microscopic results have been indicated as follows: the association of the polycation with the DNA results in aggregation into complexes of increased size (>60 nm) (Aggregated); the structures resulting from the condensation are rod-like relaxed toroids of increased size (Relaxed); polycation binding results in proper condensation (toroids <30 nm in diameter) (Condensed). The number of properly condensed structures (toroids) per microscopic field has not been determined. There is approximately 3-fold variation in the number of toroids visible in the EL with different preparations of DNA complex.

3. Turbidity measurements are based on visual inspection of the final solution of DNA complex.

†A relative indication of the activity of the introduced gene after introduction of the DNA complex: hFIX (human factor IX) is measured by the western blot hybridization or by a functional activity assay of rat plasma samples.

βGal (β-galactosidase) activity is measured by in situ histochemistry in fixed cells or tissue sections.

luc (luciferase) activity is measured using a specific enzyme activity assay with tissue extracts.

hLDLR (human LDL receptor) activity was measured indirectly after determination of the total serum cholesterol levels in a rabbit model for LDL receptor deficiency.

hGH (human growth hormone) activity refers to a direct measurement of hGH levels in the serum of animals transfected with the DNA complex. A radio-immuno assay specific for hGH was used.

The activity is relative to all the experiment performed with the same DNA. Not detectable activity after introduction of the DNA complex is indicated by "–".

TABLE 105

Final [NaCl] = −555.75 + [DNA] mg/ml*180.91 + log (lys length)*y18.32

Regression Statistics

Multiple R 0.881909585
R Square 0.777764515
Adjusted R Square 0.743574441
Standard Error 135.5087624
Observations 16

Analysis of Variance

|  | df | Sum of Squares | Mean Square | F | Significance F |
|---|---|---|---|---|---|
| Regression | 2 | 835435.3166 | 417717.6583 | 22.748254 | 5.6792E-05 |
| Residual | 13 | 238714.1209 | 18362.62469 |  |  |
| Total | 15 | 1074149.438 |  |  |  |

|  | Coefficients | Standard Error | t Statistic | P-value | Lower 95% |
|---|---|---|---|---|---|
| Intercept | −555.757861 | 228.34416556 | 2.433887324 | 0.0279103 | −1049.059922 |
| [DNA] mg/ml | 180.9113279 | 125.4285365 | 1.442345841 | 0.1697596 | −90.06049864 |
| log (lys length) | 718.3211054 | 117.7844848 | 6.098605488 | 2.037E-05 | 463.8632453 |

TABLE 106

Estimated and experimental size of condensed DNA complexes

| | | Condensed diameter (nm ± SD) | | |
|---|---|---|---|---|
| DNA | size(bp) | Electron Microscope[a] | Hydrated model (partial specific volume)[b] | Hydrated model (X-ray diffraction density)[c] |
| PEPCK-hFIX | 4,500 | 12.80 ± 1.56 | 18 | 22 |
| PEPCK-hOTC | 5,300 | 18.00 ± 1.83 | 20 | 23 |
| SV40-luciferase | 5,600 | 16.95 ± 3.50 | 20 | 24 |
| PEPCK-CAT | 5,800 | 16.30 ± 2.56 | 20 | 24 |
| CMV-hLDLr | 7,400 | 20.70 ± 2.60 | 22 | 26 |
| φ29[d] | 18,000 | 38[e] | 40 | 47 |

[a] measured diameter of at least 10 DNA complexes in a printed photograph (× 240,000).
[b] calculated diameter of a unimolecular DNA complex assuming a condensed sphere. The partial specific volume of Na-DNA was deemed to be 0.5 ml/g. The contribution of galactosylated poly-L-lysine at a charge ratio of 1:1 has been added. The molecular weight of DNA was calculated based on an average molecular weight of 6,500 dalton/10 bp. The formula used is: DNA molecular weight (daltons)/6.023 × $10^{23}$ × 0.5 (ml/g) = ml occupied by a molecule of DNA of X molecular weight. Diameter obtained from the formula for the volume of a sphere.
[c] calculated diameter of a unimolecular DNA complex assuming a condensed sphere. The calculation assumed a hydrated density of 1.25 ± 0.1 g/ml as determined by X-ray difraction. The contribution of a galactosylated poly-L-lysine at a charge ratio of 1:1 has been added. The molecular weight of DNA was calculated based on an average molecular weight of 6,500 dalton/10 bp. The formula is: DNA molecular weight (daltons)/6.023 × $10^{23}$ × 1.25 (g/ml) = ml occupied by a molecule of DNA of X molecular weight. Diameter obtained from the formula for the volume of a sphere.
[d] from the literature.
[e] the size to the phage prohead includes the protein out-shell.

We claim:

1. A non-naturally occurring composition comprising unaggregated nucleic acid complexes, each complex consisting essentially of a single nucleic acid molecule and one or more carrier molecules, said carrier molecule having a nucleic acid binding moiety through which it is complexed to the nucleic acid, and a target cell-binding moiety through which it may bind to a target cell and whereby the complex may more readily enter the target cell, wherein said complex is compacted to a diameter which is less than (a) double the theoretical minimum diameter of a complex of said single nucleic acid molecule and a sufficient number of carrier molecules to provide a charge ratio of 1:1, in the form of a condensed sphere, or (b) 30 nm, whichever is larger.

2. The composition of claim 1, wherein said complex is compacted to a diameter of less than 90 nm.

3. The composition of claim 1, wherein the nucleic acid complex is compacted to a diameter less than 30 nm.

4. The composition of claim 1, wherein the nucleic acid complex is compacted to a diameter less than 23 nm.

5. The composition of claim 1, wherein the nucleic acid complex is compacted to a diameter not more than 12 nm.

6. The composition of claim 1 wherein the target cell binding moiety is an antibody or a specific binding fragment of an antibody.

7. The composition of claim 1 in which the nucleic acid is 100 to 100,000 bases, if single stranded, or 100 to 100,000 base pairs, if double stranded.

8. The composition of claim 6 in which the antibody specifically binds CD4 or gp120.

9. The composition of claim 1 wherein the target cell binding moiety is a lectin, or a carbohydrate.

10. The composition of claim 9 wherein the target cell binding moitey is a carbohydrate selected from the group consisting of galactose, lactose, mannose and mannose-6-phosphate.

11. The composition of claim 1 wherein the target cell binding moiety is a peptide or protein.

12. The composition of claim 11 wherein the target cell binding moiety is selected from the group consisting of insulin, epidermal growth factor, tumor necrosis factor, prolactin, chorionic gonadotropin, follicle stimulating hormone, luteinizing hormone, glucagon, lactoferrin, transferrin, apolipoprotein E, gp120 and albumin.

13. The composition of claim 1 in which the nucleic acid binding moiety is an antibody or a specific binding fragment of an antibody.

14. The composition of claim 1 in which the nucleic acid binding moiety is a polycation.

15. The composition of claim 1 in which the polycation is polylysine.

16. The composition of claim 1 in which the nucleic acid is DNA.

17. The composition of claim 1 in which the nucleic acid is RNA.

18. The composition of claim 1 in which the nucleic acid is an analogue of DNA or RNA which is more resistant to degradation in vivo.

19. The composition of claim 1 in which the nucleic acid is an analogue of DNA or RNA which more readily diffuses through cell membranes.

20. The composition of claim 1 in which the nucleic acid is an analogue of DNA in which the methylphosphonate analogue of the naturally occurring mononucleotide appears.

21. The composition of claim 1 wherein the nucleic acid comprises an expressible gene which is functional in a target cell to which said target cell binding moiety binds.

22. The composition of claim 1 in which the gene encodes a protein selected from the group consisting of enzymes which in mutated form are associated with specific metabolic defects, receptors, toxins, ion channels membrane transporters, and cytoskeletal proteins.

23. The composition of claim 1 wherein the nucleic acid comprises sequences homologous to genetic material of the target cell, whereby it may be inserted into the genome thereof by homologous recombination.

24. The composition of claim 1 in which the nucleic acid molecule is "antisense" to a target nucleic acid sequence of the target cell, or of a virus which can infect the target cell, whereby it may hybridize sufficiently thereto to inhibit transcription or translation of the target nucleic acid sequence.

25. The composition of claim 1 wherein the nucleic acid is encapsulated in a liposome.

26. The composition of claim 1 wherein the nucleic acid binding moiety is covalently linked to the target cell binding moiety.

27. The composition of claim 1 wherein the nucleic acid molecule is cDNA.

28. The composition of claim 1 wherein the complex is compacted to a diameter which is less than is less than (a) double the theoretical minimum diameter of a complex of said single nucleic acid molecule and a sufficient number of carrier molecules to provide a charge ratio of 1:1, in the form of a condensed sphere.

29. A composition comprising unaggregated nucleic acid complexes, each complex consisting essentially of a single double-stranded nucleic acid molecule and one or more carrier molecules, said carrier molecule having a nucleic acid binding moiety through which it is complexed to the nucleic acid, and a target cell-binding moiety through which it may bind to a target cell and whereby the complex may more readily enter the target cell, wherein said complex is compacted to a diameter which is less than (a) double the theoretical minimum diameter of a complex of said single nucleic acid molecule and a sufficient number of carrier molecules to provide a charge ratio of 1:1, in the form of a condensed sphere, or (b) 30 nm, whichever is larger.

30. The composition of claim 29 in which the nucleic acid is DNA.

31. The composition of claim 29, wherein the nucleic acid complex is compacted to a diameter not more than 12 nm.

32. The composition of claim 29, wherein the target cell binding moiety is an antibody or a specific binding fragment of an antibody.

33. The composition of claim 32 in which the antibody specifically binds CD4 or gp120.

34. The composition of claim 29 wherein the target cell binding moiety is a lectin, or a carbohydrate.

35. The composition of claim 34 wherein the carbohydrate is selected from the group consisting of galactose, lactose, mannose and mannose-6-phosphate.

36. The composition of claim 29 wherein the target cell being moiety is selected from the group consisting of insulin, epidermal growth factor, tumor necrosis factor, prolactin, chorionic gonadotropin, follicle stimulating hormone, luteinizing hormone, glucagon, lactoferrin, transferrin, apolipoprotein E, gp120 and albumin.

37. The composition of claim 29 in which the nucleic acid binding moiety is an antibody or a specific binding fragment of an antibody.

38. The composition of claim 29 in which the polycation is polylysine.

39. The composition of claim 29 in which the nucleic acid is an analogue of DNA or RNA which is more resistant to degradation in vivo.

40. The composition of claim 29 in which the nucleic acid is an analogue of DNA or RNA which more readily diffuses through cell membranes.

41. The composition of claim 29 in which the nucleic acid is an analogue of DNA in which the methylphosphonate analogue of the naturally occurring mononucleotide appears.

42. The composition of claim 29 in which the nucleic acid molecule is "antisense" to a target nucleic acid sequence of the target cell, or of a virus which can infect the target cell, whereby it may hybridize sufficiently thereto to inhibit transcription or translation of the target nucleic acid sequence.

43. The composition of claim 29 wherein the nucleic acid is encapsulated in a liposome.

44. The composition of claim 29, wherein the nucleic acid complex is compacted to a diameter less than 23 nm.

45. The composition of claim 29 wherein the target cell binding moiety is a peptide or protein.

46. The composition of claim 29 in which the nucleic acid is RNA.

47. The composition of claim 29 wherein the nucleic acid comprises an expressible gene which is functional in a target cell to which said target cell binding moiety binds.

48. The composition of claim 29 in which the gene encodes a protein selected from the group consisting of enzymes which in mutated form are associated with specific metabolic defects, receptors, toxins, ion channels membrane transporters, and cytoskeletal proteins.

49. The composition of claim 29 wherein the nucleic acid comprises sequences homologous to genetic material of the target cell, whereby it may be inserted into the genome thereof by homologous recombination.

50. The composition of claim 29 in which the nucleic acid is 100 to 100,000 base pairs.

51. The composition of claim 29, wherein said complex is compacted to a diameter of less than 90 nm.

52. The composition of claim 29, wherein the nucleic acid complex is compacted to a diameter less than 30 nm.

53. The composition of claim 29 in which the nucleic acid is 100 to 100,000 base pairs.

54. The composition of claim 29 in which the nucleic acid binding moiety is a polycation.

55. The composition of claim 29 wherein the nucleic acid binding moiety is covalently linked to the the target cell binding moiety.

56. The composition of claim 29 wherein the nucleic acid molecule is cDNA.

57. The composition of claim 29 wherein the complex is compacted to a diameter which is less than is less than (a) double the theoretical minimum diameter of a complex of said single nucleic acid molecule and a sufficient number of carrier molecules to provide a charge ratio of 1:1, in the form of a condensed sphere.

* * * * *

UNITED STATES PATENT AND TRADEMARK OFFICE
CERTIFICATE OF CORRECTION

PATENT NO. : 5,877,302
DATED : March 2, 1999
INVENTOR(S) : Richard W. Hanson; Jose C. Perales and Thomas W. Ferkol It is certified that error appears in the above-indentified patent and that said Letters Patent is hereby corrected as shown below:

Column 1, after "COMPACTED NUCLEIC ACIDS AND THEIR DELIVERY TO CELLS" insert

--This invention was made with government support under DK21859, DK25541 and HL53672 awarded by the National Institute of Health. The government has certain rights in the invention.--

Signed and Sealed this

Twenty-ninth Day of June, 1999

Attest:

Q. TODD DICKINSON

Attesting Officer

Acting Commissioner of Patents and Trademarks